US010212939B2

(12) United States Patent
Floro et al.

(10) Patent No.: US 10,212,939 B2
(45) Date of Patent: *Feb. 26, 2019

(54) METHYLOBACTERIUM COMPOSITIONS AND PLANTS, PLANT PARTS AND SEEDS COATED THEREWITH

(71) Applicant: NewLeaf Symbiotics, Inc., St. Louis, MO (US)

(72) Inventors: Rachel DiDonato Floro, St. Louis, MO (US); Justin Lee, St. Louis, MO (US); Gregg Bogosian, Clarkson Valley, MO (US)

(73) Assignee: NEWLEAF SYMBIOTICS, INC., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/101,374

(22) PCT Filed: Dec. 4, 2014

(86) PCT No.: PCT/US2014/068558
§ 371 (c)(1),
(2) Date: Jun. 2, 2016

(87) PCT Pub. No.: WO2015/085063
PCT Pub. Date: Jun. 11, 2015

(65) Prior Publication Data
US 2016/0302425 A1 Oct. 20, 2016

Related U.S. Application Data

(60) Provisional application No. 61/954,840, filed on Mar. 18, 2014, provisional application No. 61/911,516, filed on Dec. 4, 2013.

(51) Int. Cl.
A01N 63/00 (2006.01)

(52) U.S. Cl.
CPC .................... *A01N 63/00* (2013.01)

(58) Field of Classification Search
CPC ...................................... A01N 63/00
USPC ........................................ 504/117
See application file for complete search history.

(56) References Cited

U.S. PATENT DOCUMENTS

| 4,336,334 | A | 6/1982 | Powell et al. |
| 5,106,648 | A | 4/1992 | Williams |
| 5,302,525 | A | 4/1994 | Groleau et al. |
| 5,403,799 | A | 4/1995 | Miller et al. |
| 5,403,809 | A | 4/1995 | Miller et al. |
| 5,512,069 | A | 4/1996 | Holland et al. |
| 5,961,687 | A | 10/1999 | Joshi et al. |
| 6,107,067 | A | 8/2000 | Miller et al. |
| 6,174,837 | B1 | 1/2001 | Joshi et al. |
| 6,329,230 | B1 | 12/2001 | Matsuda |
| 7,214,509 | B2 | 5/2007 | Schnoor et al. |
| 7,435,878 | B2 | 10/2008 | Holland |
| 8,153,118 | B2 | 4/2012 | Holland et al. |
| 8,181,388 | B2 | 5/2012 | Berger |
| 8,778,660 | B2 | 7/2014 | Holland et al. |
| 9,181,541 | B2 | 11/2015 | Bogosian |
| 9,845,462 | B2 | 12/2017 | Bogosian |
| 2001/0001095 | A1 | 5/2001 | Joshi et al. |
| 2003/0211082 | A1 | 11/2003 | Holland |
| 2004/0175407 | A1* | 9/2004 | McDaniel ............... A62D 3/02 424/423 |
| 2005/0096225 | A1 | 5/2005 | Johnson |
| 2006/0150488 | A1 | 7/2006 | Pearce et al. |
| 2006/0228797 | A1* | 10/2006 | Holland ................ A01N 63/00 435/377 |
| 2007/0074451 | A1 | 4/2007 | Pearce et al. |
| 2010/0093538 | A1 | 4/2010 | Gnanamanickam |
| 2013/0324407 | A1* | 12/2013 | Bogosian ............... C12N 11/02 504/117 |
| 2015/0337256 | A1 | 11/2015 | Bogosian |
| 2016/0046925 | A1 | 2/2016 | Bogosian |
| 2016/0073641 | A1 | 3/2016 | Allen et al. |
| 2016/0120188 | A1 | 5/2016 | Bogosian |
| 2016/0295868 | A1 | 10/2016 | Jones et al. |
| 2016/0302423 | A1 | 10/2016 | Jones et al. |
| 2016/0302424 | A1 | 10/2016 | DiDonato et al. |
| 2017/0086464 | A1 | 3/2017 | Floro et al. |
| 2017/0135352 | A1 | 5/2017 | Breakfield et al. |

(Continued)

FOREIGN PATENT DOCUMENTS

| CA | 2183275 A1 | 2/1998 |
| CN | 101028008 A | 9/2007 |

(Continued)

OTHER PUBLICATIONS

ATCC Catalogue. ATCC Bacteria and Bacteriophages, 19th edition, 1996, pp. 231-214.*
ATCC Preservation Methods: Freezing and freeze-drying; Published by ATCC, 2nd edition, 1991, pp. 5-13.*
Wessman et al. (J Sci Food Agric 2011, 91, pp. 2518-2528).*
International Search Report and Written Opinion dated Apr. 28, 2015, issued in PCT Patent Application No. PCT/US2014/068558.
Joe et al., "Development of Alginate-Based Aggregate Inoculants of *Methylobacterium* sp. and Azospirillum Brasilence Tested Under In Vitro Conditions to Promote Plant Growth", Journal of Applied Microbiology, Nov. 22, 2013, pp. 408-423, vol. 116, Issue 2.
Madhaiyan et al., "Metal Tolerating Methylotrophic Bacteria Reduces Nickel and Cadmium Toxicity and Promotes Plant Growth of Tomato (*Lycopersicon esculentum* L.)", Chemosphere, May 23, 2007, pp. 220-228, vol. 69.

(Continued)

Primary Examiner — Johann R Richter
Assistant Examiner — Courtney A Brown
(74) Attorney, Agent, or Firm — Thompson Coburn LLP; Charles P. Romano

(57) ABSTRACT

The present invention provides both compositions comprising *Methylobacterium* and compositions comprising *Methylobacterium* that are depleted of substances that promote growth of resident microorganisms on a lettuce plant or seed. Also provided are methods for improving lettuce production, methods of making the compositions, and methods of treating a lettuce plant or seed with the compositions comprising *Methylobacterium*.

20 Claims, No Drawings
Specification includes a Sequence Listing.

(56) References Cited

U.S. PATENT DOCUMENTS

| | | | |
|---|---|---|---|
| 2017/0164618 | A1 | 6/2017 | Breakfield et al. |
| 2017/0238553 | A1 | 8/2017 | Jones et al. |

FOREIGN PATENT DOCUMENTS

| | | | | |
|---|---|---|---|---|
| EP | 0140723 | A1 | 5/1985 | |
| EP | 2390345 | A1 | 11/2011 | |
| KR | 100755509 | B1 | 9/2007 | |
| KR | 20070106867 | A | 11/2007 | |
| KR | 20070106868 | A | 11/2007 | |
| KR | 20070111915 | A | 11/2007 | |
| KR | 20080097568 | A | 11/2008 | |
| KR | 100953179 | B1 | 4/2010 | |
| KR | 10-1195899 | B1 | 10/2012 | |
| WO | 2000/060052 | A1 | 10/2000 | |
| WO | 2003046226 | A1 | 6/2003 | |
| WO | 2012012671 | A2 | 1/2012 | |
| WO | 2012/140212 | A2 | 10/2012 | |
| WO | 2012140207 | A2 | 10/2012 | |
| WO | WO 2012140212 | A2 * | 10/2012 | ............ A01N 63/00 |
| WO | 2013141815 | A1 | 9/2013 | |
| WO | WO-2013141815 | A1 * | 9/2013 | ............ A01N 63/00 |
| WO | 2013/181610 | A1 | 12/2013 | |
| WO | 2014194189 | A1 | 12/2014 | |
| WO | 2015/085117 | A1 | 6/2015 | |
| WO | 2015142393 | A1 | 9/2015 | |
| WO | 2016069564 | A1 | 5/2016 | |
| WO | 2016201284 | A2 | 12/2016 | |
| WO | 2018/106899 | | 6/2018 | |

OTHER PUBLICATIONS

Rastogi et al., "Leaf Microbiota in an Agroecosystem Spatiotemporal Variation in Bacterial Community Composition on Field-Grown Lettuce", The ISME Journal, Apr. 26, 2012. pp. 1812-1822, vol. 6.
Adams, "The Principles of Freeze-Drying", Methods in Molecular Biology, 2007, pp. 15-38, vol. 368.
Balachandar et al., "Genetic and Metabolic Diversity of Pink-Pigmented Facultative Methylotrophs in Phyllosphere of Tropical Plants", Brazilian Journal of Microbiology, 2008, pp. 68-73, vol. 39.
Chitra et al., "Multigeneric PGPR Coaggregates: A Novel Bioformulation and Delivery System for the Induction of Systemic Resistance in Rice—*Xanthomonas oryzae* Pathosystem Under Lowland Condition", Golden Research Thoughts, Oct. 2013, pp. 1-10, vol. 3, No. 4.
Chitra et al., "Multigeneric Microbial Coaggregates-Effect of Different Bioformulations of PGPR Cells on the Enhancement of PGPR Characteristics and Biocontrol Against *Xanthomonas oryzae* pv. oryzae in Rice Grown Under Lowland Condition", Journal of Applicable Chemistry, 2013, pp. 1132-1140, vol. 2, No. 5.
Corpe et al., "Methanol-Utilizing Bacteria Associated with Green Plants", Developments in Industrial Microbiology, 1982, pp. 483-493, vol. 23.
De Valdez et al., "Effect of Drying Medium on Residual Moisture Content and Viability of Freeze-Dried Lactic Acid Bacteria", Applied and Environmental Microbiology, Feb. 1985, pp. 413-415, vol. 49, No. 2.
GenBank entry FP103042, Nov. 5, 2010, retreived on Jan. 5, 2016 from http://www.ncbi.nlm.nih.gov/nuccore/254265931?sat=18&satkey-27964264.
Gomathy et al., "Impact of Biofertigation of Azophosmet on Cotton Yield under Dripirrigation", Research Journal of Agriculture and Biological Sciences, 2008, pp. 695-699, vol. 4, No. 6.
International Search Report and Written Opinion dated Feb. 16, 2016, issued in PCT Patent Application No. PCT/US2015/057521.
International Search Report and Written Opinion dated Feb. 20, 2015, issued in PCT Patent Application No. PCT/US2014/068657.
International Search Report and Written Opinion dated Feb. 23, 2015, issued in PCT Patent Application No. PCT/US2014/068663.
International Search Report and Written Opinion dated Mar. 2, 2015, issued in PCT Patent Application No. PCT/US2014/068660.
International Search Report and Written Opinion for PCT/US2013/043722 dated Aug. 23, 2013.
Jiang et al., "Methanotrophs: Multifunctional Bacteria with Promising Applications in Environmental Bioengineering", Biochemical Engineering Journal, May 15, 2010, pp. 277-288, vol. 49 No. 3.
Kongkhaem et al., "Silica-Immobilized *Methylobacterium* sp. NP3 and *Acinetobacter* sp. PK1 Degrade High Concentrations of Phenol", Letters in Applied Microbiology, May 2011, pp. 448-455, vol. 52 No. 5.
Leslie et al., "Trehalose and Sucrose Protect Both Membranes and Proteins in Intact Bacteria during Drying", Applied and Environmental Microbiology, Oct. 1995, pp. 3592-3597, vol. 61 No. 10.
Li et al., "2,4,5,-Trichlorophenol Degradation Using a Novel TiO2-Coated Biofilm Carrier: Roles of Adsorption, Photocatalysis, and Biodegradation", Environmental Science & Technology, Aug. 23, 2011, pp. 8359-8367. vol. 45. No. 19.
Ntsaluba et al., "Studies on Bioflocculant Production by *Methylobacterium* sp. Obi Isolated from a Freshwater Environment in South Africa", African Journal of Microbiology Research, Nov. 16, 2011, pp. 4533-4540, vol. 5 No. 26.
Poorniammal et al., "In Vitro Biocontrol Activity of Methylobacterium Extorquens Against Fungal Pathogens", International Journal of Plant Protection, 2009, pp. 59-62, vol. 2, No. 1.
Simoes et al., "Adhesion and Biofilm Formation on Polystyrene by Drinking Water-Isolated Bacteria", Antonie van Leeuwenhoek, Apr. 20, 2010, pp. 317-329, vol. 98 No. 3.
Sundaram et al., "Bioinoculants for Sustainable and Cost Effective Production of High Quality Fibre", TMC Annual Report, TMC-MMI-2.3, 2006, pp. 1-7, Retrieved from the internet, Apr. 2, 2014, http://www.tmc.cicr.org.in/PDF/22.3.pdf.
Verhoef et al., "*Methylobacterium* sp. Isolated from a Finnish Paper Machine Produces Highly Pyruvated Galactan Exopolysaccharide", Carbohydrate Research, 2003, pp. 1851-1859, vol. 338.
Vuilleumier et al., "Methylobacterium Genome Sequences: A Reference Blueprint to Investigate Microbial Metabolism of C1 Compounds from Natural and Industrial Sources", Public Library of Science One, May 18, 2009, pp. 1-16; vol. 4, No. 5.
Abanda-Nkpwatt et al., "Molecular Interaction Between Methylobacterium Extorquens and Seedlings: Growth Promotion, Methanol Consumption, and Localization of the Methanol Emission Site", Journal of Experimental Botany, Oct. 16, 2006, vol. 57 No. 15, pp. 4025-4032.
Corpe et al., "Ecology of the Methylotrophic Bacteria on Living Leaf Surfaces", FEMS Microbiology Ecology, 1989, vol. 62, pp. 243-250.
Green, "Methylobacterium", Prokaryotes, 2006, vol. 5, Chapter 3.1.13, pp. 257-265.
Holland, "Methylobacterium and Plants", Recent Research Developments in Plant Physiology, 1997, pp. 207-213, vol. 1.
Joe et al., Development of Alginate-Based Aggregate Inoculants of *Methylobacterium* sp. and Azospirillum Brasilense Tested Under in vitro Conditions to Promote Plant Growth, Journal of Applied Microbiology, Nov. 2012, pp. 1-46.
Lidstrom et al., "Plants in the Pink: Cytokinin Production by Methylbacterium", Journal of Bacteriology, Apr. 2002, p. 1818, vol. 184, No. 7.
Madhaiyan et al., "Growth promotion and induction of systemic resistance in rice cultivar Co-47 (*Oryza sativa* L.) by *Methylobacterium* spp.", Biology and Fertility of Soils, 2005, pp. 350-358, vol. 41.
Madhaiyan et al., "Pink-Pigmented Facultative Methylotrophic Bacteria Accelerate Germination, Growth and Yield of Sugarcane Clone Co86032 (*Saccharum officinarum* L.)", Biology and Fertility of Soils, 2005, pp. 350-358, vol. 41.
Omer et al., "Plant Colonization by Pink-Pigmented Facultative Methylotrophic Bacteria (PPFMs)", FEMS Microbiology Ecology, Mar. 2004, pp. 319-326, vol. 47 No. 3.
Sy, A. et al., "Methylotrophic Metabolism is Advantageous for Methylobacterium extorquens during Colonization of Medicago truncatula under Competitive Conditions", Applied and Environmental Microbiology, 2005, pp. 7245-7252, vol. 71, No. 11.

(56) References Cited

OTHER PUBLICATIONS

Vaidehi et al., "Adhesion of Methylobacterium Cells to Rice Roots: Active Metabolism of Miropartner Determines the Degree of Adsorption Level at Rhizosphere", International Journal of Research in Pure and Applied Microbiology, 2012, pp. 54-58, vol. 2, No. 4.
RD4AG Lettuce Field Trial Report dated May 31, 2015.
Pacific Ag Research, "Evaluation of Efficacy Using NLS Strains as Biostimulant in Direct Seeded Cool Season Lettuce Approach", Research and Development Project Report, Winter-Summer 2015.
RD4AG Lettuce Field Trial Report dated Jan. 30, 2015.
Ryu et al., "Plant Growth Substances Produced by *Methylobacterium* spp. and Their Effect on Tomato (*Lycopersicon esculentum* L.) and Red Pepper (*Capsicum annuum* L.) Growth", Journal of Microbiology and Biotechnology, Oct. 2006, pp. 1622-1628, vol. 16, No. 10.
Tani et al., "Methylobacterium Species Promoting Rice and Barley Growth and Interaction Specificity Revealed with Whole-Cell Matrix-Assisted Laser Desorption/Ionization-Time-of-Flight Mass Spectrometry (MALDI-TOF/MS) Analysis" PLOS ONE, Jun. 8, 2015, 15 pages.
TerrasymTM 402 Product Sheet; Jan. 2018.

\* cited by examiner

METHYLOBACTERIUM COMPOSITIONS AND PLANTS, PLANT PARTS AND SEEDS COATED THEREWITH

CROSS REFERENCE TO RELATED APPLICATIONS

This patent application is a 35 U.S.C. § 371 US national stage application of International Patent Application PCT/US2014/068558, filed Dec. 4, 2014 and incorporated herein by reference in its entirety, which claims the benefit of U.S. Provisional Patent Application No. 61/954,840, filed Mar. 18, 2014, and U.S. Provisional Patent Application No. 61/911,516, filed Dec. 4, 2013, which are each incorporated herein by reference.

SEQUENCE LISTING STATEMENT

A sequence listing containing the file named 53907-155282_SL.txt which is 15,167,357 bytes (measured in MS-Windows®) and created on Jun. 1, 2016, comprises 10,250 sequences, is provided herewith via the USPTO's EFS system, and is incorporated herein by reference in its entirety.

BACKGROUND

One-carbon organic compounds such as methane and methanol are found extensively in nature, and are utilized as carbon sources by bacteria classified as methanotrophs and methylotrophs. Methanotrophic bacteria include species in the genera *Methylobacter, Methylomonas, Methylomicrobium, Methylococcus, Methylosinus, Methylocystis, Methylosphaera, Methylocaldum*, and *Methylocella* (Lidstrom, 2006). Methanotrophs possess the enzyme methane monooxygenase, that incorporates an atom of oxygen from $O_2$ into methane, forming methanol. All methanotrophs are obligate one-carbon utilizers that are unable to use compounds containing carbon-carbon bonds. Methylotrophs, on the other hand, can also utilize more complex organic compounds, such as organic acids, higher alcohols, sugars, and the like. Thus, methylotrophic bacteria are facultative methylotrophs. Methylotrophic bacteria include species in the genera *Methylobacterium, Hyphomicrobium, Methylophilus, Methylobacillus, Methylophaga, Aminobacter, Methylorhabdus, Methylopila, Methylosulfonomonas, Marinosulfonomonas, Paracoccus, Xanthobacter, Ancylobacter* (also known as *Microcyclus*), *Thiobacillus, Rhodopseudomonas, Rhodobacter, Acetobacter, Bacillus, Mycobacterium, Arthobacter*, and *Nocardia* (Lidstrom, 2006).

Most methylotrophic bacteria of the genus *Methylobacterium* are pink-pigmented. They are conventionally referred to as PPFM bacteria, being pink-pigmented facultative methylotrophs. Green (2005, 2006) identified twelve validated species in the genus *Methylobacterium*, specifically *M. aminovorans, M. chloromethanicum, M. dichloromethanicum, M. extorquens, M. fujisawaense, M. mesophilicum, M. organophilum, M. radiotolerans, M. rhodesianum, M. rhodinum, M. thiocyanatum*, and *M. zatmanii*. However, *M. nidulans* is a nitrogen-fixing *Methylobacterium* that is not a PPFM (Sy et al., 2001). *Methylobacterium* are ubiquitous in nature, being found in soil, dust, fresh water, sediments, and leaf surfaces, as well as in industrial and clinical environments (Green, 2006).

SUMMARY

Provided herein are compositions comprising *Methylobacterium* that are depleted of substances that promote growth of resident bacteria on the plant or seed, compositions comprising a solid substance with adherent *Methylobacterium* grown thereon or an emulsion having *Methylobacterium* grown therein, compositions comprising certain *Methylobacterium* strains, methods of using the compositions to improve lettuce production, and methods of making the compositions. Such compositions are in certain instances referred to herein as simply "*Methylobacterium*-containing compositions". In certain embodiments, the *Methylobacterium* in the composition or that is used is strain NLS0020, NLS0066, NLS0017, NLS0065, NLS0089, NLS0042, or NLS0068. In certain embodiments, the *Methylobacterium* in the composition or that is used is *Methylobacterium* is selected from the group consisting of NLS0017 (NRRL B-50931), NLS0020 (NRRL B-50930), NLS0021 (NRRL B-50939), NLS0037 (NRRL B-50941), NLS0038 (NRRL B-50942), NLS0042 (NRRL B-50932), NLS0046 (NRRL B-50929), NLS0062 (NRRL B-50937), NLS0064 (NRRL B-50938), NLS0065 (NRRL B-50935), NLS0066 (NRRL B-50940), NLS0068 (NRRL B-50934), NLS0069 (NRRL B-50936), NLS0089 (NRRL B-50933), and derivatives thereof. In certain embodiments, the *Methylobacterium* in the composition or that is used is a *Methylobacterium* that has at least one gene encoding a protein that is orthologous to a protein having an amino acid sequence of SEQ ID NO: 1-5125. In certain embodiments, the *Methylobacterium* has at least one gene encoding a protein that is orthologous to a reference protein of Table 7. In certain embodiments, the *Methylobacterium* sp. can contain at least one gene encoding a protein that is orthologous to a reference protein having the amino acid sequence of 13, 14, 23, 27, 28, 30, 40, 43, 44, 51, 52, 57, 76, 85, 127, 197, 198, 199, 1094, 1100, 1106, 1114, 1116, 1117, 1120, 1180, 2180, 2190, 2463, 2467, 2468, 2471, 2510, 2515, 2676, 2971, 3357, 3370, 3372, 3394, 3427, 3429, 3430, 3950, 3952, 3968, 3987, 3996, 4004, 4006, and/or 4067 of Table 7. In certain embodiments the *Methylobacterium* has at least one gene encoding a protein that is orthologous to a reference protein is selected from the group consisting of SEQ ID NO: 13, 14, 23, 1094, 1100, 1106, 2467, 2468, 3357, 3370, and/or 3968. In certain embodiments the *Methylobacterium* has at least one gene encoding a protein that is orthologous to a reference protein is selected from the group consisting of SEQ ID NO: 1100, 1116, 2471 and/or 3950. In certain embodiments, the *Methylobacterium* in the composition or that is used is strain NLS0020, NLS0066, NLS0017, NLS0065, or NLS0089 and the composition is used to treat a lettuce seed.

Methods for improving lettuce production comprising applying a coating or partial coating of a composition comprising *Methylobacterium* to a lettuce plant, a part thereof, or to a lettuce seed, wherein said composition comprises: (a) a solid substance with adherent *Methylobacterium* grown thereon; (b) an emulsion having *Methylobacterium* grown therein; (c) certain *Methylobacterium* strains selected from the group consisting of NLS0017 (NRRL B-50931), NLS0020 (NRRL B-50930), NLS0021 (NRRL B-50939), NLS0037 (NRRL B-50941), NLS0038 (NRRL B-50942), NLS0042 (NRRL B-50932), NLS0046 (NRRL B-50929), NLS0062 (NRRL B-50937), NLS0064 (NRRL B-50938), NLS0065 (NRRL B-50935), NLS0066 (NRRL B-50940), NLS0068 (NRRL B-50934), NLS0069 (NRRL B-50936), NLS0089 (NRRL B-50933), and derivatives thereof and an agriculturally acceptable adjuvant, excipient, or combination thereof; or (d) a *Methylobacterium* that has at least one gene encoding at least one protein that is orthologous to a protein having an amino acid sequence of SEQ ID NO: 1-5125 and an agriculturally acceptable adjuvant, excipient, or combination thereof; and wherein said lettuce plant or lettuce plant grown from said seed exhibits a trait improvement selected from the group consisting of an increased rate of leaf growth, an increased rate of root growth, increased total biomass production, increased seed yield, decreased cycle time, and combinations thereof when compared to an untreated control lettuce plant or a control lettuce plant grown from an untreated seed are provided herein. In certain embodiments, the composition comprises *Methylobacterium* at a titer of about $1 \times 10^6$ CFU/gm to about $1 \times 10^{14}$ CFU/gm for a solid composition or at a titer of about $1 \times 10^6$ CFU/mL to about $1 \times 10^{11}$ CFU/mL for a liquid composition containing the solid substance or for the emulsion. In certain embodiments, the *Methylobacterium* has at least one gene encoding at least one protein that is orthologous to a protein having an amino acid sequence of SEQ ID NO: 1-5125. In certain embodiments, the *Methylobacterium* has at least one gene encoding a protein that is orthologous to a reference protein of Table 7. In certain embodiments, the *Methylobacterium* sp. can contain at least one gene encoding a protein that is orthologous to a reference protein having the amino acid sequence of 13, 14, 23, 27, 28, 30, 40, 43, 44, 51, 52, 57, 76, 85, 127, 197, 198, 199, 1094, 1100, 1106, 1114, 1116, 1117, 1120, 1180, 2180, 2190, 2463, 2467, 2468, 2471, 2510, 2515, 2676, 2971, 3357, 3370, 3372, 3394, 3427, 3429, 3430, 3950, 3952, 3968, 3987, 3996, 4004, 4006, and/or 4067 of Table 7. In certain embodiments the *Methylobacterium* has at least one gene encoding a protein that is orthologous to a reference protein is selected from the group consisting of SEQ ID NO: 13, 14, 23, 1094, 1100, 1106, 2467, 2468, 3357, 3370, and/or 3968. In certain embodiments the *Methylobacterium* has at least one gene encoding a protein that is orthologous to a reference protein is selected from the group consisting of SEQ ID NO: 1100, 1116, 2471 and/or 3950. In certain embodiments, the *Methylobacterium* in the composition or that is used is selected from the group consisting of NLS0017 (NRRL B-50931), NLS0020 (NRRL B-50930), NLS0021 (NRRL B-50939), NLS0037 (NRRL B-50941), NLS0038 (NRRL B-50942), NLS0042 (NRRL B-50932), NLS0046 (NRRL B-50929), NLS0062 (NRRL B-50937), NLS0064 (NRRL B-50938), NLS0065 (NRRL B-50935), NLS0066 (NRRL B-50940), NLS0068 (NRRL B-50934), NLS0069 (NRRL B-50936), NLS0089 (NRRL B-50933), and derivatives thereof. In certain embodiments, the *Methylobacterium* in the composition or that is used is selected from the group consisting of NLS0017, NLS0037, NLS0066, NLS0020, NLS0042, NLS0065, NLS0089, NLS0046, NLS0021. NLS0069, NLS0068, NLS0064, NLS0062, NLS0038, and derivatives thereof. In certain embodiments, the *Methylobacterium* has at least one polymorphic DNA element that is present in at least one *Methylobacterium* strain selected from the group consisting of NLS0020, NLS0066, NLS0017, NLS0065, NLS0089, NLS0042, and NLS0068 provided herein that improve lettuce production but that is absent from *Methylobacterium* sp. that do not improve lettuce production. In certain embodiments, the composition is applied to a lettuce seed and the least one polymorphic DNA element is present in at least one *Methylobacterium* strain selected from the group consisting of NLS0020, NLS0066, NLS0017, NLS0065, and NLS0089. In certain embodiments, the composition is applied to a lettuce seed and the *Methylobacterium* is selected from the group consisting of NLS0020, NLS0066, NLS0017, NLS0065, and NLS0089. In certain embodiments, the composition is applied to a lettuce plant or a part thereof and the least one polymorphic DNA element is present in at least one *Methylobacterium* strain selected from the group consisting of NLS0042, NLS0017, NLS0020, and NLS0068. In certain embodiments, the composition is applied to a lettuce plant or a part thereof and the *Methylobacterium* is selected from the group consisting of NLS0042, NLS0017, NLS0020, and NLS0068. In certain embodiments, the applied composition coats or partially coats said plant or a part thereof, or said seed. In certain embodiments, the methods further comprise: (i) growing said lettuce plant or lettuce plant grown from said seed; and/or (ii) harvesting leaves or seed from said lettuce plant or lettuce plant grown from said seed. In certain embodiments, the solid substance with adherent *Methylobacterium* is not a substance that promotes growth of resident microorganisms on the lettuce plant, the part thereof, or the lettuce seed. In certain embodiments, the composition comprises an agriculturally acceptable adjuvant and/or excipient. In certain embodiments of any of the aforementioned methods, the composition is depleted of substances that promote growth of resident microorganisms on said plant or seed. Also provided are lettuce plant parts or lettuce seeds obtained by any of the aforementioned methods and that are coated or partially coated with a composition comprising *Methylobacterium*.

Methods for improving lettuce plant production comprising applying a composition comprising *Methylobacterium* to a lettuce plant, a part thereof, or lettuce seed, wherein said composition is depleted of substances that promote growth of resident microorganisms on said plant or seed and wherein said plant or plant grown from said seed exhibits a trait improvement selected from the group consisting of an increased rate of leaf growth, an increased rate of root growth, increased total biomass production, increased seed yield, decreased cycle time, and combinations thereof when compared to an untreated control lettuce plant or a control lettuce plant grown from an untreated seed. In certain embodiments, the composition comprises a solid substance with adherent *Methylobacterium* grown thereon. In certain embodiments, the solid substance is not a substance that promotes growth of resident microorganisms on the lettuce plant, the part thereof, or the lettuce seed. In certain embodiments, the composition comprises *Methylobacterium* at a titer of about $1 \times 10^6$ CFU/gm to about $1 \times 10^{14}$ CFU/gm. In certain embodiments, the composition comprises a liquid, a solid substance with *Methylobacterium* adhered thereto in a liquid, a solid substance with *Methylobacterium* adhered thereto in an emulsion, or an emulsion. In certain embodiments, the composition comprises *Methylobacterium* at a titer of about $1 \times 10^6$ CFU/mL to about $1 \times 10^{11}$ CFU/mL. In certain embodiments, the methods further comprise: (i) growing said lettuce plant or lettuce plant grown from said seed; and/or (ii) harvesting leaves or seed from said lettuce plant or lettuce plant grown from said seed. In certain embodiments, the *Methylobacterium* has at least one gene encoding at least one protein that is orthologous to a protein having an amino acid sequence of SEQ ID NO: 1-5125. In certain embodiments, the *Methylobacterium* has at least one gene encoding a protein that is orthologous to a reference protein of Table 7. In certain embodiments, the *Methylobacterium* sp. can contain at least one gene encoding a protein that is orthologous to a reference protein having the amino acid sequence of 13, 14, 23, 27, 28, 30, 40, 43, 44, 51, 52, 57, 76, 85, 127, 197, 198, 199, 1094, 1100, 1106, 1114, 1116, 1117, 1120, 1180, 2180, 2190, 2463, 2467, 2468, 2471, 2510, 2515, 2676, 2971, 3357, 3370, 3372, 3394, 3427, 3429, 3430, 3950, 3952, 3968, 3987, 3996, 4004, 4006, and/or 4067 of Table 7. In certain embodiments the *Methylobacterium* has at least one gene encoding a protein that is orthologous to a reference protein is selected from the group consisting of SEQ ID NO: 13, 14, 23, 1094, 1100, 1106, 2467, 2468, 3357, 3370, and/or 3968. In certain embodiments the *Methylobacterium* has at least one gene encoding a protein that is orthologous to a reference protein is selected from the group consisting of SEQ ID NO: 1100, 1116, 2471 and/or 3950. In certain embodiments, the *Methylobacterium* in the composition or that is used is selected from the group consisting of NLS0017 (NRRL B-50931), NLS0020 (NRRL B-50930), NLS0021 (NRRL B-50939), NLS0037 (NRRL B-50941), NLS0038 (NRRL B-50942), NLS0042 (NRRL B-50932), NLS0046 (NRRL B-50929), NLS0062 (NRRL B-50937), NLS0064 (NRRL B-50938), NLS0065 (NRRL B-50935), NLS0066 (NRRL B-50940), NLS0068 (NRRL B-50934), NLS0069 (NRRL B-50936), NLS0089 (NRRL B-50933), and derivatives thereof. In certain embodiments, the *Methylobacterium* in the composition or that is used is selected from the group consisting of NLS0017, NLS0037, NLS0066, NLS0020, NLS0042, NLS0065, NLS0089, NLS0046, NLS0021. NLS0069, NLS0068, NLS0064, NLS0062, NLS0038, and derivatives thereof. In certain embodiments the reference protein is selected from the group consisting of SEQ ID NO: 11000, 1116, 2471 and/or 3950. In certain embodiments, the *Methylobacterium* has at least one polymorphic DNA element that is present in at least one *Methylobacterium* strain selected from the group consisting of NLS0020, NLS0066, NLS0017, NLS0065, NLS0089, NLS0042, and NLS0068 provided herein that improve lettuce production but that is absent from *Methylobacterium* sp. that do not improve lettuce production. In certain embodiments, the composition is applied to a lettuce seed and the least one polymorphic DNA element is present in at least one *Methylobacterium* strain selected from the group consisting of NLS0020, NLS0066, NLS0017, NLS0065, and NLS0089. In certain embodiments, the composition is applied to a lettuce seed and the *Methylobacterium* is selected from the group consisting of NLS0020, NLS0066, NLS0017, NLS0065, and NLS0089. In certain embodiments, the composition is applied to a lettuce plant or a part thereof and the least one polymorphic DNA element is present in at least one *Methylobacterium* strain selected from the group consisting of NLS0042, NLS0017, NLS0020, and NLS0068. In certain embodiments, the composition is applied to a lettuce plant or a part thereof and the *Methylobacterium* is selected from the group consisting of NLS0042, NLS0017, NLS0020, and NLS0068. In certain embodiments of any of the aforementioned methods, the composition coats or partially coats said plant or a part thereof, or said seed. Also provided are lettuce plant parts or lettuce seeds obtained by any of the aforementioned methods and that are coated or partially coated with a composition comprising *Methylobacterium*.

Compositions comprising: (i) a solid substance with adherent *Methylobacterium* grown thereon wherein said *Methylobacterium* has at least one gene encoding a protein that is orthologous to a protein having an amino acid sequence of SEQ ID NO: 1-5125; (ii) an emulsion with *Methylobacterium* grown therein wherein said *Methylobacterium* has at least one gene encoding a protein that is orthologous to a protein having an amino acid sequence of SEQ ID NO: 1-5125; or (iii) certain *Methylobacterium* strains selected from the group consisting of NLS0017 (NRRL B-50931), NLS0020 (NRRL B-50930), NLS0021 (NRRL B-50939), NLS0037 (NRRL B-50941), NLS0038 (NRRL B-50942), NLS0042 (NRRL B-50932), NLS0046 (NRRL B-50929), NLS0062 (NRRL B-50937), NLS0064 (NRRL B-50938), NLS0065 (NRRL B-50935), NLS0066 (NRRL B-50940), NLS0068 (NRRL B-50934), NLS0069 (NRRL B-50936), NLS0089 (NRRL B-50933), and derivatives thereof and an agriculturally acceptable adjuvant, excipient, or combination thereof are provided herein. Also provided herein are compositions comprising: (a) (i) a solid substance with adherent *Methylobacterium* grown thereon; (ii) an emulsion with *Methylobacterium* grown therein; or (iii) a *Methylobacterium* that has at least one gene encoding a protein that is orthologous to a protein having an amino acid sequence of SEQ ID NO: 1-5125; and (b) an agriculturally acceptable excipient, adjuvant, or combination thereof. In certain embodiments, the *Methylobacterium* has at least one gene encoding a protein that is orthologous to a reference protein of Table 7. In certain embodiments, the reference protein is selected from the group consisting of SEQ ID NO: 13, 14, 23, 1094, 1100, 1106, 2467, 2468, 3357, 3370, and/or 3968. In certain embodiments, the *Methylobacterium* is selected from the group consisting of NLS0017 (NRRL B-50931), NLS0020 (NRRL B-50930), NLS0037 (NRRL B-50941), NLS0042 (NRRL B-50932), NLS0065 (NRRL B-50935), NLS0066 (NRRL B-50940), and derivatives thereof. Also provided are compositions comprising: (i) a solid substance with adherent *Methylobacterium* grown thereon; or (ii) an emulsion with *Methylobacterium* grown therein, wherein said *Methylobacterium* has at least one polymorphic DNA element that is present in at least one *Methylobacterium* strain selected from the group consisting of NLS0020, NLS0066, NLS0017, NLS0065, NLS0089, NLS0042, and NLS0068 provided herein that improve lettuce production but that is absent from *Methylobacterium* sp. that do not improve lettuce production. In certain embodiments, the at least one polymorphic DNA element is present in at least one *Methylobacterium* strain selected from the group consisting of NLS0020, NLS0066, NLS0017, NLS0065, and NLS0089. In certain embodiments, the least one polymorphic DNA element is present in at least one *Methylobacterium* strain selected from the group consisting of NLS0042, NLS0017, NLS0020, and NLS0068. In certain embodiments, the *Methylobacterium* is selected from the group consisting of NLS0020, NLS0066, NLS0017, NLS0065, NLS0089, NLS0042, and NLS0068. In certain embodiments, the composition is depleted of substances that promote growth of resident microorganisms on a plant or seed. In certain embodiments, the substance that promotes growth of resident microorganisms on a plant or seed is selected from the group consisting of a carbon source, a nitrogen source, a phosphorous source, a sulfur source, a magnesium source, and combinations thereof. In certain embodiments, the compositions further comprise an agriculturally acceptable adjuvant and/or excipient. In certain embodiments, the solid substance with adherent *Methylobacterium* grown thereon has a *Methylobacterium* titer of at least about $5 \times 10^8$ CFU/gm to at least about $1 \times 10^{14}$ CFU/gm. In certain embodiments, the *Methylobacterium* is selected from the group consisting of NLS0020, NLS0066, NLS0017, NLS0065, and NLS0089. In certain embodiments, the aforementioned compositions are adapted for use in treating a plant or seed or is used to treat a plant or seed. Also provided herein is a lettuce plant part or lettuce seed that is coated or partially coated with any of the aforementioned the compositions. In certain embodiments, the coated or partially coated lettuce plant part or lettuce seed is obtained by any of the aforementioned methods.

Also provided is an isolated *Methylobacterium* selected from the group consisting of NLS0017 (NRRL B-50931), NLS0020 (NRRL B-50930), NLS0021 (NRRL B-50939), NLS0037 (NRRL B-50941), NLS0038 (NRRL B-50942), NLS0042 (NRRL B-50932), NLS0046 (NRRL B-50929), NLS0062 (NRRL B-50937), NLS0064 (NRRL B-50938), NLS0065 (NRRL B-50935), NLS0066 (NRRL B-50940), NLS0068 (NRRL B-50934), NLS0069 (NRRL B-50936), NLS0089 (NRRL B-50933), and derivatives thereof.

Also provided are compositions comprising: (i) an isolated *Methylobacterium* selected from the group consisting of NLS0017 (NRRL B-50931), NLS0020 (NRRL B-50930), NLS0021 (NRRL B-50939), NLS0037 (NRRL B-50941), NLS0038 (NRRL B-50942), NLS0042 (NRRL B-50932), NLS0046 (NRRL B-50929), NLS0062 (NRRL B-50937), NLS0064 (NRRL B-50938), NLS0065 (NRRL B-50935), NLS0066 (NRRL B-50940), NLS0068 (NRRL B-50934), NLS0069 (NRRL B-50936), NLS0089 (NRRL B-50933), derivatives thereof; and (ii) an agriculturally acceptable adjuvant, excipient, or combination thereof.

Also provided are plants, plant parts, and plant seeds that are coated or partially coated with any of the aforementioned compositions. In certain embodiments, a lettuce plant, plant part, or plant seed is coated or partially coated with the aforementioned compositions.

Also provided herein are methods of identifying compositions, plant parts, plant seeds, or processed plant products comprising *Methylobacterium* sp. NLS0017 (NRRL B-50931), NLS0020 (NRRL B-50930), NLS0037 (NRRL B-50941), NLS0042 (NRRL B-50932), NLS0065 (NRRL B-50935), or NLS0066 (NRRL B-50940) by assaying for the presence of nucleic acid sequences contained in SEQ ID NO: 5126-10250 in those materials. In certain embodiments, such methods can comprise subjecting a sample suspected of containing *Methylobacterium* sp. NLS0017 (NRRL B-50931), NLS0020 (NRRL B-50930), NLS0037 (NRRL B-50941), NLS0042 (NRRL B-50932), NLS0065 (NRRL B-50935), or NLS0066 (NRRL B-50940) to a nucleic acid analysis technique and determining that the sample contains one or more nucleic acid containing a sequence of at least about 20, 50, 100, 200, 500, or a 1000 nucleotides that is identical to at least one of SEQ ID NO: 5126-10250, wherein the presence of a sequence that is identical to at least one of SEQ ID NO: 5126-6211 is indicative of the presence of NLS017, wherein the presence of a sequence that is identical to at least one of SEQ ID NO: 6212-7301 is indicative of the presence of NLS020, wherein the presence of a sequence that is identical to at least one of SEQ ID NO: 7302-7586 is indicative of the presence of NLS037, wherein the presence of a sequence that is identical to at least one of SEQ ID NO: 7587-8472 is indicative of the presence of NLS042, wherein the presence of a sequence that is identical to at least one of SEQ ID NO: 8473-9074 is indicative of the presence of NLS065, and wherein the presence of a sequence that is identical to at least one of SEQ ID NO: 9075-10250 is indicative of the presence of NLS066. Such nucleic acid analyses include, but are not limited to, techniques based on nucleic acid hybridization, polymerase chain reactions, mass spectroscopy, nanopore based detection, branched DNA analyses, combinations thereof, and the like.

Also provided herein are methods of identifying *Methylobacterium* sp. that can confer useful traits to plants by assaying for the presence of nucleic acid sequences contained in SEQ ID NO: 5126-10250 in the *Methylobacterium* sp. In certain embodiments, such methods can comprise subjecting a candidate *Methylobacterium* sp. to a nucleic acid analysis technique and determining that the sample contains one or more nucleic acid containing a sequence of at least about 20, 50, 100, 200, 500, or a 1000 nucleotides that is identical to at least one of SEQ ID NO: 5126-10250 indicates that the candidate *Methylobacterium* sp. that can confer a useful traits to a plant. Such nucleic acid analyses include, but are not limited to, techniques based on nucleic acid hybridization, polymerase chain reactions, mass spectroscopy, nanopore based detection, branched DNA analyses, combinations thereof, and the like.

DESCRIPTION

Definitions

As used herein, the phrases "adhered thereto" and "adherent" refer to *Methylobacterium* that are associated with a solid substance by growing, or having been grown, on a solid substance.

As used herein, the phrase "agriculturally acceptable adjuvant" refers to a substance that enhances the performance of an active agent in a composition for treatment of plants and/or plant parts. In certain compositions, an active agent can comprise a mono-culture or co-culture of *Methylobacterium*.

As used herein, the phrase "agriculturally acceptable excipient" refers to an essentially inert substance that can be used as a diluent and/or carrier for an active agent in a composition for treatment of plants and/or plant parts. In certain compositions, an active agent can comprise a mono-culture or co-culture of *Methylobacterium*.

As used herein, the term "*Methylobacterium*" refers to bacteria that are facultative methylotrophs of the genus *Methylobacterium*. The term *Methylobacterium*, as used herein, thus does not encompass includes species in the genera *Methylobacter, Methylomonas, Methylomicrobium, Methylococcus, Methylosinus, Methylocystis, Methylosphaera, Methylocaldum,* and *Methylocella*, which are obligate methanotrophs.

As used herein, the phrase "co-culture of *Methylobacterium*" refers to a *Methylobacterium* culture comprising at least two strains of *Methylobacterium* or at least two species of *Methylobacterium*.

As used herein, the phrase "contaminating microorganism" refers to microorganisms in a culture, fermentation broth, fermentation broth product, or composition that were not identified prior to introduction into the culture, fermentation broth, fermentation broth product, or composition.

As used herein, the phrase "derivatives thereof", when used in the context of a *Methylobacterium* isolate, refers to any strain that is obtained from the *Methylobacterium* isolate. Derivatives of a *Methylobacterium* isolate include, but are not limited to, variants of the strain obtained by selection, variants of the strain selected by mutagenesis and selection, and a genetically transformed strain obtained from the *Methylobacterium* isolate.

As used herein, the term "emulsion" refers to a colloidal mixture of two immiscible liquids wherein one liquid is the continuous phase and the other liquid is the dispersed phase. In certain embodiments, the continuous phase is an aqueous liquid and the dispersed phase is liquid that is not miscible, or partially miscible, in the aqueous liquid.

As used herein, the phrase "essentially free of contaminating microorganisms" refers to a culture, fermentation broth, fermentation product, or composition where at least about 95% of the microorganisms present by amount or type in the culture, fermentation broth, fermentation product, or composition are the desired *Methylobacterium* or other desired microorganisms of pre-determined identity.

As used herein, the phrase "inanimate solid substance" refers to a substance which is insoluble or partially soluble in water or aqueous solutions and which is either non-living or which is not a part of a still-living organism from which it was derived.

As used herein, the phrase "mono-culture of *Methylobacterium*" refers to a *Methylobacterium* culture consisting of a single strain of *Methylobacterium*.

As used herein, the term "peptide" refers to any polypeptide of 50 amino acid residues or less.

As used herein, the term "lettuce" refers to *Lactuca* sp. plants. *Lactuca* sp. plants include, but are not limited to, *Lactuca biennis, Lactuca canadensis, Lactuca floridana, Lactuca graminifolia, Lactuca hirsuta, Lactuca indica, Lactuca ludoviciana, Lactuca saligna, Lactuca sativa, Lactuca serriola, Lactuca terse-novae, Lactuca virosa,* and *Lactuca* X *morssii* species.

As used herein, the term "protein" refers to any polypeptide having 51 or more amino acid residues.

As used herein, a "pesticide" refers to an agent that is insecticidal, fungicidal, nematocidal, bacteriocidal, or any combination thereof.

As used herein, the phrase "bacteriostatic agent" refers to agents that inhibit growth of bacteria but do not kill the bacteria.

As used herein, the phrase "pesticide does not substantially inhibit growth of said *Methylobacterium*" refers to any pesticide that when provided in a composition comprising a fermentation product comprising a solid substance wherein a mono-culture or co-culture of *Methylobacterium* is adhered thereto, results in no more than a 50% inhibition of *Methylobacterium* growth when the composition is applied to a plant or plant part in comparison to a composition lacking the pesticide. In certain embodiments, the pesticide results in no more than a 40%, 20%, 10%, 5%, or 1% inhibition of *Methylobacterium* growth when the composition is applied to a plant or plant part in comparison to a composition lacking the pesticide.

As used herein, the term "PPFM bacteria" refers without limitation to bacterial species in the genus *Methylobacterium* other than *M. nodulans*.

As used herein, the phrase "solid substance" refers to a substance which is insoluble or partially soluble in water or aqueous solutions.

As used herein, the phrase "solid phase that can be suspended therein" refers to a solid substance that can be distributed throughout a liquid by agitation.

As used herein, the term "non-regenerable" refers to either a plant part or processed plant product that cannot be regenerated into a whole plant.

As used herein, the phrase "substantially all of the solid phase is suspended in the liquid phase" refers to media wherein at least 95%, 98%, or 99% of solid substance(s) comprising the solid phase are distributed throughout the liquid by agitation.

As used herein, the phrase "substantially all of the solid phase is not suspended in the liquid phase" refers to media where less than 5%, 2%, or 1% of the solid is in a particulate form that is distributed throughout the media by agitation.

As used herein, the phrase "resident microorganism" refers to resident bacteria, fungi or yeast.

As used herein, the phrase "substance that promotes growth of resident microorganisms on a plant or seed" refers to a carbon source, a nitrogen source, a phosphorous source, and combinations thereof.

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

*Methylobacterium*-Containing Compositions Depleted of Substances that Promote Growth of Resident Bacteria on a Plant or Seed, Methods of their Use, and Methods of Making Compositions comprising *Methylobacterium* that are depleted of substances that promote growth of resident bacteria on a plant or seed, methods of using the compositions to improve lettuce production, and methods of making the compositions are provided herein. In certain embodiments of any of the aforementioned compositions, the composition comprises a solid substance wherein a mono-culture or co-culture of *Methylobacterium* is adhered thereto. In certain embodiments where the *Methylobacterium* is adhered to a solid substance, the composition comprises a colloid formed by the solid substance wherein a mono-culture or co-culture of *Methylobacterium* is adhered thereto and a liquid. In certain embodiments, the colloid is a gel. In certain embodiments of certain aforementioned compositions, composition is an emulsion that does not contain a solid substance.

Compositions that comprise a solid substance with adherent *Methylobacterium* grown thereon is provided. In certain embodiments, the adherent *Methylobacterium* can be at a titer of at least about $5 \times 10^8$ CFU/gm to at least about $5 \times 10^{13}$ CFU/gm or about $1 \times 10^{14}$ CFU/gm and the composition is depleted of substances that promote growth of resident microorganisms on a plant or seed.

In certain embodiments, the compositions containing *Methylobacterium* provided or used herein are depleted of substances that promote growth of the resident microorganisms when one or more of those substances are absent or are essentially absent. In certain embodiments, the composition is depleted of substances that promote growth of the resident microorganisms when those substances are present at a percentage of no more than about 5%, 2%, 1%, 0.5%, 0.2%, or 0.1% of the total mass, mass/total volume, or total volume of the composition. In certain embodiments, substance that promotes growth of resident microorganisms on a plant or seed is selected from the group consisting of a carbon source, a nitrogen source, a phosphorous source, a sulfur source, a magnesium source, and combinations thereof. Carbon sources include, but are not limited to, alcohols, monosaccharides, disaccharides, polysaccharides, lipids, fatty acids, and the like. Alcohols that are depleted include, but are not limited to, methanol, ethanol, glycerol, and the like. Nitrogen sources include, but are not limited to, ammonia and various compounds containing amino groups that can be metabolized by microorganisms. In certain embodiments, the substance that is depleted is a source of two or more of a carbon source, a nitrogen source, a phosphorous source, a sulfur source, and a magnesium source. For example, the composition that is depleted of amino acids or peptides and lacks other carbon or nitrogen sources is depleted for both a carbon and a nitrogen source. In certain embodiments, the composition comprises an agriculturally acceptable adjuvant and/or excipient.

Resident microorganisms on the plant or seed include, but are not limited to bacteria, fungi, and yeast. Substances that promote the growth of such microorganisms can be identified by methods including, but not limited to, assaying the plant or seed surface for the amount or number of microorganisms present prior to exposure of the plant or seed to the substance (or to a composition containing the substance), exposing the assayed plant or seed to the substance or composition in parallel with a control composition lacking the substance, and then re-assaying the plant or seed surface for the amount or number of microorganisms present after a suitable time interval and under suitable conditions of temperature to allow growth of the resident microorganisms. Assays for numbers of microorganisms include, but are not limited to, determinations of colony forming units per an amount of plant or seed exposed to the substance and the control.

Without seeking to be limited by theory, it is believed that the compositions containing *Methylobacterium* provided or used herein that are depleted of substances that promote growth of the resident microorganisms can result in superior results in comparison to other compositions containing such substances when applied to plants, plant parts, or seeds. Such superior results are believed to include, but are not limited to, improved plant yield, pathogen resistance, insect resistance, fruit ripening and the like. While not seeking to be limited by theory, it is believed that the compositions containing *Methylobacterium* that are depleted of substances that promote growth of the resident microorganisms allow for more efficient and or extensive colonization of the plant, part thereof, or seed as competition for one or more of space or nutrients by the resident microorganisms is reduced.

Also provided herein are methods for improving lettuce production that comprise applying any of the aforementioned compositions or *Methylobacterium* provided herein to a lettuce plant, lettuce plant part, or lettuce seed, and, optionally, growing the plant and/or harvesting leaves or seed from the plant or a plant grown from the seed. In certain embodiments, the composition coats or partially coats the lettuce plant, plant part, or seed. The treated lettuce plant or plant grown from the seed exhibits an increased rate of root growth, an increased rate of leaf growth, increased seed production, a decreased cycle time (from seed planting to seed production) and/or increased total biomass compared to an untreated control lettuce plant or control lettuce plant grown from untreated seed, thereby obtaining improved lettuce production. In certain embodiments, application of the composition provides for at least about a 5%, 10%, 15%, 20%, 30% or 40% increase in root growth rate, leaf growth rate, seed production, and/or increased total biomass in the lettuce plant, lettuce plant part, or a lettuce plant derived therefrom in comparison to an untreated control lettuce plant or control lettuce plant grown from an untreated seed. In certain embodiments, application of the composition provides for about a 5% or 10% to about a 15%, 20%, 25%, 30%, 35%, 40%, 45%, 50%, 60%, or 70% increase in root growth rate, leaf growth rate, seed production, and/or increased total biomass in the plant, plant part, or a plant derived therefrom in comparison to an untreated control lettuce plant or control lettuce plant grown from an untreated seed. In certain embodiments, application of the composition provides for at least about a 5%, 10%, 15%, 20%, 30% or 40% decrease in cycle time in the treated lettuce plant or a lettuce plant grown from a treated seed in comparison to the untreated control lettuce plant or control lettuce plant grown from an un-treated seed. In certain embodiments, application of the composition provides for about a 5% or 10% to about a 15%, 20%, 25%, 30%, 35%, 40%, 45%, or 50% decrease in cycle time in the treated lettuce plant or a lettuce plant grown from a treated seed in comparison to an untreated control lettuce plant or control lettuce plant grown from an untreated seed. In certain embodiments, the lettuce plant part is a leaf, a stem, a flower, a root, a tuber, or a seed. In certain embodiments, the method further comprises the steps of growing the plant and/or the step of harvesting at least one plant part selected from the group consisting of a leaf, a stem, a flower, a root, a tuber, or a seed from the lettuce plant or plant part. In certain embodiments of any of the aforementioned methods, the methods further comprise obtaining a processed food or feed composition from the plant or plant part. In certain embodiments, the processed food composition comprises chopped or cut lettuce leaves.

Also provided are methods of making a lettuce plant or plant seed treatment composition that comprises *Methylobacterium* and is depleted of substances that promote growth of resident bacteria on a plant or seed is provided herein. Such method comprises (i) growing a mono-culture or co-culture of *Methylobacterium* in media that comprises an aqueous phase, a liquid phase and a solid phase, or an emulsion, thereby obtaining a *Methylobacterium*-containing media; (ii) separating the *Methylobacterium* from at least one other portion of the *Methylobacterium*-containing media; and (iii) reconstituting the *Methylobacterium* in a matrix lacking substances that promote growth of resident bacteria on a plant or seed. In certain embodiments, the separation step is effected by centrifugation, filtration, or settling of the *Methylobacterium*-containing media and removal of excess liquid or emulsion therefrom. In certain embodiments, the substance that promotes growth of resident bacteria on a plant or seed is selected from the group consisting of a carbon source, a nitrogen source, a phosphorous source, and combinations thereof. In certain embodiments, the matrix is a liquid, an emulsion, or one or more solids, and comprises an agriculturally acceptable adjuvant and/or excipient. Still in certain embodiments; the *Methylobacterium* are grown in media comprising a liquid phase and a solid substance with adherent *Methylobacterium* grown thereon. The solid substance is separated from the liquid phase of the *Methylobacterium*-containing media, and the solid substance with adherent *Methylobacterium* grown thereon is reconstituted in the aforementioned matrix. In certain embodiments of the methods, the *Methylobacterium* sp., is selected from the group consisting of *M. aminovorans, M. extorquens, M. fujisawaense, M. mesophilicum, M. radiotolerans, M rhodesianum, M. nodulans, M. phyllosphaerae, M. thiocyanatum*, and *M. oryzae*. In certain embodiments of the methods, the *Methylobacterium* is not *M. radiotolerans* or *M. oryzae*. In certain embodiments of the methods, the *Methylobacterium* is adhered to a solid substance. In certain embodiments of the methods, the *Methylobacterium* is adhered to the solid substance is combined with a liquid to form a composition that is a colloid. In certain embodiments of the methods, the colloid is a gel. In certain embodiments of the methods, the *Methylobacterium* adhered to the solid substance is provided by culturing the *Methylobacterium* in the presence of the solid substance. In certain embodiments of the methods, the composition comprises an emulsion. In certain embodiments of the methods, the *Methylobacterium* is provided by culturing the *Methylobacterium* in an emulsion.

Methods where *Methylobacterium* are cultured in biphasic media comprising a liquid phase and a solid substance have been found to significantly increase the resultant yield of *Methylobacterium* relative to methods where the *Methylobacterium* are cultured in liquid media alone. In certain embodiments, the methods can comprise growing the *Methylobacterium* in liquid media with a particulate solid substance that can be suspended in the liquid by agitation under conditions that provide for *Methylobacterium* growth. In certain embodiments where particulate solid substances are used, at least substantially all of the solid phase can thus be suspended in the liquid phase upon agitation. Such particulate solid substances can comprise materials that are about 1 millimeter or less in length or diameter. In certain embodiments, the degree of agitation is sufficient to provide for uniform distribution of the particulate solid substance in the liquid phase and/or optimal levels of culture aeration. However, in other embodiments provided herein, at least substantially all of the solid phase is not suspended in the liquid phase, or portions of the solid phase are suspended in the liquid phase and portions of the solid phase are not suspended in the liquid phase. Non-particulate solid substances can be used in certain biphasic media where the solid phase is not suspended in the liquid phase. Such non-particulate solid substances include, but are not limited to, materials that are greater than about 1 millimeter in length or diameter. Such particulate and non-particulate solid substances also include, but are not limited to, materials that are porous, fibrous, or otherwise configured to provide for increased surface areas for adherent growth of the *Methylobacterium*. Biphasic media where portions of the solid phase are suspended in the liquid phase and portions of the solid phase are not suspended in the liquid phase can comprise a mixture of particulate and non-particulate solid substances. Such particulate and non-particulate solid substances used in any of the aforementioned biphasic media also include, but are not limited to, materials that are porous, fibrous, or otherwise configured to provide for increased surface areas for adherent growth of the *Methylobacterium*. In certain embodiments, the media comprises a colloid formed by a solid and a liquid phase. A colloid comprising a solid and a liquid can be pre-formed and added to liquid media or can be formed in media containing a solid and a liquid. Colloids comprising a solid and a liquid can be formed by subjecting certain solid substances to a chemical and/or thermal change. In certain embodiments, the colloid is a gel. In certain embodiments, the liquid phase of the media is an emulsion. In certain embodiments, the emulsion comprises an aqueous liquid and a liquid that is not miscible, or only partially miscible, in the aqueous liquid. Liquids that are not miscible, or only partially miscible, in water include, but are not limited to, any of the following: (1) liquids having a miscibility in water that is equal to or less than that of pentanol, hexanol, or heptanol at 25 degrees C.; (2) liquids comprising an alcohol, an aldehyde, a ketone, a fatty acid, a phospholipid, or any combination thereof; (3) alcohols selected from the group consisting of aliphatic alcohols containing at least 5 carbons and sterols; (4) an animal oil, microbial oil, synthetic oil, plant oil, or combination thereof; and/or, (5) a plant oil is selected from the group consisting of corn, soybean, cotton, peanut, sunflower, olive, flax, coconut, palm, rapeseed, sesame seed, safflower, and combinations thereof. In certain embodiments, the immiscible or partially immiscible liquid can comprises at least about 0.02% to about 20% of the liquid phase by mass. In certain embodiments, the methods can comprise obtaining a biphasic culture media comprising the liquid, the solid, and *Methylobacterium* and incubating the culture under conditions that provide for growth of the *Methylobacterium*. Biphasic culture medias comprising the liquid, the solid, and *Methylobacterium* can be obtained by a variety of methods that include, but are not limited to, any of: (a) inoculating a biphasic media comprising the liquid and the solid substance with *Methylobacterium*; (b) inoculating the solid substance with *Methylobacterium* and then introducing the solid substance comprising the *Methylobacterium* into the liquid media; (c) inoculating the solid substance with *Methylobacterium*, incubating the *Methylobacterium* on the solid substance, and then introducing the solid substance comprising the *Methylobacterium* into the liquid media; or (d) any combination of (a), (b), or (c). Methods and compositions for growing *Methylobacterium* in biphasic media comprising a liquid and a solid are disclosed in co-assigned U.S. patent application Ser. No. 13/907,161, filed May 31, 2013, which is incorporated herein by reference in its entirety, and in co-assigned International Patent Application PCT/US13/43722, filed May 31, 2013, which is incorporated herein by reference in its entirety.

Methods where *Methylobacterium* are cultured in media comprising an emulsion have also been found to significantly increase the resultant yield of *Methylobacterium* relative to methods where the *Methylobacterium* are cultured in liquid media alone. In certain embodiments, the methods for making the compositions provided herein can comprise growing the *Methylobacterium* agent in an emulsion under conditions that provide for *Methylobacterium* growth. Medias comprising the emulsion and *Methylobacterium* can be obtained by a variety of methods that include, but are not limited to, any of: (a) inoculating a media comprising the emulsion with *Methylobacterium*; (b) inoculating the aqueous liquid with the *Methylobacterium*, introducing the non-aqueous liquid, and mixing to form an emulsion; (c) inoculating the aqueous liquid with the *Methylobacterium*, introducing the non-aqueous liquid, and mixing to form an emulsion; or (d) any combination of (a), (b), or (c). In certain embodiments, the emulsion comprises an aqueous liquid and a liquid that is not miscible, or only partially miscible, in the aqueous liquid. Non-aqueous liquids that are not miscible, or only partially miscible, in water include, but are not limited to, any of the following: (1) liquids having a miscibility in water that is equal to or less than that of n-pentanol, n-hexanol, or n-heptanol at 25 degrees C.; (2) liquids comprising an alcohol, an aldehyde, a ketone, a fatty acid, a phospholipid, or any combination thereof; (3) alcohols is selected from the group consisting of aliphatic alcohols containing at least 5, 6, or 7 carbons and sterols; (4) an animal oil, microbial oil, synthetic oil, plant oil, or combination thereof; and/or, (5) a plant oil is selected from the group consisting of corn, soybean, cotton, peanut, sunflower, olive, flax, coconut, palm, rapeseed, sesame seed, safflower, and combinations thereof. In certain embodiments, the immiscible or partially immiscible non-aqueous liquid can comprise at least about 0.02% to about 20% of the emulsion by mass. In certain embodiments, the immiscible or partially immiscible non-aqueous liquid can comprise at least about any of about 0.05%, 0.1%, 0.5%, or 1% to about 3%, 5%, 10%, or 20% of the emulsion by mass. Methods and compositions for growing *Methylobacterium* in media comprising an emulsion are disclosed in co-assigned International Patent Application PCT/US2014/040218, filed May 30, 2014, which is incorporated herein by reference in its entirety.

In certain embodiments, the fermentation broth, fermentation broth product, or compositions that comprise *Methylobacterium* sp. can further comprise one or more introduced microorganisms of pre-determined identity other than *Methylobacterium*. Other microorganisms that can be added include, but are not limited to, microorganisms that are biopesticidal or provide some other benefit when applied to a plant or plant part. Biopesticidal or otherwise beneficial microorganisms thus include, but are not limited to, various *Bacillus* sp., *Pseudomonas* sp., *Coniothyrium* sp., *Pantoea* sp., *Streptomyces* sp., and *Trichoderma* sp. Microbial biopesticides can be a bacterium, fungus, virus, or protozoan. Particularly useful biopesticidal microorganisms include various *Bacillus subtilis, Bacillus thuringiensis, Bacillus pumilis, Pseudomonas syringae, Trichoderma harzianum, Trichoderma* vixens, and *Streptomyces lydicus* strains. Other microorganisms that are added can be genetically engineered or naturally occurring isolates that are available as pure cultures. In certain embodiments, it is anticipated that the bacterial or fungal microorganism can be provided in the fermentation broth, fermentation broth product, or composition in the form of a spore.

In certain embodiments, the liquid culture medium is prepared from inexpensive and readily available components, including, but not limited to, inorganic salts such as potassium phosphate, magnesium sulfate and the like, carbon sources such as glycerol, methanol, glutamic acid, aspartic acid, succinic acid and the like, and amino acid blends such as peptone, tryptone, and the like. Exemplary liquid media that can be used include, but are not limited to, ammonium mineral salts (AMS) medium (Whittenbury et al., 1970), Vogel-Bonner (VB) minimal culture medium (Vogel and Bonner, 1956), and LB broth ("Luria—Bertani Broth").

In general, the solid substance used in the methods and compositions that provide for the efficient growth of *Methylobacterium* can be any suitable solid substance which is insoluble or only partially soluble in water or aqueous solutions. Such suitable solid substances are also non-bacteriocidal or non-bacteriostatic with respect to *Methylobacterium* when the solid substances are provided in the liquid culture media. In certain embodiments, such suitable solid substances are also solid substances that are readily obtained in sterile form or rendered sterile. Solid substances used herein can be sterilized by any method that provides for removal of contaminating microorganisms and thus include, but are not limited to, methods such as autoclaving, irradiation, chemical treatment, and any combination thereof. These solid substances include natural substances of animal, plant, microbial, fungal, or mineral origin, manmade substances, or combinations of natural and manmade substances. In certain embodiments, the solid substances are inanimate solid substances. Inanimate solid substances of animal, plant, microbial, or fungal origin can be obtained from animals, plants, microbes, or fungi that are unviable (i.e. no longer living) or that have been rendered unviable. Diatom shells are thus inanimate solid substances when previously associated diatom algae have been removed or otherwise rendered inviable. Since diatom shells are inanimate solid substances, they are not considered to be photosynthetic organisms or photosynthetic microorganisms. In certain embodiments, solid substances include, but are not limited to, sand, silt, soil, clay, ash, charcoal, diatomaceous earth and other similar minerals, ground glass or glass beads, ground ceramic materials, ceramic beads, bentonite, kaolin, talc, perlite, mica, vermiculite, silicas, quartz powder, montmorillonite, and combinations thereof. In certain embodiments, the solid substance can be a polymer or polymeric beads. Polymers that can be used as a solid substance include, but are not limited to, various polysaccharides such as cellulosic polymers and chitinous polymers which are insoluble or only partially soluble in water or aqueous solutions, agar (i.e. galactans), and combinations thereof. In certain embodiments, the solid substance can be an insoluble or only partially soluble salt crystal. Salt crystals that can be used include, but are not limited to, insoluble or only partially soluble carbonates, chromates, sulfites, phosphates, hydroxides, oxides, and sulfides. In certain embodiments, the solid substance can be a microbial cell, fungal cell, microbial spore, or fungal spore. In certain embodiments, the solid substance can be a microbial cell or microbial spore wherein the microbial cell or microbial spore is not a photosynthetic microorganism. In certain embodiments, the microbial cell or microbial spore is not a photosynthetic microorganism, where the photosynthetic microorganism is selected from the group consisting of algae, cyanobacteria, diatoms, *Botryococcus braunii, Chlorella, Dunaliella tertiolecta, Gracilaria, Pleurochrysis camerae, Sargassum,* and *Ulva*. In still other embodiments, the solid substance can be an inactivated (i.e., unviable) microbial cell, fungal cell, microbial spore, or fungal spore. In still other embodiments, the solid substance can be a quiescent (i.e. viable but not actively dividing) microbial cell, fungal cell, microbial spore, or fungal spore. In still other embodiments, the solid substance can be cellular debris of microbial origin. In still other embodiments, the solid substance can be particulate matter from any part of a plant. Plant parts that can be used to obtain the solid substance include, but are not limited to, cobs, husks, hulls, leaves, roots, flowers, stems, barks, seeds, and combinations thereof. Products obtained from processed plant parts including, but not limited to, bagasse, wheat bran, soy grits, crushed seed cake, stover, and the like can also be used. Such plant parts, processed plants, and/or processed plant parts can be milled to obtain the solid material in a particulate form that can be used. In certain embodiments, wood or a wood product including, but not limited to, wood pulp, sawdust, shavings, and the like can be used. In certain embodiments, the solid substance can be a particulate matter from an animal(s), including, but not limited to, bone meal, gelatin, ground or powdered shells, hair, macerated hide, and the like.

In certain embodiments, the solid substance is provided in a particulate form that provides for distribution of the solid substance in the culture media. In certain embodiments, the solid substance is comprised of particle of about 2 microns to about 1000 microns in average length or average diameter. In certain embodiments, the solid substance is comprised of particle of about 1 microns to about 1000 microns in average length or average diameter. In certain embodiments, the solid substance is a particle of about 1, 2, 4, 10, 20, or 40 microns to any of about 100, 200, 500, 750, or 1000 microns in average length or average diameter. Desirable characteristics of particles used in the methods and compositions provided herein include suitable wettability such that the particles can be suspended throughout the media upon agitation.

In certain embodiments, the solid substance is provided in the media as a colloid wherein the continuous phase is a liquid and the dispersed phase is the solid. Suitable solids that can be used to form colloids in liquid media used to grow *Methylobacterium* include, but are not limited to, various solids that are referred to as hydrocolloids. Such hydrocolloids used in the media, methods and compositions provided herein can be hydrophilic polymers, of plant, animal, microbial, or synthetic origin. Hydrocolloid polymers used in the methods can contain many hydroxyl groups and/or can be polyelectrolytes. Hydrocolloid polymers used in the compositions and methods provided herein include, but are not limited to, agar, alginate, arabinoxylan, carrageenan, carboxymethylcellulose, cellulose, curdlan, gelatin, gellan, β-glucan, guar gum, gum arabic, locust bean gum, pectin, starch, xanthan gum, and mixtures thereof. In certain embodiments, the colloid used in the media, methods, and compositions provided herein can comprise a hydrocolloid polymer and one or more proteins.

In certain embodiments, the solid substance can be a solid substance that provides for adherent growth of *Methylobacterium* on the solid substance. *Methylobacterium* that are adhered to a solid substance are *Methylobacterium* that cannot be substantially removed by simply washing the solid substance with the adherent *Methylobacterium* with growth media whereas non-adherent *Methylobacterium* can be substantially removed by washing the solid substance with liquid growth media. In this context, "substantially removed" means that at least about 30%, 40%, 50%, 60%, 70%, or 80% the *Methylobacterium* present are removed when the solid substance is washed with three volumes of liquid growth media. Such washing can be effected by a variety of methods including, but not limited to, decanting liquid from a washed solid phase or passing liquid through a solid phase on a filter that permits flow through of bacteria in the liquid. In certain embodiments, the adherent *Methylobacterium* that are associated with the solid can include both *Methylobacterium* that are directly attached to the solid and/or *Methylobacterium* that are indirectly attached to the solid substance. *Methylobacterium* that are indirectly attached to the solid substance include, but are not limited to, *Methylobacterium* that are attached to another *Methylobacterium* or to another microorganism that is attached to the solid substance, *Methylobacterium* that are attached to the solid substance by being attached to another substance that is attached to the solid substance, and the like. In certain embodiments, at least 10%, 20%, 30%, 40%, 50%, 60%, 70%, 80%, 90%, 95%, 98%, 99%, 99.5% or 99.9% of the *Methylobacterium* in the fermentation broth, fermentation broth product, or compositions are *Methylobacterium* that are adhered to the solid substance. In certain embodiments, adherent *Methylobacterium* can be present on the surface of the solid substance in the fermentation broth, fermentation broth product, or composition at a density of at least about 1 *Methylobacterium*/20 square micrometers, of at least about 1 *Methylobacterium*/10 square micrometers, of at least about 1 *Methylobacterium*/10 square micrometers, of at least about 1 *Methylobacterium*/5 square micrometers, of at least about 1 *Methylobacterium*/2 square micrometers, or of at least about 1 *Methylobacterium*/square micrometer. In certain embodiments, adherent *Methylobacterium* can be present on the surface of the solid substance in the fermentation broth, fermentation broth product, or composition at a density of at least about 1 *Methylobacterium*/20 square micrometers to about 1 *Methylobacterium*/square micrometer, of at least about 1 *Methylobacterium*/10 square micrometers to about 1 *Methylobacterium*/square micrometer, of at least about 1 *Methylobacterium*/10 square micrometers to about 1 *Methylobacterium*/square micrometer, of at least about 1 *Methylobacterium*/5 square micrometers to about 1 *Methylobacterium*/square micrometer, or of at least about 1 *Methylobacterium*/2 square micrometers to about 1 *Methylobacterium*/square micrometer. In certain embodiments, adherent *Methylobacterium* can be present on the surface of the solid substance in the fermentation broth, fermentation broth product, or composition at a density of at least about 1 *Methylobacterium*/20 square micrometers to about 1 *Methylobacterium*/2 square micrometers, of at least about 1 *Methylobacterium*/10 square micrometers to about 1 *Methylobacterium*/2 square micrometers, of at least about 1 *Methylobacterium*/10 square micrometers to about 1 *Methylobacterium*/2 square micrometers, or of at least about 1 *Methylobacterium*/5 square micrometers to about 1 *Methylobacterium*/2 square micrometers. Biphasic fermentation broths provided herein can comprise a liquid phase that contains non-adherent *Methylobacterium*. In certain embodiments, titers of non-adherent *Methylobacterium* in the liquid phase can be less than about 100,000, 10,000, or 1,000 CFU/ml.

Biphasic culture methods provided can yield fermentation broths with *Methylobacterium* at a titer of greater than about $5 \times 10^8$ colony-forming units per milliliter, at a titer of greater than about $1 \times 10^9$ colony-forming units per milliliter, at a titer of greater than about $1 \times 10^{10}$ colony-forming units per milliliter, at a titer of at least about $3 \times 10^{10}$ colony-forming units per milliliter. In certain embodiments, fermentation broths provided herein can comprise *Methylobacterium* at a titer of at least about $5 \times 10^8$ colony-forming units per milliliter to at least about $3 \times 10^{10}$ colony-forming units per milliliter, at least about $5 \times 10^8$ colony-forming units per milliliter to at least about $4 \times 10^{10}$ colony-forming units per milliliter, or at least about $5 \times 10^8$ colony-forming units per milliliter to at least about $6 \times 10^{10}$ colony-forming units per milliliter. In certain embodiments, fermentation broths provided herein can comprise *Methylobacterium* at a titer of at least about $1 \times 10^9$ colony-forming units per milliliter to at least about $3 \times 10^{10}$ colony-forming units per milliliter, at least about $1 \times 10^9$ colony-forming units per milliliter to at least about $4 \times 10^{10}$ colony-forming units per milliliter, or at least about $1 \times 10^9$ colony-forming units per milliliter to at least about $6 \times 10^{10}$ colony-forming units per milliliter. In certain embodiments, fermentation broths provided herein will comprise *Methylobacterium* at a titer of at least about $1 \times 10^{10}$ colony-forming units per milliliter to at least about $3 \times 10^{10}$ colony-forming units per milliliter, at least about $1 \times 10^{10}$ colony-forming units per milliliter to at least about $4 \times 10^{10}$ colony-forming units per milliliter, or at least about $1 \times 10^{10}$ colony-forming units per milliliter to at least about $6 \times 10^{10}$ colony-forming units per milliliter. In certain embodiments, fermentation broths provided herein will comprise *Methylobacterium* at a titer of, at least about $3 \times 10^{10}$ colony-forming units per milliliter to at least about $4 \times 10^{10}$ colony-forming units per milliliter, or at least about $3 \times 10^{10}$ colony-forming units per milliliter to at least about $6 \times 10^{10}$ colony-forming units per milliliter.

Solid substances with adherent *Methylobacterium* can be obtained as fermentation products can be used to make various compositions useful for treating plants or plant parts to improve plant yield, plant insect resistance, plant fungal disease resistance, and/or to improve lettuce production. In certain embodiments, the composition comprises *Methylobacterium* and is depleted of substances that promote growth of resident bacteria. Compositions provided herein comprising *Methylobacterium*, solid substances with *Methylobacterium* grown thereon, or comprising emulsions with *Methylobacterium* grown therein can be used to treat plants or plant parts. Plants, plant parts, and, in particular, plant seeds that have been at least partially coated or coated with the fermentation broth products or compositions comprising *Methylobacterium* are thus provided. Also provided are processed plant products that contain the fermentation broth products or compositions with *Methylobacterium* or adherent *Methylobacterium*. Solid substances with adherent *Methylobacterium* can be used to make various compositions that are particularly useful for treating plant seeds. Seeds that have been at least partially coated with the fermentation broth products or compositions are thus provided. Also provided are processed seed products, including, but not limited to, meal, flour, feed, and flakes that contain the fermentation broth products or compositions provided herein. In certain embodiments, the processed plant product will be non-regenerable (i.e. will be incapable of developing into a plant). In certain embodiments, the solid substance used in the fermentation product or composition that at least partially coats the plant, plant part, or plant seed or that is contained in the processed plant, plant part, or seed product comprises a solid substance and associated or adherent *Methylobacterium* that can be readily identified by comparing a treated and an untreated plant, plant part, plant seed, or processed product thereof. Partial coating of a plant, a plant part, or a seed includes, but is not limited to coating at least about 5%, 10%, 20%, 30%, 40%, 50%, 60%, 70%, 80%, 90%, 95%, 98%, 99%, or about 99.5% of the surface area of the plant, plant part, or plant seed.

Methods of preparing a plant or plant seed treatment composition that comprises *Methylobacterium* and is depleted of substances that promote growth of resident bacteria on a plant or seed are also provided herein. Such methods can comprise (i) growing a mono-culture or co-culture of *Methylobacterium* in media that comprises: (a) an aqueous phase; (b) a liquid phase and a solid phase; or (c) an emulsion, thereby obtaining a *Methylobacterium*-containing media; (ii) separating the *Methylobacterium* from at least one other portion of the *Methylobacterium*-containing media; and (iii) reconstituting the *Methylobacterium* in a matrix lacking substances that promote growth of resident bacteria on a plant or seed. In certain embodiments, the separation step is effected by centrifugation, filtration, or settling of the *Methylobacterium*-containing media and removal of excess liquid or emulsion therefrom. In certain embodiments where the *Methylobacterium* are grown in the presence of a solid substance, the separation will provide a fraction containing *Methylobacterium* with adherent growth to the solid substance and some non-adherent *Methylobacterium* that can be reconstituted in the matrix. In certain embodiments, the substance that promotes growth of resident bacteria on a plant or seed is selected from the group consisting of a carbon source, a nitrogen source, a phosphorous source, a sulfur source, a magnesium source, and combinations thereof. In certain embodiments, the matrix is a liquid, an emulsion, or one or more solids, and comprises an agriculturally acceptable adjuvant and/or excipient. In certain embodiments; the *Methylobacterium* are grown in media comprising a liquid phase and a solid substance with adherent *Methylobacterium* grown thereon. The solid substance is separated from the liquid phase of the *Methylobacterium*-containing media, and the solid substance with adherent *Methylobacterium* grown thereon is reconstituted in the aforementioned matrix. In certain embodiments, the matrix can be a liquid including, but not limited to, water, and aqueous buffer depleted of substances that promote growth of resident bacteria on a plant or seed, or an aqueous solution depleted of substances that promote growth of resident bacteria on a plant or seed.

In certain embodiments, the *Methylobacterium* sp. that improve lettuce production can be identified by testing newly isolated candidate *Methylobacterium* sp. for the presence of polymorphic nucleic acid sequences that are present in exemplary *Methylobacterium* sp. provided herein that improve lettuce production and that are absent from *Methylobacterium* sp. provided herein that do not improve lettuce production. In certain embodiments, the polymorphic nucleic acid sequences that are present in the identified *Methylobacterium* sp. that improve lettuce production are also present in one or more of the exemplary *Methylobacterium* sp. isolates NLS0020, NLS0066, NLS0017, NLS0065, NLS0089, NLS0042, and NLS0068 provided herein that improve lettuce production but are absent from one or more of the *Methylobacterium* sp. isolates provided herein that do not improve lettuce production. In certain embodiments, the polymorphic nucleic acid sequences that are present in the identified *Methylobacterium* sp. that improve lettuce production are also present in one or more of the exemplary *Methylobacterium* sp. isolates NLS0020, NLS0066, NLS0017, NLS0065 and/or NLS0089 provided herein that improve lettuce production when applied as seed treatments but are absent from one or more of the *Methylobacterium* sp. isolates provided herein that do not improve lettuce production when applied as seed treatments. In certain embodiments, the polymorphic nucleic acid sequences that are present in the identified *Methylobacterium* sp. that improve lettuce production are also present in one or more of the exemplary *Methylobacterium* sp. isolates NLS0020, NLS0017, NLS0042, and NLS0068 provided herein that improve lettuce production when applied as foliar treatments but are absent from one or more of the *Methylobacterium* sp. isolates provided herein that do not improve lettuce production when applied as foliar treatments. In certain embodiments, the polymorphic nucleic acid sequences that are present in the identified *Methylobacterium* sp. that improve lettuce production are also present in two or more of the exemplary *Methylobacterium* sp. isolates NLS0020, NLS0066, NLS0017, NLS0065, NLS0089, NLS0042, and NLS0068 provided herein that improve lettuce production but are absent in two or more of the *Methylobacterium* sp. isolates provided herein that do not improve lettuce production. In certain embodiments, the polymorphic nucleic acid sequences that are present in the identified *Methylobacterium* sp. that improve lettuce production are also present in one or more of the exemplary *Methylobacterium* sp. isolates NLS0020, NLS0066, NLS0017, NLS0065, NLS0089, NLS0042, and/or NLS0068 provided herein that improve lettuce production but are absent from all of the *Methylobacterium* sp. isolates provided herein that do not improve lettuce production. In certain embodiments, the polymorphic nucleic acid sequences present in the identified *Methylobacterium* sp. that improve lettuce production are present in all of the exemplary *Methylobacterium* sp. isolates NLS0020, NLS0066, NLS0017, NLS0065, NLS0089, NLS0042, and NLS0068 provided herein that improve lettuce production but are absent in all of the *Methylobacterium* sp. isolates provided herein that do not improve lettuce production. Such nucleic acid polymorphisms that occur in the *Methylobacterium* sp. that improve lettuce production can include, but are not limited to, single nucleotide polymorphisms, RFLP, AFLP and/or other DNA variations such as repetitive sequences, insertion sequences, transposons, and genomic islands occurring as a result of insertions, deletions, and substitutions (Indels) in the bacterial genome which includes both the chromosomal DNA as well as any extrachromosomal nucleic acid elements that may be present in the *Methylobacterium* sp. that improve lettuce production. Such extrachromosomal nucleic acid elements include, but are not limited to, plasmids, bacteriophage DNA or RNA, and the like. Methods used to identify such nucleotide polymorphisms include, but are not limited to, single base extension (SBE) techniques, allele specific hybridization (ASH), real-time PCR detection (i.e. TaqMan™; U.S. Pat. Nos. 5,804, 375; 5,538,848; 5,487,972; and 5,210,015, which are each incorporated herein by reference in their entireties), combinations of ASH and RT-PCR (KASP™ detection systems, LGC Genomics, Middlesex, UK) and deep sequencing techniques (U.S. Patent Appl. No. 20120264632, incorporated herein by reference in its entirety).

Also provided herein are compositions, methods of making the compositions, and methods of using the compositions to improve lettuce production where the compositions or methods comprise or use any of the following *Methylobacterium* sp. isolates provided in the following Table 1 or derivatives of the isolates. In certain embodiments, such derivatives can include variants but are not limited to, variants of the isolates obtained by selection, variants of the isolates selected by mutagenesis and selection, and genetically transformed isolates obtained from the isolates.

TABLE 1

*Methylobacterium* sp. isolates

| NLS | USDA ARS NRRL No.[1] |
|---|---|
| NLS0017 | NRRL B-50931 |
| NLS0020 | NRRL B-50930 |
| NLS0021 | NRRL B-50939 |
| NLS0037 | NRRL B-50941 |
| NLS0038 | NRRL B-50942 |
| NLS0042 | NRRL B-50932 |
| NLS0046 | NRRL B-50929 |
| NLS0062 | NRRL B-50937 |
| NLS0064 | NRRL B-50938 |
| NLS0065 | NRRL B-50935 |
| NLS0066 | NRRL B-50940 |
| NLS0068 | NRRL B-50934 |
| NLS0069 | NRRL B-50936 |
| NLS0089 | NRRL B-50933 |

[1]Deposit number for strain to be deposited with the AGRICULTURAL RESEARCH SERVICE CULTURE COLLECTION (NRRL) of the National Center for Agricultural Utilization Research, Agricultural Research Service, U.S. Department of Agriculture, 1815 North University Street, Peoria, Illinois 61604 U.S.A. under the terms of the Budapest Treaty on the International Recognition of the Deposit of Microorganisms for the Purposes of Patent Procedure. Subject to 37 CFR §1.808(b), all restrictions imposed by the depositor on the availability to the public of the deposited material will be irrevocably removed upon the granting of any patent from this patent application.

Co-assigned patent applications that disclose additional specific uses of the *Methylobacterium* strains of Table 1 such as: (1) increasing corn yield (U.S. 61/911,780, filed Dec. 4, 2013; and International Application claiming benefit of the same filed on Dec. 4, 2014); (2) increasing soybean yield (U.S. 61/911,698, filed Dec. 4, 2013; and International Application claiming benefit of the same filed on Dec. 4, 2014); (3) improving tomato growth (U.S. 61/954,390, filed Mar. 17, 2014; and International Application claiming benefit of the same filed on Dec. 4, 2014); (4) improving fruit maturation (U.S. 61/911,577, filed Dec. 4, 2013; and International Application claiming benefit of the same filed on Dec. 4, 2014); (5) providing fungal disease resistance (U.S. 62/045,950, filed Sep. 4, 2014; U.S. 62/013,464, filed Jun. 17, 2014) and are each incorporated herein by reference in their entireties. Specifically incorporated herein by reference in their entireties are the amino acid and genomic nucleic acid sequences of NLS017 and NLS066 disclosed in the International Application for Compositions And Methods For Improved Tomato Growth, filed Dec. 4, 2014 and claiming benefit of U.S. 61/954,390, filed Mar. 17, 2014.

Also provided herein are *Methylobacterium* sp. that provide for improved lettuce production where the *Methylobacterium* sp. have any of: (i) at least one gene encoding at least one protein that is orthologous to a protein having an amino acid sequence of SEQ ID NO: 1-5125; or (ii) at least one gene encoding at least one protein that is orthologous to a reference protein of Table 7. A *Methylobacterium* sp. has at least one gene that is orthologous to a protein having an amino acid sequence of at least one of SEQ ID NO: 1-5125, or to the corresponding SEQ ID NO of a reference protein of Table 7, when a chromosome and/or any extrachromosomal DNA in that *Methylobacterium* sp. contains a gene encoding a protein that has at least 50%, at least 60%, at least 70%, at least 80%, at least 90%, at least 95%, at least 97%, at least 98%, at least 99%, or 100% sequence identity across the entire length of the amino acid sequence of at least one of SEQ ID NO: 1-5125. The *Methylobacterium* sp. can also have at least two, three, four, six, eight, 10, 15, or 20 genes encoding proteins that are orthologous to proteins having an amino acid sequence of SEQ ID NO: 1-5125 or encoding proteins that are orthologous to the corresponding SEQ ID NO of a reference protein of Table 7. In certain embodiments, the *Methylobacterium* sp. can contain at least one gene encoding a protein that is orthologous to a reference protein having the amino acid sequence of 13, 14, 23, 27, 28, 30, 40, 43, 44, 51, 52, 57, 76, 85, 127, 197, 198, 199, 1094, 1100, 1106, 1114, 1116, 1117, 1120, 1180, 2180, 2190, 2463, 2467, 2468, 2471, 2510, 2515, 2676, 2971, 3357, 3370, 3372, 3394, 3427, 3429, 3430, 3950, 3952, 3968, 3987, 3996, 4004, 4006, and/or 4067 of Table 7. In certain embodiments, the *Methylobacterium* sp. can contain at least one gene encoding a protein that is orthologous to reference protein having the amino acid sequence of SEQ ID NO: 13, 14, 23, 1094, 1100, 1106, 2467, 2468, 3357, 3370, and/or 3968 of Table 7. In certain embodiments, the *Methylobacterium* sp. can contain at least one gene encoding a protein that is orthologous to reference protein having the amino acid sequence of SEQ ID NO: 1100, 1116, 2471, 2971, and/or 3950 of Table 7. Examples of proteins that are orthologous to SEQ ID NO: 1094 include, but are not limited to, the orthologous proteins identified as transcriptional regulators that are provided in Table 7. Examples of proteins that are orthologous to SEQ ID NO: 23 include, but are not limited to, the orthologous proteins identified as transcriptional regulator XRE family proteins that are provided in Table 7. Examples of proteins that are orthologous to SEQ ID NO: 1100 include, but are not limited to, proteins having the amino acid sequence of SEQ ID NO: 17, 1110, 2179, 2484, and 3367 that are similar to proteins identified as ABC transporter-like proteins. Examples of proteins that are orthologous to SEQ ID NO: 1116 include, but are not limited to, proteins having the amino acid sequence of SEQ ID NO: 37, 1116, 2182, and 2521 that are similar to proteins identified as multidrug transporter MatE. Examples of proteins that are orthologous to SEQ ID NO: 2471 include, but are not limited to, proteins having the amino acid sequence of SEQ ID NO: 10, 2471, 3356, and 3958 that are similar to proteins identified as arsenite efflux pump ACR proteins. Examples of proteins that are orthologous to SEQ ID NO: 2971 include, but are not limited to, proteins having the amino acid sequence of SEQ ID NO: 250, 1309, 2263, and 2971 that are similar to proteins identified as members of the LysR family transcriptional regulators. In certain embodiments, the *Methylobacterium* sp. has at least one gene that is orthologous to a protein having an amino acid sequence of at least one of SEQ ID NO: 1-5125, or to the corresponding SEQ ID NO of a reference protein of Table 7, with the proviso that the gene is not found in *M. extorquens* AM1, *M. extorquens* PA1, or *M. extorquens* ME4. Compositions comprising any of the aforementioned *Methylobacterium* sp. and an agriculturally acceptable excipient, adjuvant, or combination thereof are also provided along with lettuce seeds or leaves that are at least partially coated with such compositions and methods of using such compositions as seed or foliar treatments to improve lettuce production.

A *Methylobacterium* sp. can be determined to contain a gene encoding a protein that is orthologous to a protein having an amino acid sequence of SEQ ID NO: 1-5125 by a variety of different techniques. In certain embodiments, a *Methylobacterium* sp. can be determined to contain a gene encoding a protein that is orthologous to a protein having an amino acid sequence of SEQ ID NO: 1-5125 by assembling a complete electronic genomic sequence comprising chromosomal and extrachromosomal DNA sequences present in that *Methylobacterium* sp. with a computer and associated software, and determining if any of the open reading frames (ORF) present in that DNA sequence encode a protein having the aforementioned percent sequence identity. In such embodiments, the ORF can be identified by performing a six-way translation of the electronically assembled sequence and querying the translated with an amino acid sequence of SEQ ID NO: 1-5125 or the corresponding SEQ ID NO: of a reference protein of Table 7. In other embodiments, the present or absence of a given sequence within a *Methylobacterium* sp. an amino acid sequence of SEQ ID NO: 1-5125 or the corresponding SEQ ID NO: of a reference protein of Table 7 can be determined by a nucleic acid analysis or protein analysis technique. Examples of nucleic acid sequences that encode the proteins of SEQ ID NO:1-5125 include, but are not limited to, SEQ ID NO: 5126-10250, respectively. Such nucleic acid analyses include, but are not limited to, techniques based on nucleic acid hybridization, polymerase chain reactions, mass spectroscopy, nanopore based detection, combinations thereof, and the like. Protein analysis techniques include, but are not limited to, immuno-detection, mass spectroscopy, combinations thereof, and the like.

Compositions provided herein that are useful for treating lettuce plants or plant parts that comprise *Methylobacterium*, and/or are depleted of substances that promote growth of resident bacteria on a plant or seed, contain a solid substance with adherent *Methylobacterium* grown thereon, or that comprise emulsions with *Methylobacterium* grown therein can also further comprise an agriculturally acceptable adjuvant or an agriculturally acceptable excipient. An agriculturally acceptable adjuvant or an agriculturally acceptable excipient is typically an ingredient that does not cause undue phytotoxicity or other adverse effects when exposed to a plant or plant part. In certain embodiments, the solid substance can itself be an agriculturally acceptable adjuvant or an agriculturally acceptable excipient so long as it is not bacteriocidal or bacteriostatic to the *Methylobacterium*. In other embodiments, the composition further comprises at least one of an agriculturally acceptable adjuvant or an agriculturally acceptable excipient. Any of the aforementioned compositions can also further comprise a pesticide. Pesticides used in the composition include, but are not limited to, an insecticide, a fungicide, a nematocide, and a bacteriocide. In certain embodiments, the pesticide used in the composition is a pesticide that does not substantially inhibit growth of the *Methylobacterium*. As *Methylobacterium* are gram negative bacteria, suitable bacteriocides used in the compositions can include, but are not limited to, bacteriocides that exhibit activity against gram positive bacteria but not gram negative bacteria. Compositions provided herein can also comprise a bacteriostatic agent that does not substantially inhibit growth of the *Methylobacterium*. Bacteriostatic agents suitable for use in compositions provided herein include, but are not limited to, those that exhibit activity against gram positive bacteria but not gram negative bacteria. Any of the aforementioned compositions can also be an essentially dry product (i.e. having about 5% or less water content), a mixture of the composition with an emulsion, or a suspension. Any of the compositions provided herein can be used to coat or partially coat a plant, plant, part, or plant seed. Partial coating of a plant, a plant part, or a seed includes, but is not limited to coating at least about 5%, 10%, 20%, 30%, 40%, 50%, 60%, 70%, 80%, 90%, 95%, 98%, 99%, or about 99.5% of the surface area of the plant, plant part, or plant seed.

Agriculturally acceptable adjuvants used in the compositions that comprise *Methylobacterium* include, but are not limited to, components that enhance product efficacy and/or products that enhance ease of product application. Adjuvants that enhance product efficacy can include various wetters/spreaders that promote adhesion to and spreading of the composition on plant parts, stickers that promote adhesion to the plant part, penetrants that can promote contact of the active agent with interior tissues, extenders that increase the half-life of the active agent by inhibiting environmental degradation, and humectants that increase the density or drying time of sprayed compositions. Wetters/spreaders used in the compositions can include, but are not limited to, non-ionic surfactants, anionic surfactants, cationic surfactants, amphoteric surfactants, organo-silicate surfactants, and/or acidified surfactants. Stickers used in the compositions can include, but are not limited to, latex-based substances, terpene/pinolene, and pyrrolidone-based substances. Penetrants can include mineral oil, vegetable oil, esterified vegetable oil, organo-silicate surfactants, and acidified surfactants. Extenders used in the compositions can include, but are not limited to, ammonium sulphate, or menthene-based substances. Humectants used in the compositions can include, but are not limited to, glycerol, propylene glycol, and diethyl glycol. Adjuvants that improve ease of product application include, but are not limited to, acidifying/buffering agents, anti-foaming/de-foaming agents, compatibility agents, drift-reducing agents, dyes, and water conditioners. Anti-foaming/de-foaming agents used in the compositions can include, but are not limited to, dimethopolysiloxane. Compatibility agents used in the compositions can include, but are not limited to, ammonium sulphate. Drift-reducing agents used in the compositions can include, but are not limited to, polyacrylamides, and polysaccharides. Water conditioners used in the compositions can include, but are not limited to, ammonium sulphate.

Methods of treating plants and/or plant parts with the fermentation broths, fermentation broth products, and compositions comprising *Methylobacterium* are also provided herein. Treated plants, and treated plant parts obtained therefrom, include, but are not limited to, a pepper, tomato, berry, or banana plant. Plant parts that are treated include, but are not limited to, leaves, stems, flowers, roots, seeds, fruit, tubers, coleoptiles, and the like. Seeds or other propagules of any of the aforementioned plants can be treated with the fermentation broths, fermentation broth products, fermentation products, and/or compositions provided herein.

In certain embodiments, plants and/or plant parts are treated by applying the fermentation broths, fermentation broth products, fermentation products, and compositions that comprise *Methylobacterium* as a spray. Such spray applications include, but are not limited to, treatments of a single plant part or any combination of plant parts. Spraying can be achieved with any device that will distribute the fermentation broths, fermentation broth products, fermentation products, and compositions to the plant and/or plant part(s). Useful spray devices include a boom sprayer, a hand or backpack sprayer, crop dusters (i.e. aerial spraying), and the like. Spraying devices and or methods providing for application of the fermentation broths, fermentation broth products, fermentation products, and compositions to either one or both of the adaxial surface and/or abaxial surface can also be used. Plants and/or plant parts that are at least partially coated with any of a biphasic fermentation broth, a fermentation broth product, fermentation product, or compositions that comprise a solid substance with *Methylobacterium* adhered thereto are also provided herein. Also provided herein are processed plant products that comprise a solid substance with *Methylobacterium* adhered thereto. Any of the compositions provided herein can be used to coat or partially coat a plant, plant, part, or plant seed. Partial coating of a plant, a plant part, or a seed includes, but is not limited to coating at least about 5%, 10%, 20%, 30%, 40%, 50%, 60%, 70%, 80%, 90%, 95%, 98%, 99%, or about 99.5% of the surface area of the plant, plant part, or plant seed In certain embodiments, lettuce seeds are treated by exposing the seeds to the fermentation broths, fermentation broth products, fermentation products, and compositions that comprise *Methylobacterium*. Seeds can be treated with the fermentation broths, fermentation broth products, and compositions provided herein by methods including, but not limited to, imbibition, coating, spraying, and the like. In certain embodiments, surface sterilized seeds are treated with a composition comprising *Methylobacterium*. In certain embodiments, non-sterilized seeds (i.e. seeds that have not been subjected to surface sterilization) are treated with a composition comprising *Methylobacterium* that has been depleted of substances that promote growth of resident microorganisms on the seed. Seed treatments can be effected with both continuous and/or a batch seed treaters. In certain embodiments, the coated seeds may be prepared by slurrying seeds with a coating composition containing a fermentation broth, fermentation broth product, or compositions that comprise the solid substance with *Methylobacterium* and air drying the resulting product. Air drying can be accomplished at any temperature that is not deleterious to the seed or the *Methylobacterium*, but will typically not be greater than 30 degrees Centigrade. The proportion of coating that comprises a solid substance and *Methylobacterium* includes, but is not limited to, a range of 0.1 to 25% by weight of the seed, 0.5 to 5% by weight of the seed, and 0.5 to 2.5% by weight of seed. Partial coating of a seed can includes, but is not limited to coating at least about 5%, 10%, 20%, 30%, 40%, 50%, 60%, 70%, 80%, 90%, 95%, 98%, 99%, or about 99.5% of the surface area of the seed. In certain embodiments, a solid substance used in the seed coating or treatment will have *Methylobacterium* adhered thereon. In certain embodiments, a solid substance used in the seed coating or treatment will be associated with *Methylobacterium* and will be a fermentation broth, fermentation broth product, or composition obtained by the methods provided herein. Various seed treatment compositions and methods for seed treatment disclosed in U.S. Pat. Nos. 5,106,648, 5,512,069, and 8,181,388 are incorporated herein by reference in their entireties and can be adapted for use with an active agent comprising the fermentation broths, fermentation broth products, or compositions provided herein. In certain embodiments, the composition used to treat the seed can contain agriculturally acceptable excipients that include, but are not limited to, woodflours, clays, activated carbon, diatomaceous earth, fine-grain inorganic solids, calcium carbonate and the like. Clays and inorganic solids that can be used with the fermentation broths, fermentation broth products, or compositions provided herein include, but are not limited to, calcium bentonite, kaolin, china clay, talc, perlite, mica, vermiculite, silicas, quartz powder, montmorillonite and mixtures thereof. Agriculturally acceptable adjuvants that promote sticking to the seed that can be used include, but are not limited to, polyvinyl acetates, polyvinyl acetate copolymers, hydrolyzed polyvinyl acetates, polyvinylpyrrolidone-vinyl acetate copolymer, polyvinyl alcohols, polyvinyl alcohol copolymers, polyvinyl methyl ether, polyvinyl methyl ether-maleic anhydride copolymer, waxes, latex polymers, celluloses including ethylcelluloses and methylcelluloses, hydroxy methylcelluloses, hydroxypropylcellulose, hydroxymethylpropylcelluloses, polyvinyl pyrrolidones, alginates, dextrins, maltodextrins, polysaccharides, fats, oils, proteins, karaya gum, jaguar gum, tragacanth gum, polysaccharide gums, mucilage, gum arabics, shellacs, vinylidene chloride polymers and copolymers, soybean-based protein polymers and copolymers, lignosulfonates, acrylic copolymers, starches, polyvinylacrylates, zeins, gelatin, carboxymethylcellulose, chitosan, polyethylene oxide, acrylamide polymers and copolymers, polyhydroxyethyl acrylate, methylacrylamide monomers, alginate, ethylcellulose, polychloroprene and syrups or mixtures thereof. Other useful agriculturally acceptable adjuvants that can promote coating include, but are not limited to, polymers and copolymers of vinyl acetate, polyvinylpyrrolidone-vinyl acetate copolymer and water-soluble waxes. Various surfactants, dispersants, anticaking-agents, foam-control agents, and dyes disclosed herein and in U.S. Pat. No. 8,181,388 can be adapted for use with an active agent comprising the fermentation broths, fermentation broth products, or compositions provided herein.

Provided herein are compositions that comprise *Methylobacterium* that provide improved lettuce production relative to untreated plants that have not been exposed to the compositions. In certain embodiments, plant parts, including, but not limited to, a seed, a leaf, a fruit, a stem, a root, a tuber, or a coleoptile can be treated with the compositions provided herein to improve lettuce production. Treatments or applications can include, but are not limited to, spraying, coating, partially coating, immersing, and/or imbibing the plant or plant parts with the compositions provided herein. In certain embodiments, a seed, a leaf, a fruit, a stem, a root, a tuber, or a coleoptile can be immersed and/or imbibed with a liquid, semi-liquid, emulsion, or slurry of a composition provided herein. Such seed immersion or imbibition can be sufficient to provide for improved lettuce production in a treated plant or plant part in comparison to an untreated plant or plant part. Improved lettuce production includes, but is not limited, to increased root growth, increased leaf growth, increased seed production, and/or increased total biomass relative to untreated plants. In certain embodiments, plant seeds can be immersed and/or imbibed for at least 1, 2, 3, 4, 5, or 6 hours. Such immersion and/or imbibition can, in certain embodiments, be conducted at temperatures that are not deleterious to the plant seed or the *Methylobacterium*. In certain embodiments, the seeds can be treated at about 15 to about 30 degrees Centigrade or at about 20 to about 25 degrees Centigrade. In certain embodiments, seed imbibition and/or immersion can be performed with gentle agitation.

Compositions provided herein comprising *Methylobacterium* are therefore expected to be useful in improving lettuce production.

In certain embodiments, an amount of a composition provided herein that is sufficient to provide for improved lettuce production can be a composition with *Methylobacterium* at a titer of at least about $1 \times 10^6$ colony-forming units per milliliter, at least about $5 \times 10^6$ colony-forming units per milliliter, at least about $1 \times 10^7$ colony-forming units per milliliter, at least about $5 \times 10^8$ colony-forming units per milliliter, at least about $1 \times 10^9$ colony-forming units per milliliter, at least about $1 \times 10^{10}$ colony-forming units per milliliter, or at least about $3 \times 10^{10}$ colony-forming units per milliliter. In certain embodiments, an amount of a composition provided herein that is sufficient to provide for improving lettuce production can be a composition with *Methylobacterium* at a titer of about least about $1 \times 10^6$ colony-forming units per milliliter, at least about $5\times10^6$ colony-forming units per milliliter, at least about $1\times10^7$ colony-forming units per milliliter, or at least about $5\times10^8$ colony-forming units per milliliter to at least about $6\times10^{10}$ colony-forming units per milliliter of a liquid or an emulsion. In certain embodiments, an amount of a composition provided herein that is sufficient to provide for improving lettuce production can be a fermentation broth product with a *Methylobacterium* titer of a solid phase of that product is at least about $5\times10^8$ colony-forming units per milliliter to at least about $5\times10^{13}$ colony-forming units of *Methylobacterium* per gram of the solid phase. In certain embodiments, an amount of a composition provided herein that is sufficient to provide for improving lettuce production can be a composition with a *Methylobacterium* titer of at least about $1\times10^6$ colony-forming units per gram, at least about $5\times10^6$ colony-forming units per gram, at least about $1\times10^7$ colony-forming units per gram, or at least about $5\times10^8$ colony-forming units per gram to at least about $6\times10^{10}$ colony-forming units of *Methylobacterium* per gram of particles in the composition containing the particles that comprise a solid substance wherein a mono-culture or co-culture of *Methylobacterium* is adhered thereto. In certain embodiments, an amount of a composition provided herein that is sufficient to provide for improving lettuce production can be a composition with a *Methylobacterium* titer of at least about $1\times10^6$ colony-forming units per mL, at least about $5\times10^6$ colony-forming units per mL, at least about $1\times10^7$ colony-forming units per mL, or at least about $5\times10^8$ colony-forming units per ml, to at least about $6\times10^{10}$ colony-forming units of *Methylobacterium* per mL in a composition comprising an emulsion wherein a mono-culture or co-culture of a *Methylobacterium* adhered to a solid substance is provided therein or grown therein. In certain embodiments, an amount of a composition provided herein that is sufficient to provide for improving lettuce production can be a composition with a *Methylobacterium* titer of at least about $1\times10^6$ colony-forming units per mL, at least about $5\times10^6$ colony-forming units per mL, at least about $1\times10^7$ colony-forming units per mL, or at least about $5\times10^8$ colony-forming units per mL to at least about $6\times10^{10}$ colony-forming units of *Methylobacterium* per mL of in a composition comprising an emulsion wherein a mono-culture or co-culture of a *Methylobacterium* is provided therein or grown therein.

In certain embodiments, an amount of a composition provided herein that is sufficient to provide for improved lettuce production can be a composition with a *Methylobacterium* sp. at a titer of at least about $1\times10^4$ colony-forming units per milliliter, at least about $1\times10^5$ colony-forming units per milliliter, at least about $1\times10^6$ colony-forming units per milliliter, at least about $5\times10^6$ colony-forming units per milliliter, at least about $1\times10^7$ colony-forming units per milliliter, at least about $5\times10^8$ colony-forming units per milliliter, at least about $1\times10^9$ colony-forming units per milliliter, at least about $1\times10^{10}$ colony-forming units per milliliter, or at least about $3\times10^{10}$ colony-forming units per milliliter. In certain embodiments, an amount of a composition provided herein that is sufficient to provide for improved lettuce production can be a composition with *Methylobacterium* sp. at a titer of at least about $1\times10^4$ colony-forming units per milliliter, at least about $1\times10^5$ colony-forming units per milliliter, about least about $1\times10^6$ colony-forming units per milliliter, at least about $5\times10^6$ colony-forming units per milliliter, at least about $1\times10^7$ colony-forming units per milliliter, or at least about $5\times10^8$ colony-forming units per milliliter to at least about $6\times10^{10}$ colony-forming units per milliliter of a liquid or an emulsion. In certain embodiments, an amount of a composition provided herein that is sufficient to provide for improved lettuce production can be a fermentation broth product with a *Methylobacterium* sp. titer of a solid phase of that product is at least about $1\times10^4$ colony-forming units per gram, at least about $1\times10^5$ colony-forming units per gram, at least about $1\times10^6$ colony-forming units per gram, at least about $5\times10^6$ colony-forming units per gram, at least about $1\times10^7$ colony-forming units per gram, at least about $5\times10^8$ colony-forming units per gram, at least about $1\times10^9$ colony-forming units per gram, or at least about $5\times10^9$ colony-forming units per gram to at least about $6\times10^{10}$ colony-forming units of *Methylobacterium* per gram, at least about $1\times10^{11}$ colony-forming units of *Methylobacterium* per gram, at least about $1\times10^{12}$ colony-forming units of *Methylobacterium* per gram, at least about $1\times10^{13}$ colony-forming units of *Methylobacterium* per gram, or at least about $5\times10^{13}$ colony-forming units of *Methylobacterium* per gram of the solid phase. In certain embodiments, an amount of a composition provided herein that is sufficient to provide for improved lettuce production can be a composition with a *Methylobacterium* titer of at least about $1\times10^6$ colony-forming units per gram, at least about $5\times10^6$ colony-forming units per gram, at least about $1\times10^7$ colony-forming units per gram, at least about $5\times10^8$ colony-forming units per gram, at least about $1\times10^9$ colony-forming units per gram, or at least about $5\times10^9$ colony-forming units per gram to at least about $6\times10^{10}$ colony-forming units of *Methylobacterium* per gram, at least about $1\times10^{11}$ colony-forming units of *Methylobacterium* per gram, at least about $1\times10^{12}$ colony-forming units of *Methylobacterium* per gram, at least about $1\times10^{13}$ colony-forming units of *Methylobacterium* per gram, or at least about $5\times10^{13}$ colony-forming units of *Methylobacterium* per gram of particles in the composition containing the particles that comprise a solid substance wherein a mono-culture or co-culture of *Methylobacterium* sp. is adhered thereto. In certain embodiments, an amount of a composition provided herein that is sufficient to provide for improved lettuce production can be a composition with a *Methylobacterium* titer of at least about $1\times10^6$ colony-forming units per mL, at least about $5\times10^6$ colony-forming units per mL, at least about $1\times10^7$ colony-forming units per mL, or at least about $5\times10^8$ colony-forming units per mL to at least about $6\times10^{10}$ colony-forming units of *Methylobacterium* per mL in a composition comprising an emulsion wherein a mono-culture or co-culture of a *Methylobacterium* sp. adhered to a solid substance is provided therein or grown therein. In certain embodiments, an amount of a composition provided herein that is sufficient to provide for improved lettuce production can be a composition with a *Methylobacterium* titer of at least about $1\times10^6$ colony-forming units per mL, at least about $5\times10^6$ colony-forming units per mL, at least about $1\times10^7$ colony-forming units per mL, or at least about $5\times10^8$ colony-forming units per mL to at least about $6\times10^{10}$ colony-forming units of *Methylobacterium* per mL of in a composition comprising an emulsion wherein a mono-culture or co-culture of a *Methylobacterium* sp. is provided therein or grown therein.

In certain embodiments, compositions with a *Methylobacterium* sp. at a titer of at least about $1\times10^4$ colony-forming units per milliliter, at least about $1\times10^5$ colony-forming units per milliliter, at least about $1\times10^6$ colony-forming units per milliliter, at least about $5\times10^6$ colony-forming units per milliliter, at least about $1\times10^7$ colony-forming units per milliliter, at least about $5\times10^8$ colony-forming units per milliliter, at least about $1\times10^9$ colony-forming units per milliliter, at least about $1\times10^{10}$ colony-forming units per milliliter, or at least about $3\times10^{10}$ colony-forming units per milliliter are provided or used. In certain embodiments, compositions with *Methylobacterium* sp. at a titer of at least about $1\times10^4$ colony-forming units per milliliter, at least about $1\times10^5$ colony-forming units per milliliter, about least about $1\times10^6$ colony-forming units per milliliter, at least about $5\times10^6$ colony-forming units per milliliter, at least about $1\times10^7$ colony-forming units per milliliter, or at least about $5\times10^8$ colony-forming units per milliliter to at least about $6\times10^{10}$ colony-forming units per milliliter of a liquid or an emulsion are provided. In certain embodiments, fermentation broth products with a *Methylobacterium* sp. titer of a solid phase of that product is at least about $1\times10^4$ colony-forming units per gram, at least about $1\times10^5$ colony-forming units per gram, at least about $1\times10^6$ colony-forming units per gram, at least about $5\times10^6$ colony-forming units per gram, at least about $1\times10^7$ colony-forming units per gram, at least about $5\times10^8$ colony-forming units per gram, at least about $1\times10^9$ colony-forming units per gram, or at least about $5\times10^9$ colony-forming units per gram to at least about $6\times10^{10}$ colony-forming units of *Methylobacterium* per gram, at least about $1\times10^{11}$ colony-forming units of *Methylobacterium* per gram, at least about $1\times10^{12}$ colony-forming units of *Methylobacterium* per gram, at least about $1\times10^{13}$ colony-forming units of *Methylobacterium* per gram, or at least about $5\times10^{13}$ colony-forming units of *Methylobacterium* per gram of the solid phase are provided. In certain embodiments, compositions with a *Methylobacterium* titer of at least about $1\times10^6$ colony-forming units per gram, at least about $5\times10^6$ colony-forming units per gram, at least about $1\times10^7$ colony-forming units per gram, at least about $5\times10^8$ colony-forming units per gram, at least about $1\times10^9$ colony-forming units per gram, or at least about $5\times10^9$ colony-forming units per gram to at least about $6\times10^{10}$ colony-forming units of *Methylobacterium* per gram, at least about $1\times10^{11}$ colony-forming units of *Methylobacterium* per gram, at least about $1\times10^{12}$ colony-forming units of *Methylobacterium* per gram, at least about $1\times10^{13}$ colony-forming units of *Methylobacterium* per gram, or at least about $5\times10^{13}$ colony-forming units of *Methylobacterium* per gram of particles in the composition containing the particles that comprise a solid substance wherein a mono-culture or co-culture of *Methylobacterium* sp. is adhered thereto are provided. In certain embodiments, compositions with a *Methylobacterium* titer of at least about $1\times10^6$ colony-forming units per mL, at least about $5\times10^6$ colony-forming units per mL, at least about $1\times10^7$ colony-forming units per mL, or at least about $5\times10^8$ colony-forming units per mL to at least about $6\times10^{10}$ colony-forming units of *Methylobacterium* per mL in a composition comprising an emulsion wherein a mono-culture or co-culture of a *Methylobacterium* sp. adhered to a solid substance is provided therein or grown therein are provided. In certain embodiments, compositions with a *Methylobacterium* titer of at least about $1\times10^6$ colony-forming units per mL, at least about $5\times10^6$ colony-forming units per mL, at least about $1\times10^7$ colony-forming units per mL, or at least about $5\times10^8$ colony-forming units per mL to at least about $6\times10^{10}$ colony-forming units of *Methylobacterium* per mL of in a composition comprising an emulsion wherein a mono-culture or co-culture of a *Methylobacterium* sp. is provided therein or grown therein is provided. In certain embodiments of any of the aforementioned compositions, the *Methylobacterium* sp. is selected from the group consisting of NLS0017 (NRRL B-50931), NLS0020 (NRRL B-50930), NLS0021 (NRRL B-50939), NLS0037 (NRRL B-50941), NLS0038 (NRRL B-50942), NLS0042 (NRRL B-50932), NLS0046 (NRRL B-50929), NLS0062 (NRRL B-50937), NLS0064 (NRRL B-50938), NLS0065 (NRRL B-50935), NLS0066 (NRRL B-50940), NLS0068 (NRRL B-50934), NLS0069 (NRRL B-50936), NLS0089 (NRRL B-50933), and derivatives thereof. In certain embodiments of any of the aforementioned compositions, the composition can further comprise an agriculturally acceptable adjuvant, an agriculturally acceptable excipient, or combination thereof. In certain embodiments of any of the aforementioned compositions, the *Methylobacterium* sp. is selected from the group consisting of NLS0017 (NRRL B-50931), NLS0020 (NRRL B-50930), NLS0021 (NRRL B-50939), NLS0037 (NRRL B-50941), NLS0038 (NRRL B-50942), NLS0042 (NRRL B-50932), NLS0046 (NRRL B-50929), NLS0062 (NRRL B-50937), NLS0064 (NRRL B-50938), NLS0065 (NRRL B-50935), NLS0066 (NRRL B-50940), NLS0068 (NRRL B-50934), NLS0069 (NRRL B-50936), NLS0089 (NRRL B-50933), derivatives thereof; and also comprises an agriculturally acceptable adjuvant, excipient, or combination thereof.

EXAMPLES

The following examples are included to demonstrate preferred embodiments of the invention. It will be appreciated by those of skill in the art that the techniques disclosed in the following examples represent techniques discovered by the Applicants to function well in the practice of the invention, and thus can be considered to constitute preferred modes for its practice. However, those of skill in the art should, in light of the instant disclosure, appreciate that many changes can be made in the specific embodiments that are disclosed, while still obtaining like or similar results, without departing from the scope of the invention**.

Example 1. Culturing of PPFM Strains in a Liquid Growth Media Supplemented with a Solid Substance The liquid growth medium used to culture the PPFM cultures was a base salts medium supplemented with glycerol, peptone, and diatomaceous earth. The base salts medium used was ammonium mineral salts (AMS) medium. AMS medium contains, per liter, 700 milligrams of dibasic potassium phosphate anhydrous, 540 milligrams of monobasic potassium phosphate anhydrous, one gram of magnesium sulfate heptahydrate, 500 milligrams of ammonium chloride anhydrous, and 200 milligrams of calcium chloride dihydrate.

AMS base medium was prepared from three stock solutions, listed below:

Stock Solution I: For One Liter at 50× Concentration

| | |
|---|---|
| dibasic potassium phosphate, anhydrous | 35 grams |
| monobasic potassium phosphate, anhydrous | 27 grams |

Stock Solution II: For One Liter at 50× Concentration

| | |
|---|---|
| magnesium sulfate heptahydrate | 50 grams |
| ammonium chloride, anhydrous | 25 grams |

Stock Solution III: For One Liter at 50× Concentration

| | |
|---|---|
| calcium chloride dihydrate | 10 grams |

Stock solutions I, II, and III were autoclaved separately.

To prepare one liter of liquid AMS medium with glycerol, peptone, and diatomaceous earth, the following were added to 920 ml of distilled water:
  20 ml of stock solution I
  20 ml of stock solution II 20 ml of stock solution III
20 ml of a 50% glycerol stock solution
10 grams of peptone
2 grams of diatomaceous earth The resulting solution with suspended diatomaceous earth was sterilized by autoclaving.

Two liters of the above AMS medium were placed into a four-liter flask. Two milliliters of liquid culture PPFMs were added to the media to inoculate. The flask was then placed in an incubated shaker set to 240 RPM and 30 degrees Celsius. The cultures were grown for six days and then stored at 4 degrees Celsius for future use.

Example 2. Seed Inoculation of 'Rex' Lettuce to Identify PPFMs that Enhance Root and Shoot Growth Seeding A 104 cell Oasis HorticubeXL™ (bottom grooved, single dibble; Smithers-Oasis North America, Kent, Ohio, USA) was placed into a 1020 flat without holes. Four cubes were removed in the center of grid to allow for bottom watering. The Oasis HorticubeXL™ was watered in so that it was fully saturated, the shower setting with tempered water was used. One seed was placed in each cell for a total of 100 seeds per group.

Inoculation of Lettuce Seeds

The PPFM strains to be tested were grown as described in Example 1 in a liquid medium supplemented with a solid substance. In the biohood, the desired amount of PPFM solution was pipetted into conical tubes (make sure to swirl/shake bottle vigorously before pipetting to suspend particulates). A centrifuge was used to spin down at 3500 RPM for 15 minutes at 23° C. While tubes were spun, a volume of tepid tap water was measured out to bring the volume of each sample up to total volume.

Liquid was carefully poured off from each tube, careful to keep the pellet intact. The appropriate volume of tap water was added to each tube to match its initial volume of PPFM solution. Water re-suspended PPFMS were used as quickly as possible.

100 microliters of solution (PPFM solution for treated groups and tap water for control groups) was pipetted onto the top of each seed. After every 3 rows, the tube was capped and shaken to resuspend any PPFMs that may have settled to the bottom. Pipette tips were changed between each group to avoid cross contamination. Tags were labeled and dated for each flat and clear humidity domes place on top of flat. The flat were placed in a growth chamber with temperature settings at 20 C and 12 hour days with 200 micromole lighting.

Growth

After five to six days, domes were removed after seeds were germinated. Flats were bottom watered only and fertilized with Jack's™ 15-16-17 (JR PETERS, Inc. Allentown, Pa., USA) at every watering (approximately every other day).

Daily repositioning of the flats was carried out to prevent potential effects on growth due to variations of light conditions in the growth chamber.

Processing

Flats were harvested between two and three weeks. Clear humidity domes were placed on each flat to prevent evapotranspiration during transport. Domes were left in place until flat was being processed. Each plant was cut directly below the cotyledons and immediately weighed on an analytical balance.

Observations

It was observed that some strains repeatedly showed an increase in shoot biomass of Lettuce seedlings when a seed was treated at the time of planting. Visual observations of root mass and development were also made, treated groups showed more growth at the time of harvest. Due to the natural variance of biological systems all samples sizes were 98-100 plants minimum and anything below 12% difference was not considered significant.

Conclusion

It was apparent that strains NLS0017, NLS0020, NLS0066, NLS0065, and NLS0089 show an increase in wet weight of lettuce seedlings following seed treatment. Strains NLS0069, NLS0037, NLS0038, and NLS0062 exhibited negligible increases in wet weight in comparison to the controls. Also noted along with an increase in shoot biomass is a corresponding increase in root development.

TABLE 2

Effects of seed treatments on lettuce growth

| strain | titer | seedling wet weight (mg) control | experimental | difference (%) | confidence interval |
|---|---|---|---|---|---|
| NLS0017 | 2.7E+08 | 226.18 | 306.36 | 35.45% | 0.000 |
| NLS0017 | 1.4E+08 | 298.27 | 353.34 | 18.46% | 0.012 |
| NLS0017 | 2.7E+08 | 169.56 | 176.68 | 4.20% | 0.567 |
| NLS0017 | 1.1E+09 | 98.92 | 167.51 | 69.34% | 0.000 |
| NLS0020 | 7.2E+08 | 226.18 | 274.46 | 21.35% | 0.027 |
| NLS0020 | 1.2E+09 | 98.92 | 157.11 | 58.83% | 0.000 |
| NLS0020 | 1.2E+09 | 462.20 | 614.72 | 33.00% | 0.000 |
| NLS0021 | ND[2] | 462.20 | 539.39 | 16.70% | 0.008 |
| NLS0037 | 3.0E+08 | 226.18 | 258.68 | 14.37% | 0.085 |
| NLS0038 | 5.2E+07 | 462.20 | 514.99 | 11.42% | 0.070 |
| NLS0042 | 2.1E+08 | 226.18 | 310.85 | 37.44% | 0.000 |
| NLS0042 | 1.1E+08 | 169.56 | 189.46 | 11.73% | 0.105 |
| NLS0046 | 1.8E+09 | 462.20 | 511.78 | 10.73% | 0.084 |
| NLS0062 | 1.8E+08 | 169.56 | 187.62 | 10.65% | 0.121 |
| NLS0064 | ND[2] | 169.56 | 157.67 | −7.01% | 0.275 |
| NLS0065 | 1.2E+08 | 169.56 | 211.92 | 24.98% | 0.001 |
| NLS0065 | 9.1E+07 | 98.92 | 132.35 | 33.80% | 0.000 |
| NLS0066 | 5.9E+08 | 56.15 | 69.57 | 23.91% | 0.000 |
| NLS0066 | 4.2E+08 | 546.61 | 665.46 | 21.74% | 0.000 |
| NLS0066 | 1.2E+08 | 98.92 | 129.81 | 31.23% | 0.000 |
| NLS0068 | 3.1E+08 | 213.52 | 234.95 | 10.04% | 0.029 |
| NLS0069 | 5.6E+07 | 226.18 | 244.25 | 7.99% | 0.307 |
| NLS0069 | 5.6E+07 | 298.27 | 332.53 | 11.49% | 0.144 |
| NLS0089 | 1.5E+08 | 98.92 | 146.99 | 48.60% | 0.000 |
| NLS0089 | ND[2] | 462.20 | 600.82 | 29.99% | 0.000 |

[1]Each line represents data obtained from a separate flats of plants obtained from treated seed versus control seed.
[2]ND: not determined.

Example 3. Foliar Application of 'Rex' Lettuce to Observe how PPFMs Effect Root and Shoot Growth Seeding A 104 cell Oasis HorticubeXL (bottom grooved, single dibble) was placed into a 1020 flat without holes. Four cubes were removed in the center of grid to allow for bottom watering. Oasis was watered in so that it was fully saturated, the shower setting with tempered water was used. One seed was placed in each cell for a total of 100 seeds per group. Tags were labeled and dated for each flat and clear humidity domes place on top of flat. The flat were placed in a growth chamber with temperature settings at 20 C and 12-hour days with 200 micromole lighting.

Inoculation of Lettuce Seedlings

After five to six days, domes were removed after seeds had germinated. Plants were inoculated at this time, when only the cotyledons had emerged. The PPFM strains to be tested were grown as described in Example 1 in a liquid medium supplemented with a solid substance. The PPFM strains to be tested were grown as described in Example 1 in a liquid medium supplemented with a solid substance. In the biohood, the desired amount of PPFM solution was pipetted into conical tubes (make sure to swirl/shake bottle vigorously before pipetting to suspend particulates). A centrifuge was used to spin down at 3500 RPM for 15 minutes at 23° C. While tubes were spun, a volume of tepid tap water was measured out to bring the volume of each sample up to total volume.

Liquid was carefully poured off from each tube, careful to keep the pellet intact. The appropriate volume of tap water was added to each tube to match its initial volume of PPFM solution. Water re-suspended PPFMS were used as quickly as possible.

100 mL of PPFM solution (tap water for control) was poured into a 1 L Solo™ Handheld Sprayer (Solo™, Newport News, Va., USA). The flat was removed from the group to avoid cross contamination. The finest mist setting was used and an even coat of solution was sprayed over the top of the seedlings, ensuring even coverage across the entire flat. For each group this was repeated, using appropriate treatment.

Growth

Flats were bottom watered only and fertilized with Jack's™ 15-16-17 (JR PETERS, Inc. Allentown, Pa., USA) at every watering (approximately every other day). Daily repositioning of the flats was carried out to prevent potential effects on growth due to variations of light conditions in the growth chamber.

Processing

Flats were harvested between two and three weeks. Clear humidity domes were placed on each flat to prevent evapotranspiration during transport. Domes were left in place until flat was being processed. Each plant was cut directly below the cotyledons and immediately weighed on an analytical balance.

Observations

It was been observed that some strains repeatedly show an increase in shoot biomass of Lettuce seedlings when the seedling was treated at the cotyledon stage. Visual observations of root mass and development were also made, that treated groups showed more growth at the time of harvest. Due to the natural variance of biological systems all samples sizes were a 98-100 plants minimum and anything below 12% difference was not considered significant.

Conclusion

It is apparent that strains NLS0042, NLS0017, NLS0020, and NLS0068 show an increase in wet weight of lettuce seedlings following foliar application. Strains NLS0069, NLS0037, NLS0038, and NLS0062 exhibited negligible increases in wet weight in comparison to the controls. Also noted along with an increase in shoot biomass is a corresponding increase in root development.

TABLE 3

Effects of foliar treatments on lettuce growth

| strain | titers | seedling wet weight (mg) control | seedling wet weight (mg) experimental | difference (%) | confidence interval |
|---|---|---|---|---|---|
| NLS0017 | 1.4E+08 | 197.04 | 213.76 | 8.49% | 0.075 |
| NLS0017 | 1.1E+09 | 157.72 | 211.03 | 33.81% | 0.000 |
| NLS0020 | 2.2E+08 | 104.41 | 145.95 | 39.79% | 0.000 |
| NLS0020 | 7.2E+08 | 205.34 | 247.12 | 20.34% | 0.030 |
| NLS0020 | 1.2E+09 | 280.84 | 260.95 | −7.08% | 0.224 |
| NLS0021 | 1.6E+07 | 157.72 | 178.46 | 13.15% | 0.021 |
| NLS0037 | ND[2] | 197.04 | 198.93 | 0.96% | 0.846 |
| NLS0038 | 7.4E+07 | 197.04 | 186.04 | −5.58% | 0.250 |
| NLS0042 | 9.3E+07 | 103.36 | 127.05 | 22.92% | 0.000 |
| NLS0042 | 2.1E+08 | 205.34 | 235.92 | 14.89% | 0.095 |
| NLS0042 | 6.4E+07 | 298.27 | 331.62 | 11.18% | 0.138 |
| NLS0042 | 1.1E+08 | 157.72 | 196.12 | 24.35% | 0.000 |
| NLS0046 | 1.8E+09 | 157.72 | 195.03 | 23.66% | 0.000 |
| NLS0062 | ND[2] | 280.84 | 243.09 | −13.44% | 0.018 |
| NLS0064 | ND[2] | 205.34 | 240.47 | 17.10% | 0.042 |
| NLS0064 | ND[2] | 298.27 | 306.88 | 2.89% | 0.691 |
| NLS0065 | 4.2E+08 | 197.04 | 214.59 | 8.91% | 0.077 |
| NLS0066 | 5.9E+08 | 205.34 | 241.92 | 17.81% | 0.035 |
| NLS0066 | 1.2E+08 | 280.84 | 166.98 | −40.54% | 0.000 |
| NLS0068 | 1.7E+08 | 104.41 | 204.26 | 95.65% | 0.000 |
| NLS0068 | 1.6E+08 | 205.34 | 288.46 | 40.47% | 0.000 |
| NLS0068 | 3.1E+08 | 298.27 | 296.68 | −0.53% | 0.944 |
| NLS0068 | 3.1E+08 | 280.84 | 264.65 | −5.76% | 0.337 |
| NLS0068 | 3.1E+08 | 157.72 | 183.84 | 16.56% | 0.010 |
| NLS0069 | 4.5E+07 | 99.85 | 103.54 | 3.70% | 0.711 |
| NLS0089 | 1.3E+09 | 280.84 | 282.94 | 0.75% | 0.896 |

[1]Each line represents data obtained from a separate flat of treated versus control plants.
[2]ND: not determined.

Example 4. Identification of Nucleic Acid Polymorphisms Present in *Methylobacterium* that Improve Lettuce Production Whole genome sequencing libraries for the Illumina™ high-throughput sequencing platform are generated for *Methylobacterium* sp. isolates provided in Table 1 using Illumina TRUSEQ™ or NEXTERA™ DNA sample preparation kits (described on the internet sites res.illumina.com/documents/products/datasheets/datasheet_truseq_dna_sample_prep_kits.pdf and res.illumina.com/documents/products/datasheets/datasheet_nextera_dna_sample_prep.pdf) using the methods described by the manufacturer. The resultant libraries are then subjected to pyrosequencing (Siqueira J F et al. J Oral Microbiol. 2012; 4: 10.3402/jom.v4i0.10743). Raw pyrosequencing-generated genomic sequence data are subjected to adaptor- and quality-based trimming for quality control. Whole-genome Shotgun Sequence Assembly (1) is achieved by assembling quality-passed data using the de novo assembler Velvet (2). For gene finding and annotation, reference training data is leveraged from TIGRFAM (9), Pfam, COG (10), and UniRef100 (11). The rRNAs are identified with RNAmmer (5), protein-coding genes are identified with Glimmer (3) or Maker (6), and tRNAs are identified with tRNAscan-SE (4). Gene functions are assigned with blastx (7), blastp (7), HMMER (8), and InterProScan against comprehensive protein databases described above (Reference Data).

Detection of polymorphisms (SNP or other DNA variations occurring as a result of insertions, deletions, and substitutions (Indels)) in the *Methylobacterium* sp. isolates of Table 1 is performed with BWA (12) and the Samtools suite (on the internet at samtools.sourceforge.net/), structural variation is identified with BreakDancer (on the internet at breakdancer.sourceforge.net/) and CoGE (on the internet at genomevolution.org/CoGe/). Polymorphisms diagnostic for *Methylobacterium* that provide for improved lettuce production are identified by comparisons of the sequences of exemplary *Methylobacterium* isolates NLS0020, NLS0066, NLS0017, NLS0065, NLS0089, NLS0042, and/or NLS0068 that improve lettuce production but that are absent from one or more *Methylobacterium* isolates that do not improve lettuce production. Polymorphisms present in exemplary *Methylobacterium* isolates NLS0020, NLS0066, NLS0017, NLS0065, NLS0089, NLS0042, and/or NLS0068 that improve lettuce production but that are absent in exemplary *Methylobacterium* isolates that do not improve lettuce production are then used to identify other *Methylobacterium* isolates that improve lettuce production.

REFERENCES FOR EXAMPLE 4

1. Miller J R, Koren S, Sutton G (2010) Assembly algorithms for next-generation sequencing data. Genomics 95: 315-327.
2. Zerbino D R, Birney E (2008) Velvet: algorithms for de novo short read assembly using de Bruijn graphs. Genome Res 18: 821-829.
3. Delcher A L, Bratke K A, Powers E C, Salzberg S L (2007) Identifying bacterial genes and endosymbiont DNA with Glimmer. Bioinformatics 23: 673-679.
4. Lowe T M, Eddy S R (1997) tRNAscan-SE: a program for improved detection of transfer RNA genes in genomic sequence. Nucleic Acids Res 25: 955-964.
5. Lagesen K, Hallin P, Rodland E A, Staerfeldt H H, Rognes T, et al. (2007) RNAmmer: consistent and rapid annotation of ribosomal RNA genes. Nucleic Acids Res 35: 3100-3108.
6. Cantarel B, Korf I, Robb S, et al. (2008) MAKER: An easy-to-use annotation pipeline designed for emerging model organism genomes. Genome Research 18: 188-196.
7. Altschul S F, Madden T L, Schaffer A A, Zhang J, Zhang Z, et al. (1997) Gapped BLAST and PSI-BLAST: a new generation of protein database search programs. Nucleic Acids Res 25: 3389-3402.
8. Eddy S R (2009) A new generation of homology search tools based on probabilistic inference. Genome Inform 23: 205-211.
9. Haft D H, Selengut J D, White O (2003) The TIGRFAMs database of protein families. Nucleic Acids Res 31: 371-373.
10. Tatusov R L, Fedorova N D, Jackson J D, Jacobs A R, Kiryutin B, et al. (2003) The COG database: an updated version includes eukaryotes. BMC Bioinformatics 4: 41.
11. Suzek B E, Huang H, McGarvey P, Mazumder R, Wu C H (2007) UniRef: comprehensive and non-redundant UniProt reference clusters. Bioinformatics 23: 1282-1288.
12. Li H. and Durbin R. (2009) Fast and accurate short read alignment with Burrows-Wheeler Transform. Bioinformatics, 25:1754-60.

Example 5. Seed Inoculation of 'Flandria' Lettuce with PPFMs Increases Shoot and Root Biomass Seeding A 276 cell sheet of Oasis HORTICUBES® (1-inch Thin-Cut; Smithers-Oasis North America, Kent, Ohio, USA) was placed into a 1020 mesh flat. The flat was divided in half with a piece of plastic to allow for two groups per flat. The Oasis HORTICUBES® were watered to full saturation. Flandria lettuce seed from Rijk Zwaan USA (Salinas, Calif., USA) was used. One seed was placed in each cell for a total of 132 or 144 seeds per group.

Inoculation of Lettuce Seeds

The PPFM strains to be tested were grown as described in Example 1 in a liquid medium supplemented with diatomaceous earth at 2 grams/liter. At the bench, the desired amount of PPFM solution was pipetted into conical tubes (making sure to swirl/shake bottle vigorously before pipetting to suspend particulates). A centrifuge was used to pellet the cells at 7500 RPM for 5 minutes at 23° C. The supernatant was discarded, and the PPFM pellets were resuspended in an equal volume of water.

100 microliters of solution (PPFM solution for treated groups and tap water for control groups) were pipetted onto the top of each seed. The tube was shaken periodically to keep the PPFM cells in suspension. Clear humidity domes were placed over each flat. The flats were placed in a greenhouse with temperature settings of 30° C. during the day, 28° C. at night and with a 16-hour day length attained with using supplemental light as necessary.

Growth

After two to three days after planting, the seeds had germinated, and the humidity domes were removed. The flats were top watered and fertilized with Jack's™ 15-16-17 (JR PETERS, Inc. Allentown, Pa., USA) at every watering. Daily repositioning of the flats was carried out to prevent potential effects on growth due to variations of light conditions in the growth chamber.

Processing

The lettuce seedlings were harvested at 10 days after planting. Each plant was cut directly below the cotyledons and immediately weighed on an analytical balance.

Observations

It was observed that some strains repeatedly showed an increase in shoot biomass of the lettuce seedlings following seed treatment. Visual observations of root mass and development were also made, and it was noted that treated groups showed more growth at the time of harvest. The outside row of each group was not harvested in order to eliminate any edge effects in the flats.

Conclusion

It was apparent that PPFM strains NLS0017, NLS0020, NLS0066 and NLS0068 showed a reproducible and statistically significant increase in the wet weight of lettuce seedlings following seed treatment. Also noted along with an increase in shoot biomass was a corresponding increase in root development.

TABLE 4

Results for Seed inoculation of 'Flandria' Lettuce

| | | seedling wet weight | | | |
|---|---|---|---|---|---|
| Strain | Titer (CFU/mL) | Control (Water) | Experimental (PPFM) | Difference (%) | confidence interval |
| NLS0017 | 1.1E+09 | 103.38 | 152.14 | 47.16% | 0.000 |
| NLS0017 | 1.1E+09 | 90.98 | 174.23 | 91.51% | 0.000 |
| NLS0017 | 1.1E+09 | 45.47 | 80.74 | 77.57% | 0.000 |
| NLS0017 | 1.1E+09 | 101.46 | 174.29 | 71.78% | 0.000 |
| NLS0017 | 1.1E+09 | 265.34 | 296.75 | 11.84% | 0.000 |
| NLS0020 | 1.2E+09 | 103.38 | 123.00 | 18.98% | 0.000 |
| NLS0020 | 1.2E+09 | 90.98 | 174.92 | 92.27% | 0.000 |
| NLS0020 | 1.2E+09 | 45.47 | 72.21 | 58.80% | 0.000 |
| NLS0020 | 1.2E+09 | 41.85 | 62.27 | 48.79% | 0.000 |
| NLS0020 | 1.2E+09 | 195.98 | 232.44 | 18.60% | 0.000 |
| NLS0020 | 1.2E+09 | 89.68 | 121.69 | 35.68% | 0.000 |
| NLS0020 | 1.2E+09 | 136.75 | 171.62 | 25.50% | 0.000 |
| NLS0020 | 1.2E+09 | 69.18 | 141.55 | 104.59% | 0.000 |

TABLE 4-continued

Results for Seed inoculation of 'Flandria' Lettuce

| Strain | Titer (CFU/mL) | Control (Water) | Experimental (PPFM) | Difference (%) | confidence interval |
|---|---|---|---|---|---|
| seedling wet weight | | | | | |
| NLS0020 | 1.2E+09 | 38.38 | 63.65 | 65.84% | 0.000 |
| NLS0020 | 1.2E+09 | 49.53 | 85.78 | 73.18% | 0.000 |
| NLS0037 | not determined | 183.18 | 199.05 | 8.67% | 0.008 |
| NLS0037 | 1.8E+08 | 68.26 | 136.58 | 100.08% | 0.000 |
| NLS0038 | 5.2E+07 | 183.18 | 201.56 | 10.03% | 0.007 |
| NLS0038 | 5.2E+07 | 68.26 | 108.01 | 58.23% | 0.000 |
| NLS0038 | 5.2E+07 | 129.32 | 154.95 | 19.82% | 0.000 |
| NLS0042 | 1.1E+08 | 59.84 | 110.04 | 83.90% | 0.000 |
| NLS0042 | 1.1E+08 | 183.18 | 186.49 | 1.81% | 0.650 |
| NLS0042 | 1.1E+08 | 68.26 | 99.76 | 46.15% | 0.000 |
| NLS0062 | 3.6E+07 | 129.32 | 156.18 | 20.77% | 0.000 |
| NLS0062 | 3.6E+07 | 140.95 | 190.36 | 35.06% | 0.000 |
| NLS0064 | 4.5E+08 | 129.32 | 158.58 | 22.63% | 0.000 |
| NLS0064 | 4.5E+08 | 140.95 | 231.99 | 64.60% | 0.000 |
| NLS0065 | 3.7E+07 | 140.95 | 211.13 | 49.80% | 0.000 |
| NLS0066 | 1.2E+08 | 103.38 | 180.71 | 74.80% | 0.000 |
| NLS0066 | 1.2E+08 | 90.98 | 163.37 | 79.57% | 0.000 |
| NLS0066 | 1.2E+08 | 45.47 | 96.07 | 111.28% | 0.000 |
| NLS0066 | 1.2E+08 | 91.32 | 114.02 | 24.86% | 0.000 |
| NLS0066 | 1.2E+08 | 209.04 | 279.74 | 33.83% | 0.000 |
| NLS0068 | 2.1E+08 | 68.26 | 98.67 | 44.55% | 0.000 |
| NLS0068 | 1.7E+08 | 129.32 | 181.12 | 40.06% | 0.000 |
| NLS0068 | 1.7E+08 | 140.95 | 217.89 | 54.59% | 0.000 |
| NLS0069 | 1.6E+08 | 59.84 | 113.78 | 90.15% | 0.000 |
| NLS0069 | 5.6E+07 | 68.26 | 75.17 | 10.12% | 0.095 |
| NLS0069 | 1.5E+08 | 129.32 | 164.10 | 26.89% | 0.000 |
| NLS0089 | 3.0E+07 | 140.95 | 225.72 | 60.14% | 0.000 |

REFERENCES

1. Abanda-Nkpwatt, D., M. Musch, J. Tschiersch, M. Boettner, and W. Schwab. 2006. Molecular interaction between *Methylobacterium extorquens* and seedlings: growth promotion, methanol consumption, and localization of the methanol emission site. J. Exp. Bot. 57: 4025-4032.
2. Broekaert W F, Terras F R, Cammue B P, Vanderleyden J (1990) An automated quantitative assay for fungal growth inhibition. FEMS Microbiology Letters 69: 55-60.
3. Cao, Y-R, Wang, Q., Jin, R-X., Tang, S-K., He, W-X., Lai, H-X, Xu, L-H., and C-L Jiang. 2011. *Methylobacterium soli* sp. nov. a methanol-utilizing bacterium isolated from the forest soil. Antonie van Leeuwenhoek (2011) 99:629-634.
4. Corpe, W. A., and D. V. Basile. 1982. Methanol-utilizing bacteria associated with green plants. Devel. Industr. Microbiol. 23: 483-493.
5. Corpe, W. A., and S. Rheem. 1989. Ecology of the methylotrophic bacteria on living leaf surfaces. FEMS Microbiol. Ecol. 62: 243-250.
6. Green, P. N. 2005. *Methylobacterium*. In Brenner, D. J., N. R. Krieg, and J. T. Staley (eds.). "Bergey's Manual of Systematic Bacteriology. Volume two, The Proteobacteria. Part C, The alpha-, beta-, delta-, and epsilonproteobacteria." Second edition. Springer, New York. Pages 567-571.
7. Green, P. N. 2006. *Methylobacterium*. In Dworkin, M., S. Falkow, E. Rosenberg, K.-H. Schleifer, and E. Stackebrandt (eds.). "The Prokaryotes. A Handbook on the Biology of Bacteria. Volume 5. Proteobacteria: Alpha and Beta Subclasses." Third edition. Springer, New York. Pages 257-265.
8. Holland, M. A. 1997. *Methylobacterium* and plants. Recent. Res. Devel. in Plant Physiol. 1: 207-213.
9. Holland, M. A., and J. C. Polacco. 1994. PPFMs and other covert contaminants: Is there more to plant physiology than just plant? Annu Rev. Plant Physiol. Plant Mol. Biol. 45: 197-209.
10. Kutschera, U. 2007. Plant-associated methylobacteria as co-evolved phytosymbionts. A hypothesis. Plant Signal Behav. 2: 74-78.
11. Lidstrom, M. E. 2006. Aerobic methylotrophic prokaryotes. In Dworkin, M., S. Falkow, E. Rosenberg, K.-H. Schleifer, and E. Stackebrandt (eds.). "The Prokaryotes. A Handbook on the Biology of Bacteria. Volume 2. Ecophysiology and biochemistry." Third edition. Springer, New York. Pages 618-634.
12. Madhaiyan, M., S. Poonguzhali, H. S. Lee, K. Hari, S. P. Sundaram, and T. M. Sa. 2005. Pink-pigmented facultative methylotrophic bacteria accelerate germination, growth and yield of sugarcane clone Co86032 (*Saccharum officinarum* L.) Biol. Fertil. Soils 41: 350-358.
13. Madhaiyan, M., S. Poonguzhali, M. Senthilkumar, S. Seshadri, H. Chung, J. Yang, S. Sundaram, and T. Sa. 2004. Growth promotion and induction of systemic resistance in rice cultivar C0-47 (*Oryza sativa* L.) by *Methylobacterium* spp. Bot. Bull. Acad. Sin. 45: 315-324.
14. Madhaiyan, M., S. Poonguzhali, and T. Sa. 2007. Influence of plant species and environmental conditions on epiphytic and endophytic pink-pigmented facultative methylotrophic bacterial populations associated with field-grown rice cultivars. J Microbiol Biotechnol. 2007 October; 17(10): 1645-54.
15. Stanier, R. Y., N. J. Palleroni, and M. Doudoroff. 1966. The aerobic pseudomonads: A taxonomic study. J. Gen. Microbiol. 43: 159-271.
16. Sy, A., Giraud, E., Jourand, P., Garcia, N., Willems, A., De Lajudie, P., Prin, Y., Neyra, M., Gillis, M., Boivin-Masson, C., and Dreyfus, B. 2001. Methylotrophic *Methylobacterium* Bacteria Nodulate and Fix Nitrogen in Symbiosis with Legumes. Jour. Bacteriol. 183(1):214-220,
17. Sy, A., A. C. J. Timmers, C. Knief, and J. A. Vorholt. 2005. Methylotrophic metabolism is advantageous for *Methylobacterium extorquens* during colonization of *Medicago truncatula* under competitive conditions. Appl. Environ. Microbiol. 71: 7245-7252.
18. Vogel, H. J., and D. M. Bonner. 1956. Acetylornithinase of *Escherichia coli*: Partial purification and some properties. J. Biol. Chem. 218: 97-106.
19. Vogel, H. J. 1956. A convenient growth medium for *Neurospora* (Medium N). Microbial Genet Bull 13: 42-43
20. Whittenbury, R., S. L. Davies, and J. F. Wilkinson. 1970. Enrichment, isolation and some properties of methane-utilizing bacteria. J. Gen. Microbiol. 61: 205-218.
21. Vuilleumier S, Chistoserdova L, Lee M C, Bringel F, Lajus A, Zhou Y, Gourion B, Barbe V, Chang J, Cruveiller S, Dossat C, Gillett W, Gruffaz C, Haugen E, Hourcade E, Levy R, Mangenot S, Muller E, Nadalig T, Pagni M, Penny C, Peyraud R, Robinson D G, Roche D, Rouy Z, Saenampechek C, Salvignol G, Vallenet D, Wu Z, Marx C J, Vorholt J A, Olson M V, Kaul R, Weissenbach J, Médigue C, Lidstrom M E. *Methylobacterium* genome sequences: a reference blueprint to investigate microbial metabolism of C1 compounds from natural and industrial sources. PLoS One. 2009; 4(5):e5584. doi: 10.1371/journal.pone.0005584. Epub 2009 May 18. PubMed PMID: 19440302; PubMed Central PMCID: PMC2680597.
22. Marx C J, Bringel F, Chistoserdova L, Moulin L, Farhan Ul Haque M, Fleischman D E, Gruffaz C, Jourand P, Knief C, Lee M C, Muller E E, Nadalig T, Peyraud R, Roselli S, Russ L, Goodwin L A, Ivanova N, Kyrpides N, Lajus A, Land M L, Médigue C, Mikhailova N, Nolan M, Woyke T, Stolyar S, Vorholt J A, Vuilleumier S. Complete genome sequences of six strains of the genus *Methylobacterium*. J Bacteriol. 2012 September; 194(17):4746-8. doi: 10.1128/JB.01009-12. PubMed PMID: 22887658; PubMed Central PMCID: PMC3415506.

23. Knief C, Frances L, Vorholt J A. Competitiveness of diverse *Methylobacterium* strains in the phyllosphere of *Arabidopsis thaliana* and identification of representative models, including *M. extorquens* PA1. Microb Ecol. 2010 August; 60(2):440-52. doi: 10.1007/s00248-010-9725-3. Epub 2010 Aug. 11. PubMed PMID: 20700590.

Example 6. Seed Inoculation of 'Rex' Lettuce with PPFMs Increases Shoot and Root Biomass Seeding A 276 cell sheet of Oasis HORTICUBES® (1-inch Thin-Cut; Smithers-Oasis North America, Kent, Ohio, USA) was placed into a 1020 mesh flat. The flat was divided in half with a piece of plastic to allow for two groups per flat. The Oasis HORTICUBES® were watered to full saturation. Rex lettuce seed was used. One seed was placed in each cell for a total of 132 or 144 seeds per group.

Inoculation of Lettuce Seeds

The PPFM strains to be tested were grown as described in Example 1 in a liquid medium supplemented with diatomaceous earth at 2 grams/liter. At the bench, the desired amount of PPFM solution was pipetted into conical tubes (making sure to swirl/shake bottle vigorously before pipetting to suspend particulates). A centrifuge was used to pellet the cells at 7500 RPM for 5 minutes at 23° C. The supernatant was discarded, and the PPFM pellets were resuspended in an equal volume of water.

100 microliters of solution (PPFM solution for treated groups and tap water for control groups) were pipetted onto the top of each seed. The tube was shaken periodically to keep the PPFM cells in suspension. Clear humidity domes were placed over each flat. The flats were placed in a greenhouse with temperature settings of 30° C. during the day, 28° C. at night and with a 16-hour day length attained with using supplemental light as necessary.

Growth

After two to three days after planting, the seeds had germinated, and the humidity domes were removed. The flats were top watered and fertilized with Jack's™ 15-16-17 (JR PETERS, Inc. Allentown, Pa., USA) at every watering. Daily repositioning of the flats was carried out to prevent potential effects on growth due to variations of light conditions in the growth chamber.

Processing

The lettuce seedlings were harvested at 10 days after planting. Each plant was cut directly below the cotyledons and immediately weighed on an analytical balance.

Observations

It was observed that some strains repeatedly showed an increase in shoot biomass of the lettuce seedlings following seed treatment. Visual observations of root mass and development were also made, and it was noted that treated groups showed more growth at the time of harvest. The outside row of each group was not harvested in order to eliminate any edge effects in the flats. The results are as shown in the following Table.

TABLE 5

| Strain | avg % Increase in Shoot Biomass in comparison to control | # of tests |
| --- | --- | --- |
| NLS0062 | 44.00% | 3 |
| NLS0020 | 37.73% | 3 |
| NLS0042 | 33.82% | 4 |
| NLS0046 | 30.86% | 3 |
| NLS0068 | 30.83% | 3 |
| NLS0038 | 29.43% | 3 |
| NLS0089 | 29.16% | 3 |
| NLS0017 | 28.53% | 5 |
| NLS0021 | 28.27% | 3 |
| NLS0037 | 26.02% | 3 |
| NLS0066 | 25.63% | 3 |
| NLS0065 | 23.35% | 3 |
| NLS0064 | 21.88% | 3 |
| NLS0069 | 4.87% | 3 |

Conclusion

It was apparent that PPFM strains NLS0017, NLS0020, NLS21, NLS0037, NLS0038, NLS42, NLS46, NLS62, NLS64, NLS0065, NLS0066, NLS0068, and NLS0089 showed a reproducible and statistically significant increase in the wet weight of lettuce seedlings following seed treatment. Also noted along with an increase in shoot biomass was a corresponding increase in root development.

Example 7. Flandria Seed Tests

Flandria lettuce seed were treated with the indicated PPFM isolates essentially as described in Example 5 to yield the following results.

TABLE 6

| strain | wet weight (mg) | | difference | CI |
| --- | --- | --- | --- | --- |
| | control | experimental | | |
| NLS0017 | 103.38 | 152.14 | 47.16% | 0.000 |
| NLS0017 | 90.98 | 174.23 | 91.51% | 0.000 |
| NLS0017 | 45.47 | 80.74 | 77.57% | 0.000 |
| NLS0017 | 101.46 | 174.29 | 71.78% | 0.000 |
| NLS0017 | 265.34 | 296.75 | 11.84% | 0.000 |
| NLS0017 | 99.82 | 163.01 | 63.30% | 0.000 |
| NLS0020 | 103.38 | 123.00 | 18.98% | 0.000 |
| NLS0020 | 90.98 | 174.92 | 92.27% | 0.000 |
| NLS0020 | 45.47 | 72.21 | 58.80% | 0.000 |
| NLS0020 | 41.85 | 62.27 | 48.79% | 0.000 |
| NLS0020 | 195.98 | 232.44 | 18.60% | 0.000 |
| NLS0020 | 89.68 | 121.69 | 35.68% | 0.000 |
| NLS0020 | 136.75 | 171.62 | 25.50% | 0.000 |
| NLS0020 | 69.18 | 141.55 | 104.59% | 0.000 |
| NLS0020 | 38.38 | 63.65 | 65.84% | 0.000 |
| NLS0020 | 49.53 | 85.78 | 73.18% | 0.000 |
| NLS0037 | 59.84 | 109.56 | 83.10% | 0.000 |
| NLS0037 | 183.18 | 199.05 | 8.67% | 0.008 |
| NLS0037 | 68.26 | 136.58 | 100.08% | 0.000 |
| NLS0037 | 97.72 | 156.97 | 60.63% | 0.000 |
| NLS0037 | 91.74 | 130.58 | 42.34% | 0.000 |
| NLS0037 | 99.08 | 108.96 | 9.97% | 0.030 |
| NLS0037 | 61.72 | 120.61 | 95.41% | 0.000 |
| NLS0042 | 59.84 | 110.04 | 83.90% | 0.000 |
| NLS0042 | 183.18 | 184.47 | 0.70% | 0.650 |
| NLS0042 | 68.26 | 99.76 | 46.15% | 0.000 |
| NLS0042 | 61.72 | 109.42 | 77.28% | 0.000 |
| NLS0065 | 140.95 | 211.13 | 49.80% | 0.000 |
| NLS0065 | 61.72 | 109.38 | 77.22% | 0.000 |
| NLS0065 | 86.75 | 154.51 | 78.11% | 0.000 |
| NLS0065 | 97.67 | 99.42 | 1.79% | 0.691 |
| NLS0066 | 103.38 | 180.71 | 74.80% | 0.000 |

TABLE 6-continued

| strain | wet weight (mg) | | | |
|---|---|---|---|---|
| | control | experimental | difference | CI |
| NLS0066 | 90.98 | 163.37 | 79.57% | 0.000 |
| NLS0066 | 45.47 | 96.07 | 111.28% | 0.000 |
| NLS0066 | 91.32 | 114.02 | 24.86% | 0.000 |
| NLS0066 | 209.04 | 279.74 | 33.83% | 0.000 |
| NLS0066 | 99.82 | 101.20 | 1.38% | 0.920 |
| NLS0135 | 223.15 | 227.21 | 1.82% | 0.588 |
| NLS0135 | 90.94 | 111.89 | 23% | 0.000 |
| NLS0135 | 145.2 | 118.14 | −19% | 0.000 |
| NLS0071 | 223.15 | 220.13 | −1.35% | 0.716 |
| NLS0071 | 90.94 | 107.2 | 18% | 0.000 |
| NLS0071 | 145.2 | 129.62 | −11% | 0.002 |
| NLS0109 | 223.15 | 215.45 | −3.45% | 0.316 |
| NLS0109 | 90.94 | 109.91 | 21% | 0.000 |
| NLS0109 | 145.2 | 126.9 | −13% | 0.001 |
| NLS0142 | 223.15 | 197.98 | −11.28% | 0.002 |
| NLS0142 | 90.94 | 94.89 | 4% | 0.324 |
| NLS0142 | 145.2 | 121.09 | −17% | 0.000 |

It was evident that the PPFM strains NLS0017, NLS0037, NLS0066, NLS0020, NLS0042, NLS0065, NLS0089, NLS0046, NLS0021. NLS0069, NLS0068, NLS0064, NLS0062, and NLS0038 could provide for increased lettuce biomass relative to control treatments.

Example 8. Identification of Orthologous Genes Present in *Methylobacterium* sp. that can Improve Lettuce Production The PPFM strains listed in Table 1 were grown on solid agar media comprising Ammonium Mineral Salts (AMS) plus glycerol and peptone at 30° C. for 5 days, essentially as described in co-assigned U.S. Patent Application Publication No. US20130324407 and incorporated herein by reference in its entirety. Genomic DNA was extracted using MO-BIO (Carlsbad, Calif.) Ultra Clean Microbial DNA Isolation kit, and 1 µg of high quality DNA was used for Illumina Nextera XT library preparation followed by Illumina 2×100 paired-end sequencing on a HiSeq2000 system. Raw Illumina genomic sequence data were subjected to adaptor- and quality-based trimming for quality control. Whole-genome Shotgun Sequence Assembly was achieved by assembling quality-passed data using the de novo assembler SPADES (33). For gene finding and annotation, reference training data was leveraged from TIGRFAM (9), Pfam, COG (10), and UniRef100 (11). The rRNAs were identified with RNAmmer (5), protein-coding genes were identified with Glimmer (3) and Maker (6), and tRNAs were identified with tRNAscan-SE (4). Gene functions were assigned with blastx (7), blastp (7), HMMER (8), and InterProScan against comprehensive protein databases described above (Reference Data). Detection of polymorphisms (SNP or other DNA variations occurring as a result of insertions, deletions, and substitutions (Indels)) in the *Methylobacterium* sp. isolates was performed with BWA (12) and the Samtools suite (on the internet at samtools.sourceforge.net/) and the Genome Analysis Toolkit (GATK, on the world wide web internet site "broadinstitute.org/gatk/"), structural variation was identified with BreakDancer (on the internet at breakdancer.sourceforge.net/) and CoGE (on the internet at genomevolution.org/CoGe/).

Genes that encoded open reading frames were predicted from the assembled whole genomic sequences of NLS0017, NLS0020, NLS0037, NLS0042, NLS0065, NLS0066, NLS0135, NLS0071, NLS0109, and NLS0142 essentially as described above. Within and between genome orthologous genes were clustered using OrthoMCL (available on the world wide web internet site "orthomcl.org/orthomcl/"). Putative functional annotations were assigned to gene products using BLASTP (available on the internet site "blast.ncbi.nlm.nih.gov/Blast.cgi") against the UniProt database (available on the world wide web internet site "uniprot.org/"). Genes present in individual genomes of NLS0017, NLS0020, NLS0037, NLS0042, NLS0065, and NLS0066 that could improve lettuce production (as shown in Example 7) but absent in the whole set of genomes of NLS0135, NLS0071, NLS0109, and NLS0142 that did not improve lettuce production (as shown in Example 7) were identified in OrthoMCL clusters using custom software. The encoded proteins found in the *Methylobacterium* NLS0017, NLS0020, NLS0037, NLS0042, NLS0065, and NLS0066 that could improve lettuce production are provided in the sequencing listing as SEQ ID NO: 1-5125. The nucleic acid sequences that encode the proteins of SEQ ID NO: 1-5125 are SEQ ID NO: 5126-10250, respectively. The proteins encoded by genes present in NLS0017 but absent from NLS0135, NLS0071, NLS0109, and NLS0142 are provided as SEQ ID NO: 1-1086. The proteins encoded by genes present in NLS0020 but absent from NLS0135, NLS0071, NLS0109, and NLS0142 are provided as SEQ ID NO: 1087-2176. The proteins encoded by genes present in NLS0037 but absent from NLS0135, NLS0071, NLS0109, and NLS0142 are provided as SEQ ID NO: 2177-2461. The proteins encoded by genes present in NLS0042 but absent from NLS0135, NLS0071, NLS0109, and NLS0142 are provided as SEQ ID NO: 2462-3347. The proteins encoded by genes present in NLS0065 but absent from NLS0135, NLS0071, NLS0109, and NLS0142 are provided as SEQ ID NO: 3348-3949. The proteins encoded by genes present in NLS0066 but absent from NLS0135, NLS0071, NLS0109, and NLS0142 are provided as SEQ ID NO: 3950-5125. Orthologous gene groups representing genes encoding proteins found in the genomes of at least two individual genomes of NLS0017, NLS0020, NLS0037, NLS0042, NLS0065, and/or NLS0066 that could improve lettuce production (as shown in Example 7) but that are absent in the whole set of genomes of NLS0135, NLS0071, NLS0109, and NLS0142 that did not improve lettuce production are provided in Table 7. In Table 7, groups of orthologous genes are provided in each row, where the longest sequence and associated unique Seq ID Number are designated as a reference sequence to represent the ortholog cluster (Column 3 of Table 7). The ortholog group identification number is provided in column 1 of Table 7, the closest gene identity based on database comparisons is provided in column 2 of Table 7, and the reference sequence for each ortholog cluster is provided in column 3 of Table 7. Examples of ortholog sequences found in NLS0017, NLS0020, NLS0037, NLS0042, NLS0065, and NLS0066 are provided as SEQ ID NO: in Table 7, columns 4, 5, 6, 7, 8, and 9, respectively.

TABLE 7

Orthologous Gene Groups

| Unique Ortholog Group Identifier | Annotation | Reference. Ortholog SEQ ID NO: | NLS0017 Ortholog SEQ ID NO: | NLS0020 Ortholog SEQ ID NO: | NLS0037 Ortholog SEQ ID NO: | NLS0042 Ortholog SEQ ID NO: | NLS0065 Ortholog SEQ ID NO: | NLS0066 Ortholog SEQ ID NO: |
|---|---|---|---|---|---|---|---|---|
| 4678v20141116 | hypothetical protein Mpop_4447 | 2467 | 8 | 1091 | NA | 2467 | 3352 | 3954 |
| 4682v20141116 | hypothetical protein Mchl_0132 | 2468 | 9 | 1092 | NA | 2468 | 3353 | 3955 |
| 4747v20141116 | histidine kinase | 3357 | 11 | 1093 | NA | 2472 | 3357 | 3959 |
| 4748v20141116 | transcriptional regulator | 1094 | 12 | 1094 | NA | 2473 | 3358 | 3960 |
| 4749v20141116 | histidine kinase | 13 | 13 | 1095 | NA | 2474 | 3359 | 3961 |
| 4809v20141116 | saccharopine dehydrogenase | 14 | 14 | 1097 | NA | 2481 | 3365 | 3966 |
| 4837v20141116 | ABC transporter-like protein | 1100 | 17 | 1100 | 2179 | 2484 | 3367 | NA |
| 4841v20141116 | hypothetical protein Mpop_0734 | 3968 | 19 | 1102 | NA | 2486 | 3368 | 3968 |
| 4904v20141116 | HlyD family type I secretion membrane fusion protein | 3370 | 22 | 1103 | NA | 2491 | 3370 | 3972 |
| 4905v20141116 | Transcriptional regulator XRE family | 23 | 23 | 1104 | NA | 2492 | 3371 | 3973 |
| 4942v20141116 | type I secretion system ATPase | 1106 | 25 | 1106 | NA | 2494 | 3373 | 3974 |
| 3799v20141116 | hypothetical protein | 3950 | 1 | 1088 | NA | 2462 | NA | 3950 |
| 4369v20141116 | hypothetical protein METDI0048 | 3952 | 6 | 1090 | 2177 | NA | NA | 3952 |
| 4454v20141116 | FAD-dependent pyridine nucleotide-disulfide oxidoreductase | 2463 | 7 | NA | 2178 | 2463 | 3348 | NA |
| 4740v20141116 | arsenite efflux pump ACR3 | 2471 | 10 | NA | NA | 2471 | 3356 | 3958 |
| 4926v20141116 | LysR family transcriptional regulator | 3372 | 24 | 1105 | NA | 2493 | 3372 | NA |
| 4948v20141116 | hypothetical protein Mchl_1383 | 2180 | 26 | NA | 2180 | 2495 | 3374 | NA |
| 5012v20141116 | COG3293: Transposase and inactivated derivatives | 27 | 27 | 1107 | NA | 2500 | 3377 | NA |
| 5041v20141116 | hypothetical protein | 28 | 28 | 1108 | NA | 2502 | 3378 | NA |
| 5096v20141116 | hypothetical protein | 30 | 30 | 1109 | NA | 2504 | 3380 | NA |
| 5122v20141116 | hypothetical protein Mchl_3038 | 2510 | 31 | 1110 | NA | 2510 | 3385 | NA |
| 5202v20141116 | hypothetical protein Mext_4122 | 2515 | 33 | 1113 | NA | 2515 | 3387 | NA |
| 5212v20141116 | hypothetical protein | 1114 | 35 | 1114 | NA | 2516 | 3388 | NA |
| 5238v20141116 | OmpA/MotB domain-containing protein | 3987 | 36 | 1115 | NA | NA | 3392 | 3987 |
| 5246v20141116 | multidrug transporter MatE | 1116 | 37 | 1116 | 2182 | 2521 | NA | NA |
| 5258v20141116 | hypothetical protein | 1117 | 38 | 1117 | NA | 2522 | 3393 | NA |
| 5263v20141116 | porin | 3394 | 39 | 1118 | NA | 2523 | 3394 | NA |
| 5363v20141116 | hypothetical protein | 40 | 40 | 1119 | NA | 2533 | 3401 | NA |
| 5374v20141116 | cytochrome P450 | 1120 | 41 | 1120 | NA | 2534 | NA | 3992 |
| 5433v20141116 | peptidase C14 | 3996 | 42 | 1121 | NA | NA | 3412 | 3996 |
| 5434v20141116 | hypothetical protein | 43 | 43 | 1122 | NA | NA | 3413 | 3997 |
| 5497v20141116 | ATPase | 44 | 44 | NA | NA | 2561 | 3425 | 4003 |
| 5506v20141116 | hypothetical protein | 4004 | 45 | 1123 | NA | NA | 3426 | 4004 |
| 5507v20141116 | hypothetical protein | 3427 | 46 | 1124 | NA | NA | 3427 | 4005 |
| 5508v20141116 | hypothetical protein Mpop_0725 | 4006 | 47 | 1125 | NA | NA | 3428 | 4006 |
| 5509v20141116 | hypothetical protein | 3429 | 48 | 1126 | NA | NA | 3429 | 4007 |
| 5510v20141116 | hypothetical protein | 3430 | 49 | 1127 | NA | NA | 3430 | 4008 |
| 5585v20141116 | hypothetical protein Mpop_0722 | 51 | 51 | 1128 | NA | NA | 3443 | 4012 |
| 5586v20141116 | hypothetical protein Mpop_0723 | 52 | 52 | 1129 | NA | NA | 3444 | 4013 |
| 5790v20141116 | hypothetical protein | 57 | 57 | 1134 | NA | 2619 | 3476 | NA |
| 5984v20141116 | Penicillin-binding protein | 2676 | 60 | 1136 | NA | 2676 | 3502 | NA |
| 6022v20141116 | plasmid stabilization protein ParE | 2190 | NA | 1139 | 2190 | 2680 | NA | 4021 |
| 6819v20141116 | short-chain dehydrogenase | 76 | 76 | 1155 | 2201 | NA | 3542 | NA |

TABLE 7-continued

Orthologous Gene Groups

| Unique Ortholog Group Identifier | Annotation | Reference. Ortholog SEQ ID NO: | NLS0017 Ortholog SEQ ID NO: | NLS0020 Ortholog SEQ ID NO: | NLS0037 Ortholog SEQ ID NO: | NLS0042 Ortholog SEQ ID NO: | NLS0065 Ortholog SEQ ID NO: | NLS0066 Ortholog SEQ ID NO: |
|---|---|---|---|---|---|---|---|---|
| 7006v20141116 | binding-protein-dependent transport system inner membrane protein | 4067 | 84 | 1163 | NA | 2796 | NA | 4067 |
| 7040v20141116 | hypothetical protein | 85 | 85 | 1164 | NA | 2799 | NA | 4069 |
| 7299v20141116 | glycosyltransferase family 2 | 1180 | 105 | 1180 | 2206 | NA | NA | 4087 |
| 7707v20141116 | metal-dependent phosphohydrolase | 127 | 127 | 1203 | 2214 | NA | NA | 4111 |
| 8313v20141116 | GDP-L-fucose synthase | 197 | 197 | 1264 | 2237 | NA | NA | 4171 |
| 8314v20141116 | NAD-dependent epimerase/dehydratase | 198 | 198 | 1265 | 2238 | NA | NA | 4172 |
| 8315v20141116 | NAD-dependent epimerase/dehydratase | 199 | 199 | 1266 | 2239 | NA | NA | 4173 |
| 8898v20141116 | Transcriptional regulator LysR family | 2971 | 250 | 1309 | 2263 | 2971 | NA | NA |
| 4353v20141116 | transposase partial | 5 | 5 | 1089 | NA | NA | NA | 3951 |
| 4597v20141116 | peroxiredoxin | 2464 | NA | NA | NA | 2464 | 3350 | 3953 |
| 4733v20141116 | acyl-CoA dehydrogenase type 2 domain | 3956 | NA | NA | NA | 2469 | 3354 | 3956 |
| 4734v20141116 | ABC transporter | 3355 | NA | NA | NA | 2470 | 3355 | 3957 |
| 4782v20141116 | ABC transporter inner membrane protein | 2475 | NA | NA | NA | 2475 | 3360 | 3962 |
| 4783v20141116 | twin-arginine translocation pathway signal | 2476 | NA | NA | NA | 2476 | 3361 | 3963 |
| 4792v20141116 | COG3293: Transposase and inactivated derivatives | 1096 | NA | 1096 | NA | 2477 | 3362 | NA |
| 4797v20141116 | hypothetical protein METDI2339 | 3364 | NA | NA | NA | 2480 | 3364 | 3964 |
| 4829v20141116 | diguanylate cyclase | 3366 | NA | NA | NA | 2482 | 3366 | 3967 |
| 4831v20141116 | hypothetical protein | 16 | 16 | 1098 | NA | 2483 | NA | NA |
| 4839v20141116 | hypothetical protein | 2485 | 18 | 1101 | NA | 2485 | NA | NA |
| 4901v20141116 | OmpW family protein | 3971 | NA | NA | NA | 2490 | 3369 | 3971 |
| 5103v20141116 | hypothetical protein METDI2906 | 3381 | NA | NA | NA | 2506 | 3381 | 3977 |
| 5118v20141116 | aminoglycoside phosphotransferase | 2508 | NA | NA | NA | 2508 | 3383 | 3978 |
| 5144v20141116 | hypothetical protein | 1111 | NA | 1111 | 2181 | NA | NA | 3980 |
| 5183v20141116 | ABC transporter | 2513 | 32 | 1112 | NA | 2513 | NA | NA |
| 5217v20141116 | hemolysin | 2517 | NA | NA | NA | 2517 | 3389 | 3985 |
| 5283v20141116 | BadM/Rrf2 family transcriptional regulator | 3988 | NA | NA | NA | 2525 | 3396 | 3988 |
| 5391v20141116 | 5'-nucleotidase | 2543 | NA | NA | NA | 2543 | 3407 | 3994 |
| 5420v20141116 | virulence-associated protein D | 3411 | NA | NA | NA | 2547 | 3411 | 3995 |
| 5471v20141116 | hypothetical protein Mpop__1169 | 3416 | NA | NA | NA | 2550 | 3416 | 3998 |
| 5473v20141116 | hypothetical protein Mpop__3884 | 2551 | NA | NA | NA | 2551 | 3417 | 3999 |
| 5487v20141116 | hypothetical protein | 2558 | NA | NA | NA | 2558 | 3422 | 4002 |
| 5513v20141116 | hypothetical protein Mext__2210 | 3431 | 50 | NA | NA | 2563 | 3431 | NA |
| 5566v20141116 | hypothetical protein METDI0649 | 4010 | NA | NA | NA | 2572 | 3439 | 4010 |
| 5669v20141116 | hypothetical protein | 53 | 53 | 1130 | NA | NA | 3458 | NA |
| 5675v20141116 | GreA/GreB family elongation factor | 54 | 54 | 1131 | NA | NA | 3460 | NA |
| 5683v20141116 | RND family efflux transporter MFP subunit | 2590 | NA | NA | 2183 | 2590 | 3462 | NA |
| 5728v20141116 | permease of ABC transporter | 2603 | NA | NA | 2184 | 2603 | NA | 4016 |
| 5782v20141116 | hypothetical protein METDI1995 | 2617 | 56 | NA | NA | 2617 | 3474 | NA |
| 5850v20141116 | hypothetical protein | 4018 | NA | NA | NA | 2631 | 3485 | 4018 |
| 5911v20141116 | hypothetical protein MexAM1_META1p1120 | 2647 | NA | NA | NA | 2647 | 3497 | 4019 |

TABLE 7-continued

Orthologous Gene Groups

| Unique Ortholog Group Identifier | Annotation | Reference. Ortholog SEQ ID NO: | NLS0017 Ortholog SEQ ID NO: | NLS0020 Ortholog SEQ ID NO: | NLS0037 Ortholog SEQ ID NO: | NLS0042 Ortholog SEQ ID NO: | NLS0065 Ortholog SEQ ID NO: | NLS0066 Ortholog SEQ ID NO: |
|---|---|---|---|---|---|---|---|---|
| 5989v20141116 | hypothetical protein | 61 | 61 | 1137 | NA | 2677 | NA | NA |
| 6009v20141116 | TetR family transcriptional regulator | 1138 | 62 | 1138 | NA | 2679 | NA | NA |
| 6028v20141116 | UDP-glucose 6-dehydrogenase | 63 | 63 | 1140 | NA | NA | 3504 | NA |
| 6091v20141116 | DNA topoisomerase III | 64 | 64 | 1141 | NA | NA | NA | 4024 |
| 6093v20141116 | Fe—S type tartrate/fumarate subfamily hydro-lyase subunit alpha | 65 | 65 | 1142 | NA | NA | NA | 4025 |
| 6183v20141116 | PAS/PAC sensor hybrid histidine kinase | 2697 | NA | NA | NA | 2697 | 3513 | 4028 |
| 6196v20141116 | hypothetical protein | 67 | 67 | NA | 2191 | 2700 | NA | NA |
| 6235v20141116 | hypothetical protein | 1144 | 70 | 1144 | NA | NA | NA | 4031 |
| 6301v20141116 | hypothetical protein Mchl_1527 | 2709 | NA | NA | NA | 2709 | 3517 | 4032 |
| 6437v20141116 | Sel1 domain-containing protein | 3521 | 72 | 1146 | NA | NA | 3521 | NA |
| 6442v20141116 | fumarate hydratase | 2724 | 73 | 1147 | NA | 2724 | NA | NA |
| 6618v20141116 | hypothetical protein Mpop_4203 | 2745 | NA | NA | 2199 | 2745 | NA | 4045 |
| 6687v20141116 | peptide ABC transporter substrate-binding protein | 75 | 75 | 1152 | NA | NA | 3534 | NA |
| 6785v20141116 | hydrolase alpha/beta hydrolase fold family protein | 2763 | NA | NA | NA | 2763 | 3540 | 4052 |
| 6823v20141116 | thioesterase superfamily protein | 77 | 77 | 1157 | NA | NA | 3543 | NA |
| 7042v20141116 | arginine ABC transporter ATP-binding protein | 86 | 86 | 1165 | NA | NA | NA | 4070 |
| 7043v20141116 | glyoxalase/bleomycin resistance protein/dioxygenase | 2800 | 87 | 1166 | NA | 2800 | NA | NA |
| 7048v20141116 | glyoxalase | 89 | 89 | 1167 | NA | NA | NA | 4071 |
| 7189v20141116 | hypothetical protein VOLCADRAFT_119358 | 1172 | 97 | 1172 | NA | NA | NA | 4077 |
| 7290v20141116 | succinate dehydrogenase and fumarate reductase iron-sulfur protein | 4080 | 98 | 1173 | NA | NA | NA | 4080 |
| 7291v20141116 | succinate dehydrogenase membrane anchor | 99 | 99 | 1174 | NA | NA | NA | 4081 |
| 7292v20141116 | succinate dehydrogenase cytochrome b subunit | 100 | 100 | 1175 | NA | NA | NA | 4082 |
| 7293v20141116 | L(+)-tartrate or fumarate dehydratase subunit beta | 101 | 101 | 1176 | NA | NA | NA | 4083 |
| 7294v20141116 | fumarate reductase | 102 | 102 | 1177 | NA | NA | NA | 4084 |
| 7295v20141116 | YCII-like protein | 103 | 103 | 1178 | NA | NA | NA | 4085 |
| 7297v20141116 | TRAP-type transport system periplasmic component-like protein | 104 | 104 | 1179 | NA | NA | NA | 4086 |
| 7310v20141116 | ABC transporter substrate-binding protein | 4088 | 106 | 1183 | NA | NA | NA | 4088 |
| 7311v20141116 | glutathione ABC transporter permease GsiD | 107 | 107 | 1184 | NA | NA | NA | 4089 |
| 7312v20141116 | oligopeptide/dipeptide ABC transporter ATPase | 1185 | 108 | 1185 | NA | NA | NA | 4090 |
| 7313v20141116 | ABC transporter-like protein | 109 | 109 | 1186 | NA | NA | NA | 4091 |
| 7338v20141116 | acyl-CoA dehydrogenase domain-containing protein | 113 | 113 | 1188 | 2208 | NA | NA | NA |

TABLE 7-continued

Orthologous Gene Groups

| Unique Ortholog Group Identifier | Annotation | Reference. Ortholog SEQ ID NO: | NLS0017 Ortholog SEQ ID NO: | NLS0020 Ortholog SEQ ID NO: | NLS0037 Ortholog SEQ ID NO: | NLS0042 Ortholog SEQ ID NO: | NLS0065 Ortholog SEQ ID NO: | NLS0066 Ortholog SEQ ID NO: |
|---|---|---|---|---|---|---|---|---|
| 7341v20141116 | hypothetical protein M446_1279 | 4094 | 114 | 1189 | NA | NA | NA | 4094 |
| 7508v20141116 | hypothetical protein | 2856 | NA | 1193 | NA | 2856 | NA | 4104 |
| 7536v20141116 | FAD-binding monooxygenase | 121 | 121 | 1194 | NA | NA | 3583 | NA |
| 7711v20141116 | 2-hydroxyacid dehydrogenase | 4112 | 128 | 1204 | NA | NA | NA | 4112 |
| 7729v20141116 | amino acid ABC transporter | 4113 | 130 | 1206 | NA | NA | NA | 4113 |
| 7730v20141116 | GntR family transcriptional regulator | 131 | 131 | 1207 | NA | NA | NA | 4114 |
| 7750v20141116 | alpha-amylase | 135 | 135 | 1209 | NA | NA | NA | 4115 |
| 7844v20141116 | hypothetical protein | 139 | 139 | 1214 | NA | 2890 | NA | NA |
| 7845v20141116 | FAD-dependent oxidoreductase | 2216 | 140 | 1215 | 2216 | NA | NA | NA |
| 7868v20141116 | hypothetical protein | 143 | 143 | 1217 | NA | NA | NA | 4126 |
| 7877v20141116 | hypothetical protein Mchl_0532 | 4127 | 145 | 1220 | NA | NA | NA | 4127 |
| 7885v20141116 | binding-protein-dependent transport system inner membrane protein | 146 | 146 | 1221 | NA | NA | NA | 4128 |
| 7890v20141116 | taurine ABC transporter permease | 1223 | 148 | 1223 | NA | NA | NA | 4129 |
| 7907v20141116 | regulator | 3602 | 151 | 1225 | NA | NA | 3602 | NA |
| 7912v20141116 | Asp/Glu/hydantoin racemase | 1226 | 153 | 1226 | 2218 | NA | NA | NA |
| 7913v20141116 | D-lactate dehydrogenase | 154 | 154 | 1227 | NA | NA | NA | 4130 |
| 8031v20141116 | hypothetical protein | 155 | 155 | 1231 | 2221 | NA | NA | NA |
| 8053v20141116 | acetyltransferase | 158 | 158 | 1234 | NA | NA | NA | 4143 |
| 8056v20141116 | amidohydrolase | 159 | 159 | 1235 | 2222 | NA | NA | NA |
| 8057v20141116 | ABC transporter | 160 | 160 | 1236 | 2223 | NA | NA | NA |
| 8058v20141116 | ABC transporter permease | 161 | 161 | 1237 | 2224 | NA | NA | NA |
| 8059v20141116 | putative ABC transporter periplasmic substrate-binding protein | 162 | 162 | 1238 | 2225 | NA | NA | NA |
| 8080v20141116 | hypothetical protein | 163 | 163 | 1239 | NA | NA | NA | 4145 |
| 8083v20141116 | N-ethylammeline chlorohydrolase | 164 | 164 | 1240 | 2226 | NA | NA | NA |
| 8084v20141116 | hydantoin racemase | 165 | 165 | 1241 | 2227 | NA | NA | NA |
| 8095v20141116 | glucose-methanol-choline oxidoreductase | 2228 | 169 | 1242 | 2228 | NA | NA | NA |
| 8099v20141116 | Asp/Glu/hydantoin racemase | 2229 | 172 | 1244 | 2229 | NA | NA | NA |
| 8114v20141116 | polysaccharide deacetylase | 175 | 175 | 1245 | NA | NA | NA | 4150 |
| 8273v20141116 | ABC transporter permease | 2234 | 186 | 1255 | 2234 | NA | NA | NA |
| 8289v20141116 | hypothetical protein | 2235 | 188 | 1257 | 2235 | NA | NA | NA |
| 8300v20141116 | Holliday junction DNA helicase RuvB | 191 | 191 | 1259 | NA | NA | NA | 4168 |
| 8303v20141116 | amidase | 1260 | 193 | 1260 | 2236 | NA | NA | NA |
| 8310v20141116 | monooxygenase | 195 | 195 | 1262 | NA | NA | NA | 4170 |
| 8318v20141116 | hypothetical protein | 200 | 200 | 1267 | NA | NA | NA | 4174 |
| 8331v20141116 | hypothetical protein | 202 | 202 | 1268 | NA | NA | NA | 4175 |
| 8335v20141116 | hypothetical protein | 4176 | 205 | 1271 | NA | NA | NA | 4176 |
| 8475v20141116 | hypothetical protein | 210 | 210 | 1276 | 2249 | NA | NA | NA |
| 8524v20141116 | oxidoreductase | 215 | 215 | 1280 | NA | NA | NA | 4190 |
| 8538v20141116 | dehydrogenase | 218 | 218 | 1283 | 2250 | NA | NA | NA |
| 8539v20141116 | AraC family transcriptional regulator | 2251 | 219 | 1284 | 2251 | NA | NA | NA |
| 8573v20141116 | alkanal monooxygenase | 221 | 221 | 1286 | NA | NA | NA | 4191 |
| 8579v20141116 | hypothetical protein | 223 | 223 | 1287 | NA | NA | NA | 4192 |
| 8592v20141116 | hydroxymethylglutaryl-CoA lyase | 226 | 226 | 1289 | 2255 | NA | NA | NA |
| 8593v20141116 | hypothetical protein | 3631 | 227 | 1290 | NA | NA | 3631 | NA |
| 8599v20141116 | hypothetical protein | 2939 | 229 | 1292 | NA | 2939 | NA | NA |

TABLE 7-continued

Orthologous Gene Groups

| Unique Ortholog Group Identifier | Annotation | Reference. Ortholog SEQ ID NO: | NLS0017 Ortholog SEQ ID NO: | NLS0020 Ortholog SEQ ID NO: | NLS0037 Ortholog SEQ ID NO: | NLS0042 Ortholog SEQ ID NO: | NLS0065 Ortholog SEQ ID NO: | NLS0066 Ortholog SEQ ID NO: |
|---|---|---|---|---|---|---|---|---|
| 8603v20141116 | GntR family transcriptional regulator | 232 | 232 | 1294 | 2256 | NA | NA | NA |
| 8642v20141116 | binding-protein-dependent transport system inner membrane protein | 235 | 235 | 1297 | 2257 | NA | NA | NA |
| 8643v20141116 | ABC transporter permease | 2258 | 236 | 1298 | 2258 | NA | NA | NA |
| 8644v20141116 | ABC transporter substrate-binding protein | 237 | 237 | 1299 | 2259 | NA | NA | NA |
| 8867v20141116 | hypothetical protein | 244 | 244 | 1305 | NA | 2969 | NA | NA |
| 8906v20141116 | methylcrotonoyl-CoA carboxylase | 254 | 254 | 1312 | 2265 | NA | NA | NA |
| 8907v20141116 | TetR family transcriptional regulator | 2266 | 255 | 1313 | 2266 | NA | NA | NA |
| 8922v20141116 | response regulator receiver protein | 4206 | 257 | 1315 | NA | NA | NA | 4206 |
| 8932v20141116 | transthyretin | 266 | 266 | 1319 | 2267 | NA | NA | NA |
| 8957v20141116 | hypothetical protein | 274 | 274 | 1327 | NA | NA | 3647 | NA |
| 9274v20141116 | hypothetical protein Mrad2831_4275 | 2278 | 291 | 1350 | 2278 | NA | NA | NA |
| 9275v20141116 | 3-methylcrotonyl-CoA carboxylase subunit alpha | 2279 | 292 | 1351 | 2279 | NA | NA | NA |
| 9277v20141116 | transposase | 293 | 293 | 1352 | NA | NA | NA | 4244 |
| 9280v20141116 | glycosyltransferase | 2990 | 295 | 1354 | NA | 2990 | NA | NA |
| 9320v20141116 | hydrolase | 314 | 314 | 1365 | 2283 | NA | NA | NA |
| 9324v20141116 | hypothetical protein | 316 | 316 | 1367 | NA | NA | 3664 | NA |
| 9342v20141116 | hypothetical protein | 2284 | NA | 1372 | 2284 | NA | 3665 | NA |
| 9755v20141116 | hypothetical protein | 362 | 362 | 1419 | 2290 | NA | NA | NA |
| 9774v20141116 | ATPase | 1424 | 374 | 1424 | NA | NA | 3678 | NA |
| 9781v20141116 | UDP-glucosyltransferase | 2292 | 376 | 1426 | 2292 | NA | NA | NA |
| 10245v20141116 | acetolactate synthase | 393 | 393 | 1448 | 2303 | NA | NA | NA |
| 10246v20141116 | GntR family transcriptional regulator | 2304 | 394 | 1449 | 2304 | NA | NA | NA |
| 10263v20141116 | hypothetical protein | 409 | 409 | 1463 | 2305 | NA | NA | NA |
| 10329v20141116 | fatty acid--CoA ligase | 456 | 456 | 1507 | 2309 | NA | NA | NA |
| 10348v20141116 | None | 469 | 469 | 1517 | NA | NA | 3694 | NA |
| 11120v20141116 | hypothetical protein | 577 | 577 | 1629 | 2319 | NA | NA | NA |
| 15411v20141116 | NAD-binding 6-phosphogluconate dehydrogenase | 925 | 925 | 2062 | 2369 | NA | NA | NA |
| 4672v20141116 | heme peroxidase with hemolysin-type calcium-binding domain | 3351 | NA | NA | NA | 2466 | 3351 | NA |
| 4897v20141116 | elongation factor Tu | 2489 | NA | NA | NA | 2489 | NA | 3970 |
| 5002v20141116 | thiol-disulfide oxidoreductase | 2498 | NA | NA | NA | 2498 | 3375 | NA |
| 5040v20141116 | AraC family transcriptional regulator | 2501 | NA | NA | NA | 2501 | NA | 3976 |
| 5079v20141116 | flagellar hook-length control protein | 3379 | NA | NA | NA | 2503 | 3379 | NA |
| 5117v20141116 | hypothetical protein | 3382 | NA | NA | NA | 2507 | 3382 | NA |
| 5119v20141116 | multidrug ABC transporter ATP-binding protein | 3384 | NA | NA | NA | 2509 | 3384 | NA |
| 5147v20141116 | hypothetical protein Mpop_1464 | 2511 | NA | NA | NA | 2511 | NA | 3981 |
| 5180v20141116 | glycoside hydrolase family 3 | 3386 | NA | NA | NA | 2512 | 3386 | NA |
| 5184v20141116 | hypothetical protein | 2514 | NA | NA | NA | 2514 | NA | 3982 |
| 5205v20141116 | DNA invertase gene rlgA | 34 | 34 | NA | NA | NA | NA | 3984 |

TABLE 7-continued

Orthologous Gene Groups

| Unique Ortholog Group Identifier | Annotation | Reference. Ortholog SEQ ID NO: | NLS0017 Ortholog SEQ ID NO: | NLS0020 Ortholog SEQ ID NO: | NLS0037 Ortholog SEQ ID NO: | NLS0042 Ortholog SEQ ID NO: | NLS0065 Ortholog SEQ ID NO: | NLS0066 Ortholog SEQ ID NO: |
|---|---|---|---|---|---|---|---|---|
| 5219v20141116 | hypothetical protein MexAM1_META1p0208 | 3986 | NA | NA | NA | 2518 | NA | 3986 |
| 5228v20141116 | ABC transporter permease | 3390 | NA | NA | NA | 2519 | 3390 | NA |
| 5233v20141116 | membrane protein | 3391 | NA | NA | NA | 2520 | 3391 | NA |
| 5275v20141116 | gamma-glutamyltransferase | 2524 | NA | NA | NA | 2524 | 3395 | NA |
| 5284v20141116 | hypothetical protein MexAM1_META1p3378 | 2526 | NA | NA | NA | 2526 | 3397 | NA |
| 5287v20141116 | FAD linked oxidase domain-containing protein | 2527 | NA | NA | NA | 2527 | 3398 | NA |
| 5289v20141116 | Siderophore synthetase component | 2528 | NA | NA | NA | 2528 | 3399 | NA |
| 5318v20141116 | hypothetical protein Mpop_4361 | 2529 | NA | NA | NA | 2529 | NA | 3989 |
| 5335v20141116 | AraC family transcriptional regulator | 3990 | NA | NA | NA | 2531 | NA | 3990 |
| 5337v20141116 | hypothetical protein Mpop_4929 | 2532 | NA | NA | NA | 2532 | 3400 | NA |
| 5379v20141116 | hypothetical protein MexAM1_META1p2104 | 2535 | NA | NA | NA | 2535 | 3402 | NA |
| 5381v20141116 | 4Fe—4S ferredoxin | 3403 | NA | NA | NA | 2537 | 3403 | NA |
| 5382v20141116 | hypothetical protein METDI4726 | 3404 | NA | NA | NA | 2538 | 3404 | NA |
| 5383v20141116 | hypothetical protein Mext_3764 | 2539 | NA | NA | NA | 2539 | 3405 | NA |
| 5384v20141116 | N-acetyltransferase GCN5 | 3406 | NA | NA | NA | 2540 | 3406 | NA |
| 5390v20141116 | hypothetical protein | 3993 | NA | NA | NA | 2541 | NA | 3993 |
| 5392v20141116 | hypothetical protein Mext_3467 | 3408 | NA | NA | NA | 2544 | 3408 | NA |
| 5398v20141116 | hypothetical protein Mchl_3886 | 2545 | NA | NA | NA | 2545 | 3409 | NA |
| 5419v20141116 | diguanylate cyclase | 3410 | NA | NA | NA | 2546 | 3410 | NA |
| 5437v20141116 | hypothetical protein Mpop_2189 | 2548 | NA | NA | NA | 2548 | 3414 | NA |
| 5466v20141116 | hypothetical protein Mpop_0206 | 2549 | NA | NA | NA | 2549 | 3415 | NA |
| 5475v20141116 | conserved hypothetical protein | 2552 | NA | NA | NA | 2552 | NA | 4000 |
| 5476v20141116 | hypothetical protein AZOLI_p40379 | 4001 | NA | NA | NA | 2553 | NA | 4001 |
| 5477v20141116 | HAD-superfamily hydrolase | 2554 | NA | NA | NA | 2554 | 3418 | NA |
| 5480v20141116 | hypothetical protein METDI4261 | 3419 | NA | NA | NA | 2555 | 3419 | NA |
| 5482v20141116 | hypothetical protein MexAM1_META1p3862 | 2556 | NA | NA | NA | 2556 | 3420 | NA |
| 5483v20141116 | hypothetical protein | 3421 | NA | NA | NA | 2557 | 3421 | NA |
| 5488v20141116 | fatty acid desaturase; membrane protein | 2559 | NA | NA | NA | 2559 | 3423 | NA |
| 5490v20141116 | hypothetical protein MexAM1_META1p1300 | 2560 | NA | NA | NA | 2560 | 3424 | NA |
| 5524v20141116 | hypothetical protein | 3432 | NA | NA | NA | 2564 | 3432 | NA |
| 5525v20141116 | hypothetical protein Mpop_5158 | 2565 | NA | NA | NA | 2565 | 3433 | NA |
| 5526v20141116 | hypothetical protein Mext_4623 | 2566 | NA | NA | NA | 2566 | 3434 | NA |
| 5530v20141116 | Bacterial extracellular solute-binding protein family 3 | 4009 | NA | NA | NA | 2567 | NA | 4009 |
| 5536v20141116 | hypothetical protein | 2568 | NA | NA | NA | 2568 | 3435 | NA |
| 5543v20141116 | xylose isomerase domain-containing protein | 2569 | NA | NA | NA | 2569 | 3436 | NA |
| 5546v20141116 | hypothetical protein MexAM1_META1p0483 | 3437 | NA | NA | NA | 2570 | 3437 | NA |
| 5556v20141116 | diguanylate cyclase | 3438 | NA | NA | NA | 2571 | 3438 | NA |
| 5568v20141116 | protein transcription factor | 3440 | NA | NA | NA | NA | 3440 | 4011 |

TABLE 7-continued

Orthologous Gene Groups

| Unique Ortholog Group Identifier | Annotation | Reference. Ortholog SEQ ID NO: | NLS0017 Ortholog SEQ ID NO: | NLS0020 Ortholog SEQ ID NO: | NLS0037 Ortholog SEQ ID NO: | NLS0042 Ortholog SEQ ID NO: | NLS0065 Ortholog SEQ ID NO: | NLS0066 Ortholog SEQ ID NO: |
|---|---|---|---|---|---|---|---|---|
| 5577v20141116 | hypothetical protein Mpop__1561 | 2573 | NA | NA | NA | 2573 | 3441 | NA |
| 5578v20141116 | sodium:solute symporter | 2574 | NA | NA | NA | 2574 | 3442 | NA |
| 5610v20141116 | hypothetical protein Mchl__2392 | 2575 | NA | NA | NA | 2575 | 3445 | NA |
| 5612v20141116 | hypothetical protein MexAM1__META1p5060 | 2576 | NA | NA | NA | 2576 | 3446 | NA |
| 5618v20141116 | hypothetical protein | 3447 | NA | NA | NA | 2577 | 3447 | NA |
| 5619v20141116 | hypothetical protein MexAM1__META1p2965 | 3448 | NA | NA | NA | 2578 | 3448 | NA |
| 5625v20141116 | hypothetical protein Mchl__4383 | 2580 | NA | NA | NA | 2580 | 3449 | NA |
| 5626v20141116 | hypothetical protein Mext__3503 | 3450 | NA | NA | NA | 2581 | 3450 | NA |
| 5627v20141116 | protein-L-isoaspartate O-methyltransferase | 2582 | NA | NA | NA | 2582 | 3451 | NA |
| 5628v20141116 | hypothetical protein | 2583 | NA | NA | NA | 2583 | 3452 | NA |
| 5635v20141116 | hypothetical protein Mext__4188 | 2584 | NA | NA | NA | 2584 | 3453 | NA |
| 5636v20141116 | hypothetical protein Mpop__4705 | 2585 | NA | NA | NA | 2585 | 3454 | NA |
| 5642v20141116 | hypothetical protein METDI0650 | 4014 | NA | NA | NA | NA | 3455 | 4014 |
| 5650v20141116 | ATPase | 2586 | NA | NA | NA | 2586 | 3456 | NA |
| 5657v20141116 | two component LuxR family transcriptional regulator | 2587 | NA | NA | NA | 2587 | 3457 | NA |
| 5672v20141116 | hypothetical protein MexAM1__META1p1076 | 2588 | NA | NA | NA | 2588 | 3459 | NA |
| 5679v20141116 | acetate kinase | 2589 | NA | NA | NA | 2589 | 3461 | NA |
| 5684v20141116 | hypothetical protein | 2591 | NA | NA | NA | 2591 | NA | 4015 |
| 5686v20141116 | EAL domain-containing protein | 2592 | NA | NA | NA | 2592 | 3463 | NA |
| 5689v20141116 | AsnC family transcriptional regulator | 2593 | NA | NA | NA | 2593 | 3464 | NA |
| 5691v20141116 | hypothetical protein Mchl__3961 | 2594 | NA | NA | NA | 2594 | 3465 | NA |
| 5692v20141116 | two-component LuxR family transcriptional regulator | 2595 | NA | NA | NA | 2595 | 3466 | NA |
| 5693v20141116 | hypothetical protein Mpop__0877 | 2596 | NA | NA | NA | 2596 | 3467 | NA |
| 5695v20141116 | secretion protein HlyD | 2598 | NA | NA | NA | 2598 | 3468 | NA |
| 5698v20141116 | hypothetical protein Mext__0717 | 3469 | NA | NA | NA | 2599 | 3469 | NA |
| 5699v20141116 | transcriptional regulator | 2600 | NA | NA | NA | 2600 | 3470 | NA |
| 5712v20141116 | HlyD family type I secretion membrane fusion protein | 2602 | NA | NA | NA | 2602 | 3471 | NA |
| 5735v20141116 | integrase catalytic subunit | 55 | 55 | 1132 | NA | NA | NA | NA |
| 5737v20141116 | putative transposase | 2185 | NA | 1133 | 2185 | NA | NA | NA |
| 5745v20141116 | hypothetical protein Mpop__0065 | 4017 | NA | NA | NA | 2606 | NA | 4017 |
| 5752v20141116 | hypothetical protein Mpop__0858 | 2610 | NA | NA | NA | 2610 | 3472 | NA |
| 5756v20141116 | hypothetical protein Mext__1191 | 2612 | NA | NA | NA | 2612 | 3473 | NA |
| 5783v20141116 | rhizobiocin secretion protein rspD | 2618 | NA | NA | NA | 2618 | 3475 | NA |
| 5802v20141116 | hypothetical protein Mext__3619 | 3477 | NA | NA | NA | 2620 | 3477 | NA |
| 5803v20141116 | NADP-dependent alcohol dehydrogenase | 2621 | NA | NA | NA | 2621 | 3478 | NA |
| 5812v20141116 | Urease accessory protein UreD | 2625 | NA | NA | NA | 2625 | 3479 | NA |
| 5813v20141116 | urea transporter | 2626 | NA | NA | NA | 2626 | 3480 | NA |
| 5814v20141116 | ammonium transporter | 2627 | NA | NA | NA | 2627 | 3481 | NA |

TABLE 7-continued

Orthologous Gene Groups

| Unique Ortholog Group Identifier | Annotation | Reference. Ortholog SEQ ID NO: | NLS0017 Ortholog SEQ ID NO: | NLS0020 Ortholog SEQ ID NO: | NLS0037 Ortholog SEQ ID NO: | NLS0042 Ortholog SEQ ID NO: | NLS0065 Ortholog SEQ ID NO: | NLS0066 Ortholog SEQ ID NO: |
|---|---|---|---|---|---|---|---|---|
| 5822v20141116 | hypothetical protein MexAM1_META1p3379 | 2628 | NA | NA | NA | 2628 | 3482 | NA |
| 5845v20141116 | hypothetical protein Mpop_0716 | 2630 | NA | NA | 2186 | 2630 | NA | NA |
| 5859v20141116 | hemolysin-type calcium-binding protein | 3486 | NA | NA | NA | 2632 | 3486 | NA |
| 5866v20141116 | hypothetical protein Mchl_1323 | 3487 | NA | NA | NA | 2633 | 3487 | NA |
| 5872v20141116 | hypothetical protein Mpop_3121 | 2636 | NA | NA | NA | 2636 | 3488 | NA |
| 5881v20141116 | hypothetical protein Mpop_1945 | 2187 | NA | NA | 2187 | 2638 | NA | NA |
| 5884v20141116 | urease subunit gamma | 3489 | NA | NA | NA | 2640 | 3489 | NA |
| 5885v20141116 | urease subunit beta | 2641 | NA | NA | NA | 2641 | 3490 | NA |
| 5886v20141116 | camphor resistance protein CrcB | 2642 | NA | NA | NA | 2642 | 3491 | NA |
| 5887v20141116 | UreE urease accessory domain-containing protein | 3492 | NA | NA | NA | 2643 | 3492 | NA |
| 5888v20141116 | urease accessory protein UreF | 2644 | NA | NA | NA | 2644 | 3493 | NA |
| 5889v20141116 | urease accessory protein UreG | 3494 | NA | NA | NA | 2645 | 3494 | NA |
| 5890v20141116 | hypothetical protein | 3495 | NA | NA | NA | 2646 | 3495 | NA |
| 5934v20141116 | carbon monoxide dehydrogenase subunit G | 58 | 58 | 1135 | NA | NA | NA | NA |
| 5937v20141116 | hypothetical protein | 59 | 59 | NA | NA | 2662 | NA | NA |
| 5952v20141116 | nucleotidyltransferase | 4020 | NA | NA | NA | 2664 | NA | 4020 |
| 5958v20141116 | hypothetical protein Mpop_2489 | 3498 | NA | NA | NA | 2668 | 3498 | NA |
| 5963v20141116 | camphor resistance CrcB protein | 3499 | NA | NA | NA | 2670 | 3499 | NA |
| 5964v20141116 | acid-resistance protein | 2671 | NA | NA | NA | 2671 | 3500 | NA |
| 5970v20141116 | hypothetical protein | 3501 | NA | NA | NA | 2672 | 3501 | NA |
| 5976v20141116 | hypothetical protein Mext_2198 | 2188 | NA | NA | 2188 | 2673 | NA | NA |
| 6008v20141116 | chloride channel protein | 2678 | NA | NA | NA | 2678 | 3503 | NA |
| 6037v20141116 | hypothetical protein Mext_2029 | 2681 | NA | NA | NA | 2681 | NA | 4022 |
| 6040v20141116 | diguanylate cyclase | 2682 | NA | NA | NA | 2682 | 3505 | NA |
| 6045v20141116 | hypothetical protein Mpop_3879 | 3506 | NA | NA | NA | NA | 3506 | 4023 |
| 6100v20141116 | N-acetyltransferase GCN5 | 2684 | NA | NA | NA | 2684 | 3507 | NA |
| 6123v20141116 | TetR family transcriptional regulator | 66 | 66 | 1143 | NA | NA | NA | NA |
| 6155v20141116 | hypothetical protein Mext_0184 | 3508 | NA | NA | NA | 2690 | 3508 | NA |
| 6156v20141116 | hypothetical protein MexAM1_META1p2841 | 2691 | NA | NA | NA | 2691 | 3509 | NA |
| 6179v20141116 | hypothetical protein METDI1994 | 2694 | NA | NA | NA | 2694 | 3510 | NA |
| 6180v20141116 | oleate hydratase | 2695 | NA | NA | NA | 2695 | 3511 | NA |
| 6182v20141116 | hypothetical protein Mext_4657 | 2696 | NA | NA | NA | 2696 | 3512 | NA |
| 6187v20141116 | hypothetical protein Mpop_4217 | 2699 | NA | NA | NA | 2699 | NA | 4029 |
| 6198v20141116 | hypothetical protein Mchl_4111 | 2701 | NA | NA | NA | 2701 | NA | 4030 |
| 6211v20141116 | LysR family transcriptional regulator | 2702 | 69 | NA | NA | 2702 | NA | NA |
| 6228v20141116 | MucR family transcriptional regulator | 2704 | NA | NA | NA | 2704 | 3514 | NA |
| 6266v20141116 | hypothetical protein Mpop_4875 | 2707 | NA | NA | NA | 2707 | 3515 | NA |
| 6267v20141116 | hypothetical protein Mpop_0711 | 2708 | NA | NA | NA | 2708 | 3516 | NA |

TABLE 7-continued

Orthologous Gene Groups

| Unique Ortholog Group Identifier | Annotation | Reference. Ortholog SEQ ID NO: | NLS0017 Ortholog SEQ ID NO: | NLS0020 Ortholog SEQ ID NO: | NLS0037 Ortholog SEQ ID NO: | NLS0042 Ortholog SEQ ID NO: | NLS0065 Ortholog SEQ ID NO: | NLS0066 Ortholog SEQ ID NO: |
|---|---|---|---|---|---|---|---|---|
| 6302v20141116 | hypothetical protein Mext_4665 | 2710 | NA | NA | NA | 2710 | 3518 | NA |
| 6316v20141116 | hypothetical protein | 1145 | 71 | 1145 | NA | NA | NA | NA |
| 6323v20141116 | hypothetical protein Mchl_1272 | 2712 | NA | NA | NA | 2712 | NA | 4034 |
| 6355v20141116 | hypothetical protein MexAM1_META1p2729 | 2713 | NA | NA | 2192 | 2713 | NA | NA |
| 6403v20141116 | hypothetical protein | 4036 | NA | NA | 2194 | NA | NA | 4036 |
| 6404v20141116 | hypothetical protein | 4037 | NA | NA | 2195 | NA | NA | 4037 |
| 6405v20141116 | hypothetical protein | 2196 | NA | NA | 2196 | NA | NA | 4038 |
| 6409v20141116 | hypothetical protein | 3519 | NA | NA | NA | 2718 | 3519 | NA |
| 6410v20141116 | putative 2 4 dihydroxyhept-2-ene-1 7-dioic acid aldolase | 3520 | NA | NA | NA | 2719 | 3520 | NA |
| 6412v20141116 | amidohydrolase | 2720 | NA | NA | NA | 2720 | NA | 4039 |
| 6451v20141116 | integrase family protein | 74 | 74 | NA | NA | NA | 3522 | NA |
| 6472v20141116 | hypothetical protein FBFL15_0362 | 2197 | NA | 1148 | 2197 | NA | NA | NA |
| 6475v20141116 | hypothetical protein | 3523 | NA | 1149 | NA | NA | 3523 | NA |
| 6566v20141116 | hypothetical protein Mchl_1240 | 2738 | NA | NA | NA | 2738 | NA | 4040 |
| 6568v20141116 | hypothetical protein Mchl_4341 | 2740 | NA | NA | NA | 2740 | NA | 4041 |
| 6571v20141116 | hypothetical protein MexAM1_META1p4650 | 3524 | NA | NA | NA | NA | 3524 | 4042 |
| 6576v20141116 | hypothetical protein | 2741 | NA | NA | NA | 2741 | NA | 4043 |
| 6587v20141116 | hypothetical protein METDI5212 | 3525 | NA | NA | NA | 2743 | 3525 | NA |
| 6615v20141116 | hypothetical protein | 1151 | NA | 1151 | NA | NA | 3526 | NA |
| 6616v20141116 | hypothetical protein | 3527 | NA | NA | NA | NA | 3527 | 4044 |
| 6649v20141116 | hypothetical protein | 2748 | NA | NA | NA | 2748 | 3530 | NA |
| 6655v20141116 | hypothetical protein | 3531 | NA | NA | NA | 2751 | 3531 | NA |
| 6656v20141116 | hypothetical protein Mext_0808 | 2753 | NA | NA | NA | 2753 | 3532 | NA |
| 6665v20141116 | hypothetical protein | 2754 | NA | NA | NA | 2754 | NA | 4048 |
| 6670v20141116 | ubiE/COQ5 methyltransferase family enzyme | 2756 | NA | NA | NA | 2756 | 3533 | NA |
| 6713v20141116 | cytochrome C biogenesis protein CcsA | 3535 | NA | NA | NA | NA | 3535 | 4049 |
| 6749v20141116 | hypothetical protein | 1153 | NA | 1153 | NA | NA | 3537 | NA |
| 6750v20141116 | hypothetical protein | 1154 | NA | 1154 | NA | NA | 3538 | NA |
| 6777v20141116 | hypothetical protein | 2200 | NA | NA | 2200 | NA | NA | 4051 |
| 6778v20141116 | choloylglycine hydrolase | 3539 | NA | NA | NA | 2759 | 3539 | NA |
| 6824v20141116 | transposase of ISMex3 IS256 family | 78 | 78 | 1158 | NA | NA | NA | NA |
| 6829v20141116 | hypothetical protein | 2765 | NA | NA | NA | 2765 | 3544 | NA |
| 6832v20141116 | HEPN domain-containing protein | 4055 | NA | NA | NA | 2766 | NA | 4055 |
| 6833v20141116 | regulatory protein LysR | 3546 | NA | NA | NA | 2767 | 3546 | NA |
| 6835v20141116 | hypothetical protein Mchl_5553 | 2202 | NA | NA | 2202 | NA | NA | 4056 |
| 6876v20141116 | fermentative D-lactate dehydrogenase NAD-dependent | 2774 | NA | NA | NA | 2774 | 3553 | NA |
| 6881v20141116 | hypothetical protein | 2777 | NA | NA | NA | 2777 | NA | 4057 |
| 6892v20141116 | hypothetical protein | 2778 | NA | NA | NA | 2778 | NA | 4059 |
| 6923v20141116 | Hypothetical protein | 1159 | 82 | 1159 | NA | NA | NA | NA |
| 6941v20141116 | hypothetical protein Mext_1123 | 2779 | 83 | NA | NA | 2779 | NA | NA |
| 6946v20141116 | hypothetical protein | 1161 | NA | 1161 | NA | NA | NA | 4061 |
| 6982v20141116 | hypothetical protein Mext_1327 | 2790 | NA | NA | NA | 2790 | 3558 | NA |
| 7002v20141116 | esterase | 2794 | NA | NA | NA | 2794 | 3559 | NA |
| 7004v20141116 | hypothetical protein Mpop_1856 | 2795 | NA | NA | NA | 2795 | NA | 4065 |

TABLE 7-continued

Orthologous Gene Groups

| Unique Ortholog Group Identifier | Annotation | Reference. Ortholog SEQ ID NO: | NLS0017 Ortholog SEQ ID NO: | NLS0020 Ortholog SEQ ID NO: | NLS0037 Ortholog SEQ ID NO: | NLS0042 Ortholog SEQ ID NO: | NLS0065 Ortholog SEQ ID NO: | NLS0066 Ortholog SEQ ID NO: |
|---|---|---|---|---|---|---|---|---|
| 7028v20141116 | hypothetical protein | 2797 | NA | NA | NA | 2797 | NA | 4068 |
| 7057v20141116 | hypothetical protein | 3560 | NA | 1169 | NA | NA | 3560 | NA |
| 7068v20141116 | xylose isomerase domain-containing protein | 2801 | NA | NA | NA | 2801 | NA | 4072 |
| 7077v20141116 | NADPH-dependent FMN reductase | 2203 | NA | NA | 2203 | 2802 | NA | NA |
| 7083v20141116 | glutathione S-transferase | 2204 | NA | NA | 2204 | NA | NA | 4073 |
| 7096v20141116 | diguanylate cyclase | 2808 | NA | NA | NA | 2808 | 3563 | NA |
| 7116v20141116 | transposase mutator type | 1170 | 90 | 1170 | NA | NA | NA | NA |
| 7127v20141116 | hypothetical protein Mnod_6985 | 4074 | 94 | NA | NA | NA | NA | 4074 |
| 7149v20141116 | hypothetical protein | 4075 | NA | NA | NA | NA | 3564 | 4075 |
| 7158v20141116 | short-chain dehydrogenase/reductase SDR | 3565 | NA | NA | NA | 2816 | 3565 | NA |
| 7238v20141116 | methyl-accepting chemotaxis sensory transducer | 4078 | NA | NA | NA | NA | 3568 | 4078 |
| 7242v20141116 | flagellar hook length determination protein | 2817 | NA | NA | NA | 2817 | 3570 | NA |
| 7272v20141116 | hypothetical protein MexAM1_META1p0887 | 4079 | NA | NA | NA | 2823 | NA | 4079 |
| 7303v20141116 | glycosyl hydrolase | 2827 | NA | 1182 | NA | 2827 | NA | NA |
| 7316v20141116 | hypothetical protein Mpop_4411 | 4092 | NA | NA | 2207 | NA | NA | 4092 |
| 7318v20141116 | hypothetical protein Mrad2831_3608 | 110 | 110 | 1187 | NA | NA | NA | NA |
| 7330v20141116 | short-chain dehydrogenase/reductase SDR | 2831 | NA | NA | NA | 2831 | NA | 4093 |
| 7334v20141116 | hypothetical protein | 112 | 112 | NA | NA | 2832 | NA | NA |
| 7364v20141116 | IclR family transcriptional regulator | 2833 | NA | NA | NA | 2833 | NA | 4095 |
| 7384v20141116 | hypothetical protein Mpop_4088 | 4096 | NA | NA | NA | NA | 3576 | 4096 |
| 7388v20141116 | hypothetical protein Mpop_4204 | 2834 | NA | NA | NA | 2834 | NA | 4097 |
| 7389v20141116 | peptidase M24 | 2835 | NA | NA | NA | 2835 | NA | 4098 |
| 7390v20141116 | thiamine pyrophosphate protein central region | 2836 | NA | NA | NA | 2836 | NA | 4099 |
| 7399v20141116 | hypothetical protein | 3577 | NA | NA | NA | 2842 | 3577 | NA |
| 7418v20141116 | hypothetical protein | 2209 | NA | NA | 2209 | 2843 | NA | NA |
| 7420v20141116 | hypothetical protein Mchl_5174 | 2844 | NA | NA | NA | 2844 | 3578 | NA |
| 7422v20141116 | hypothetical protein Mext_4882 | 2845 | NA | NA | NA | 2845 | 3579 | NA |
| 7435v20141116 | hypothetical protein | 2852 | NA | NA | NA | 2852 | NA | 4101 |
| 7437v20141116 | hypothetical protein LILAB_22195 | 4102 | NA | NA | NA | NA | 3581 | 4102 |
| 7465v20141116 | hypothetical protein | 3582 | NA | NA | 2210 | NA | 3582 | NA |
| 7482v20141116 | phage putative protein | 1190 | 117 | 1190 | NA | NA | NA | NA |
| 7484v20141116 | hypothetical protein | 119 | 119 | 1191 | NA | NA | NA | NA |
| 7489v20141116 | enoyl-CoA hydratase/isomerase | 120 | 120 | 1192 | NA | NA | NA | NA |
| 7517v20141116 | inner-membrane translocator | 2857 | NA | NA | NA | 2857 | NA | 4105 |
| 7518v20141116 | branched chain amino acid ABC transporter substrate-binding protein | 4106 | NA | NA | NA | 2858 | NA | 4106 |
| 7558v20141116 | hypothetical protein | 3584 | NA | NA | 1195 | NA | 3584 | NA |
| 7562v20141116 | integrase catalytic subunit | 123 | 123 | 1196 | NA | NA | NA | NA |
| 7586v20141116 | hypothetical protein | 3586 | NA | 1198 | NA | NA | 3586 | NA |
| 7587v20141116 | hypothetical protein | 3587 | NA | 1199 | NA | NA | 3587 | NA |

TABLE 7-continued

Orthologous Gene Groups

| Unique Ortholog Group Identifier | Annotation | Reference. Ortholog SEQ ID NO: | NLS0017 Ortholog SEQ ID NO: | NLS0020 Ortholog SEQ ID NO: | NLS0037 Ortholog SEQ ID NO: | NLS0042 Ortholog SEQ ID NO: | NLS0065 Ortholog SEQ ID NO: | NLS0066 Ortholog SEQ ID NO: |
|---|---|---|---|---|---|---|---|---|
| 7588v20141116 | hypothetical protein | 1200 | NA | 1200 | NA | NA | 3588 | NA |
| 7589v20141116 | hypothetical protein | 1201 | NA | 1201 | NA | NA | 3589 | NA |
| 7590v20141116 | hypothetical protein Mrad2831_2637 | 2211 | NA | NA | 2211 | NA | NA | 4107 |
| 7624v20141116 | N-acetyltransferase GCN5 | 2212 | NA | NA | 2212 | 2861 | NA | NA |
| 7699v20141116 | hypothetical protein | 126 | 126 | 1202 | NA | NA | NA | NA |
| 7713v20141116 | hypothetical protein | 129 | 129 | 1205 | NA | NA | NA | NA |
| 7734v20141116 | hypothetical protein Mnod_8620 | 2215 | 132 | NA | 2215 | NA | NA | NA |
| 7748v20141116 | hypothetical protein | 1208 | 133 | 1208 | NA | NA | NA | NA |
| 7749v20141116 | integrase | 134 | 134 | NA | NA | 2875 | NA | NA |
| 7751v20141116 | integrase catalytic subunit | 1210 | 136 | 1210 | NA | NA | NA | NA |
| 7782v20141116 | hypothetical protein | 2878 | NA | NA | NA | 2878 | 3597 | NA |
| 7783v20141116 | GntR family transcriptional regulator | 4116 | NA | NA | NA | 2879 | NA | 4116 |
| 7813v20141116 | None | 2883 | NA | NA | NA | 2883 | NA | 4118 |
| 7814v20141116 | hypothetical protein | 2884 | NA | NA | NA | 2884 | NA | 4119 |
| 7815v20141116 | RNA polymerase subunit sigma-24 | 2885 | NA | NA | NA | 2885 | NA | 4120 |
| 7829v20141116 | hypothetical protein | 1213 | 138 | 1213 | NA | NA | NA | NA |
| 7855v20141116 | hypothetical protein | 141 | 141 | 1216 | NA | NA | NA | NA |
| 7856v20141116 | hypothetical protein | 4125 | 142 | NA | NA | NA | NA | 4125 |
| 7869v20141116 | hypothetical protein Mchl_2588 | 144 | 144 | 1218 | NA | NA | NA | NA |
| 7889v20141116 | hypothetical protein Mnod_5347 | 147 | 147 | 1222 | NA | NA | NA | NA |
| 7899v20141116 | hypothetical protein | 150 | 150 | 1224 | NA | NA | NA | NA |
| 7909v20141116 | hypothetical protein Mpop_3836 | 2217 | 152 | NA | 2217 | NA | NA | NA |
| 7919v20141116 | hypothetical protein | 2895 | NA | 1230 | NA | 2895 | NA | NA |
| 7926v20141116 | hypothetical protein | 3604 | NA | NA | NA | NA | 3604 | 4133 |
| 7931v20141116 | None | 3605 | NA | NA | NA | NA | 3605 | 4134 |
| 7981v20141116 | transposase IS3/IS911 family protein | 2909 | NA | NA | NA | 2909 | NA | 4141 |
| 8024v20141116 | short-chain dehydrogenase/reductase SDR | 3609 | NA | NA | 2220 | NA | 3609 | NA |
| 8042v20141116 | Hypothetical protein | 156 | 156 | 1232 | NA | NA | NA | NA |
| 8052v20141116 | MFS transporter | 157 | 157 | 1233 | NA | NA | NA | NA |
| 8092v20141116 | ABC transporter inner membrane protein | 4146 | 166 | NA | NA | NA | NA | 4146 |
| 8093v20141116 | ABC transporter | 167 | 167 | NA | NA | NA | NA | 4147 |
| 8094v20141116 | nitrate/sulfonate/bicarbonate ABC transporter | 4148 | 168 | NA | NA | NA | NA | 4148 |
| 8098v20141116 | hypothetical protein | 170 | 170 | 1243 | NA | NA | NA | NA |
| 8113v20141116 | adenylate/guanylate cyclase | 4149 | 174 | NA | NA | NA | NA | 4149 |
| 8115v20141116 | integrase family protein | 2910 | 176 | NA | NA | 2910 | NA | NA |
| 8116v20141116 | ISGsu7 transposase OrfA | 177 | 177 | 1246 | NA | NA | NA | NA |
| 8117v20141116 | hypothetical protein Mrad2831_5711 | 178 | 178 | 1247 | NA | NA | NA | NA |
| 8124v20141116 | Mobile element protein | 3611 | NA | 1249 | NA | NA | 3611 | NA |
| 8136v20141116 | hypothetical protein Mpop_2878 | 2230 | NA | NA | 2230 | 2911 | NA | NA |
| 8171v20141116 | hypothetical protein | 4155 | NA | NA | NA | 2912 | NA | 4155 |
| 8179v20141116 | response regulator receiver | 2232 | NA | NA | 2232 | NA | NA | 4156 |
| 8180v20141116 | None | 2233 | NA | NA | 2233 | NA | NA | 4157 |
| 8205v20141116 | hypothetical protein | 2917 | NA | NA | NA | 2917 | NA | 4160 |
| 8206v20141116 | rhodanese | 4161 | NA | NA | NA | 2918 | NA | 4161 |
| 8237v20141116 | integrase family protein | 2919 | NA | NA | NA | 2919 | 3619 | NA |
| 8258v20141116 | hypothetical protein | 180 | 180 | NA | NA | NA | 3620 | NA |
| 8267v20141116 | porin | 181 | 181 | 1250 | NA | NA | NA | NA |
| 8268v20141116 | hypothetical protein Mrad2831_0222 | 182 | 182 | 1251 | NA | NA | NA | NA |

TABLE 7-continued

Orthologous Gene Groups

| Unique Ortholog Group Identifier | Annotation | Reference. Ortholog SEQ ID NO: | NLS0017 Ortholog SEQ ID NO: | NLS0020 Ortholog SEQ ID NO: | NLS0037 Ortholog SEQ ID NO: | NLS0042 Ortholog SEQ ID NO: | NLS0065 Ortholog SEQ ID NO: | NLS0066 Ortholog SEQ ID NO: |
|---|---|---|---|---|---|---|---|---|
| 8269v20141116 | hypothetical protein | 183 | 183 | 1252 | NA | NA | NA | NA |
| 8270v20141116 | two component transcriptional regulator | 184 | 184 | 1253 | NA | NA | NA | NA |
| 8271v20141116 | RND family efflux transporter MFP subunit | 185 | 185 | 1254 | NA | NA | NA | NA |
| 8284v20141116 | thiamine pyrophosphate binding domain-containing protein | 187 | 187 | 1256 | NA | NA | NA | NA |
| 8299v20141116 | hypothetical protein | 190 | 190 | 1258 | NA | NA | NA | NA |
| 8301v20141116 | None | 4169 | 192 | NA | NA | NA | NA | 4169 |
| 8308v20141116 | hypothetical protein | 194 | 194 | 1261 | NA | NA | NA | NA |
| 8311v20141116 | enoyl-CoA hydratase | 196 | 196 | 1263 | NA | NA | NA | NA |
| 8332v20141116 | hypothetical protein BJ6T_24320 | 203 | 203 | 1269 | NA | NA | NA | NA |
| 8334v20141116 | hypothetical protein | 204 | 204 | 1270 | NA | NA | NA | NA |
| 8339v20141116 | ATP-hydrolyzing enzyme | 1272 | NA | 1272 | 2240 | NA | NA | NA |
| 8361v20141116 | plasmid stability protein StbC | 3621 | NA | NA | 2243 | NA | 3621 | NA |
| 8411v20141116 | methyltransferase type 11 | 4180 | NA | NA | NA | NA | 3627 | 4180 |
| 8412v20141116 | oxidoreductase FAD/NAD(P)-binding domain-containing protein | 3628 | NA | NA | NA | NA | 3628 | 4181 |
| 8413v20141116 | hypothetical protein Mchl_5368 | 2929 | NA | NA | NA | 2929 | NA | 4182 |
| 8445v20141116 | integrase family protein | 2937 | NA | NA | NA | 2937 | 3629 | NA |
| 8450v20141116 | hypothetical protein GDI_3938 | 4188 | NA | NA | 2246 | NA | NA | 4188 |
| 8463v20141116 | linear gramicidin synthetase subunit C | 1274 | 208 | 1274 | NA | NA | NA | NA |
| 8468v20141116 | hypothetical protein | 209 | 209 | 1275 | NA | NA | NA | NA |
| 8477v20141116 | hypothetical protein | 211 | 211 | 1277 | NA | NA | NA | NA |
| 8478v20141116 | ABC transporter-like protein | 212 | 212 | 1278 | NA | NA | NA | NA |
| 8479v20141116 | acetamidase | 213 | 213 | 1279 | NA | NA | NA | NA |
| 8535v20141116 | C4-dicarboxylate ABC transporter | 216 | 216 | 1281 | NA | NA | NA | NA |
| 8536v20141116 | nitrate ABC transporter substrate-binding protein | 217 | 217 | 1282 | NA | NA | NA | NA |
| 8572v20141116 | replication protein C | 220 | 220 | 1285 | NA | NA | NA | NA |
| 8583v20141116 | putative radical SAM domain protein | 224 | 224 | NA | 2254 | NA | NA | NA |
| 8588v20141116 | 4-carboxy muconolactone decarboxylase | 225 | 225 | 1288 | NA | NA | NA | NA |
| 8598v20141116 | LysR family transcriptional regulator | 228 | 228 | 1291 | NA | NA | NA | NA |
| 8601v20141116 | hypothetical protein | 231 | 231 | 1293 | NA | NA | NA | NA |
| 8607v20141116 | hypothetical protein | 233 | 233 | 1295 | NA | NA | NA | NA |
| 8631v20141116 | hypothetical protein | 234 | 234 | 1296 | NA | NA | NA | NA |
| 8716v20141116 | hypothetical protein | 3638 | NA | NA | NA | NA | 3638 | 4196 |
| 8826v20141116 | phage integrase | 2960 | NA | NA | 2262 | 2960 | NA | NA |
| 8844v20141116 | transposase ISDvu2 | 239 | 239 | 1300 | NA | NA | NA | NA |
| 8857v20141116 | alpha/beta hydrolase | 241 | 241 | 1302 | NA | NA | NA | NA |
| 8858v20141116 | putative chemotaxis phosphatase CheZ | 242 | 242 | 1303 | NA | NA | NA | NA |
| 8862v20141116 | hypothetical protein Swoo_4771 | 243 | 243 | 1304 | NA | NA | NA | NA |
| 8870v20141116 | methionine gamma-lyase | 246 | 246 | 1306 | NA | NA | NA | NA |
| 8871v20141116 | CoA-binding domain-containing protein | 247 | 247 | NA | NA | 2970 | NA | NA |
| 8892v20141116 | metal dependent phosphohydrolase | 248 | 248 | 1307 | NA | NA | NA | NA |
| 8894v20141116 | hypothetical protein | 249 | 249 | 1308 | NA | NA | NA | NA |

TABLE 7-continued

Orthologous Gene Groups

| Unique Ortholog Group Identifier | Annotation | Reference. Ortholog SEQ ID NO: | NLS0017 Ortholog SEQ ID NO: | NLS0020 Ortholog SEQ ID NO: | NLS0037 Ortholog SEQ ID NO: | NLS0042 Ortholog SEQ ID NO: | NLS0065 Ortholog SEQ ID NO: | NLS0066 Ortholog SEQ ID NO: |
|---|---|---|---|---|---|---|---|---|
| 8900v20141116 | mercuric reductase | 252 | 252 | 1310 | NA | NA | NA | NA |
| 8903v20141116 | MFS transporter | 253 | 253 | 1311 | NA | NA | NA | NA |
| 8908v20141116 | hypothetical protein Mrad2831_1442 | 1314 | 256 | 1314 | NA | NA | NA | NA |
| 8923v20141116 | hypothetical protein Mrad2831_5910 | 258 | 258 | 1316 | NA | NA | NA | NA |
| 8924v20141116 | Xaa-Pro aminopeptidase | 259 | 259 | 1317 | NA | NA | NA | NA |
| 8925v20141116 | hypothetical protein | 260 | 260 | 1318 | NA | NA | NA | NA |
| 8933v20141116 | multi-sensor signal transduction histidine kinase | 267 | 267 | 1320 | NA | NA | NA | NA |
| 8938v20141116 | endoribonuclease L-PSP | 268 | 268 | 1321 | NA | NA | NA | NA |
| 8940v20141116 | hypothetical protein | 269 | 269 | 1322 | NA | NA | NA | NA |
| 8941v20141116 | hypothetical protein | 1323 | 270 | 1323 | NA | NA | NA | NA |
| 8947v20141116 | hypothetical protein | 1324 | 271 | 1324 | NA | NA | NA | NA |
| 8949v20141116 | hypothetical protein Mnod_5935 | 272 | 272 | 1325 | NA | NA | NA | NA |
| 8963v20141116 | ATPase AAA | 4207 | NA | 1328 | NA | NA | NA | 4207 |
| 8968v20141116 | None | 4208 | NA | 1330 | NA | NA | NA | 4208 |
| 8975v20141116 | two component LuxR family transcriptional regulator | 1333 | NA | 1333 | NA | NA | NA | 4209 |
| 9009v20141116 | LysR family transcriptional regulator | 2270 | NA | NA | 2270 | NA | 3651 | NA |
| 9033v20141116 | cobyrinic acid ac-diamide synthase | 2975 | NA | NA | NA | 2975 | NA | 4211 |
| 9049v20141116 | hypothetical protein Mrad2831_5209 | 2272 | NA | NA | 2272 | 2977 | NA | NA |
| 9054v20141116 | hypothetical protein MexAM1_META1p1280 | 3656 | NA | NA | NA | NA | 3656 | 4213 |
| 9082v20141116 | None | 2273 | NA | NA | 2273 | NA | NA | 4214 |
| 9083v20141116 | hypothetical protein | 2274 | NA | NA | 2274 | NA | NA | 4215 |
| 9087v20141116 | short-chain dehydrogenase | 4216 | NA | NA | 2275 | NA | NA | 4216 |
| 9112v20141116 | hypothetical protein | 4221 | NA | NA | NA | NA | 3659 | 4221 |
| 9113v20141116 | hypothetical protein | 3660 | NA | NA | NA | NA | 3660 | 4222 |
| 9114v20141116 | tricarboxylate transporter | 4223 | NA | NA | NA | NA | 3661 | 4223 |
| 9117v20141116 | hypothetical protein Mchl_5371 | 2981 | NA | NA | NA | 2981 | NA | 4225 |
| 9125v20141116 | hypothetical protein Mchl_0715 | 2986 | NA | NA | NA | 2986 | 3662 | NA |
| 9136v20141116 | hypothetical protein Mnod_6346 | 3663 | NA | NA | NA | NA | 3663 | 4235 |
| 9205v20141116 | hypothetical protein | 276 | 276 | 1334 | NA | NA | NA | NA |
| 9230v20141116 | acetyl-CoA acetyltransferase | 278 | 278 | 1336 | NA | NA | NA | NA |
| 9241v20141116 | hypothetical protein | 279 | 279 | 1338 | NA | NA | NA | NA |
| 9245v20141116 | family 1 extracellular solute-binding protein | 281 | 281 | 1339 | NA | NA | NA | NA |
| 9247v20141116 | two-component sensor histidine kinase | 282 | 282 | 1340 | NA | NA | NA | NA |
| 9254v20141116 | carboxymethylenebutenolidase | 283 | 283 | 1342 | NA | NA | NA | NA |
| 9257v20141116 | hypothetical protein | 284 | 284 | 1343 | NA | NA | NA | NA |
| 9260v20141116 | beta-lactamase domain-containing protein | 285 | 285 | 1344 | NA | NA | NA | NA |
| 9261v20141116 | nucleotide sugar dehydrogenase | 286 | 286 | 1345 | NA | NA | NA | NA |
| 9268v20141116 | carbon monoxide dehydrogenase | 287 | 287 | 1346 | NA | NA | NA | NA |
| 9269v20141116 | hypothetical protein | 288 | 288 | 1347 | NA | NA | NA | NA |
| 9270v20141116 | peptidase M19 | 289 | 289 | 1348 | NA | NA | NA | NA |
| 9271v20141116 | hypothetical protein | 1349 | 290 | 1349 | NA | NA | NA | NA |
| 9278v20141116 | hypothetical protein | 294 | 294 | 1353 | NA | NA | NA | NA |
| 9281v20141116 | glycosyl transferase family 1 | 296 | 296 | 1355 | NA | NA | NA | NA |
| 9282v20141116 | substrate-binding protein | 297 | 297 | NA | 2280 | NA | NA | NA |

TABLE 7-continued

Orthologous Gene Groups

| Unique Ortholog Group Identifier | Annotation | Reference. Ortholog SEQ ID NO: | NLS0017 Ortholog SEQ ID NO: | NLS0020 Ortholog SEQ ID NO: | NLS0037 Ortholog SEQ ID NO: | NLS0042 Ortholog SEQ ID NO: | NLS0065 Ortholog SEQ ID NO: | NLS0066 Ortholog SEQ ID NO: |
|---|---|---|---|---|---|---|---|---|
| 9283v20141116 | integral membrane sensor hybrid histidine kinase | 1356 | 298 | 1356 | NA | NA | NA | NA |
| 9284v20141116 | acyltransferase 3 | 299 | 299 | 1357 | NA | NA | NA | NA |
| 9290v20141116 | diguanylate cyclase | 300 | 300 | NA | NA | NA | NA | 4245 |
| 9291v20141116 | hypothetical protein | 301 | 301 | NA | 2281 | NA | NA | NA |
| 9292v20141116 | hypothetical protein | 302 | 302 | NA | 2282 | NA | NA | NA |
| 9295v20141116 | hypothetical protein | 303 | 303 | 1358 | NA | NA | NA | NA |
| 9297v20141116 | hypothetical protein | 1359 | 304 | 1359 | NA | NA | NA | NA |
| 9298v20141116 | hypothetical protein Mrad2831_0240 | 306 | 306 | 1360 | NA | NA | NA | NA |
| 9300v20141116 | nitrate ABC transporter ATP-binding protein | 307 | 307 | 1361 | NA | NA | NA | NA |
| 9309v20141116 | XRE family transcriptional regulator | 4246 | 310 | NA | NA | NA | NA | 4246 |
| 9311v20141116 | Hypothetical protein | 311 | 311 | 1362 | NA | NA | NA | NA |
| 9313v20141116 | hypothetical protein | 1363 | 312 | 1363 | NA | NA | NA | NA |
| 9315v20141116 | hypothetical protein | 313 | 313 | 1364 | NA | NA | NA | NA |
| 9321v20141116 | nucleotidyltransferase | 315 | 315 | 1366 | NA | NA | NA | NA |
| 9331v20141116 | PadR family transcriptional regulator | 317 | 317 | 1368 | NA | NA | NA | NA |
| 9347v20141116 | ABC transporter inner membrane protein | 2994 | NA | 1373 | NA | 2994 | NA | NA |
| 9348v20141116 | hypothetical protein | 4247 | NA | 1374 | NA | NA | NA | 4247 |
| 9467v20141116 | hypothetical protein | 2287 | NA | NA | 2287 | NA | NA | 4253 |
| 9504v20141116 | hypothetical protein Mnod_4882 | 3674 | NA | NA | NA | 3007 | 3674 | NA |
| 9669v20141116 | Hypothetical protein | 1376 | 319 | 1376 | NA | NA | NA | NA |
| 9675v20141116 | conserved hypothetical protein | 3017 | NA | NA | NA | 3017 | 3676 | NA |
| 9680v20141116 | NUDIX hydrolase | 322 | 322 | 1377 | NA | NA | NA | NA |
| 9687v20141116 | polysaccharide biosynthesis protein | 323 | 323 | 1378 | NA | NA | NA | NA |
| 9689v20141116 | fumarylacetoacetate (FAA) hydrolase | 324 | 324 | 1380 | NA | NA | NA | NA |
| 9690v20141116 | hypothetical protein Mrad2831_3421 | 325 | 325 | 1381 | NA | NA | NA | NA |
| 9692v20141116 | muconolactone delta-isomerase | 327 | 327 | 1382 | NA | NA | NA | NA |
| 9693v20141116 | shkimate dehydrogenase | 328 | 328 | 1383 | NA | NA | NA | NA |
| 9694v20141116 | alcohol dehydrogenase | 329 | 329 | 1384 | NA | NA | NA | NA |
| 9695v20141116 | TadE family protein | 330 | 330 | 1385 | NA | NA | NA | NA |
| 9696v20141116 | hypothetical protein | 331 | 331 | 1386 | NA | NA | NA | NA |
| 9698v20141116 | hypothetical protein | 332 | 332 | 1388 | NA | NA | NA | NA |
| 9701v20141116 | membrane protein | 333 | 333 | 1389 | NA | NA | NA | NA |
| 9702v20141116 | MFS transporter | 334 | 334 | 1390 | NA | NA | NA | NA |
| 9703v20141116 | Transcriptional regulator GntR family | 335 | 335 | 1391 | NA | NA | NA | NA |
| 9707v20141116 | hypothetical protein | 336 | 336 | 1392 | NA | NA | NA | NA |
| 9708v20141116 | phosphate ABC transporter substrate-binding protein | 337 | 337 | 1393 | NA | NA | NA | NA |
| 9709v20141116 | ferredoxin | 338 | 338 | 1394 | NA | NA | NA | NA |
| 9710v20141116 | hypothetical protein Mrad2831_0220 | 339 | 339 | 1395 | NA | NA | NA | NA |
| 9712v20141116 | hypothetical protein | 340 | 340 | 1396 | NA | NA | NA | NA |
| 9717v20141116 | GntR family transcriptional regulator | 1397 | 342 | 1397 | NA | NA | NA | NA |
| 9718v20141116 | hypothetical protein | 1398 | 343 | 1398 | NA | NA | NA | NA |
| 9719v20141116 | monooxygenase FAD-binding protein | 344 | 344 | 1400 | NA | NA | NA | NA |
| 9720v20141116 | hypothetical protein Mrad2831_1283 | 345 | 345 | 1401 | NA | NA | NA | NA |
| 9725v20141116 | hypothetical protein | 1402 | 347 | 1402 | NA | NA | NA | NA |
| 9727v20141116 | hypothetical protein | 348 | 348 | 1403 | NA | NA | NA | NA |
| 9728v20141116 | hypothetical protein | 349 | 349 | 1404 | NA | NA | NA | NA |
| 9730v20141116 | hypothetical protein | 350 | 350 | 1405 | NA | NA | NA | NA |
| 9731v20141116 | amidase | 351 | 351 | 1406 | NA | NA | NA | NA |
| 9732v20141116 | hypothetical protein | 352 | 352 | 1407 | NA | NA | NA | NA |

TABLE 7-continued

Orthologous Gene Groups

| Unique Ortholog Group Identifier | Annotation | Reference. Ortholog SEQ ID NO: | NLS0017 Ortholog SEQ ID NO: | NLS0020 Ortholog SEQ ID NO: | NLS0037 Ortholog SEQ ID NO: | NLS0042 Ortholog SEQ ID NO: | NLS0065 Ortholog SEQ ID NO: | NLS0066 Ortholog SEQ ID NO: |
|---|---|---|---|---|---|---|---|---|
| 9735v20141116 | hypothetical protein | 353 | 353 | 1408 | NA | NA | NA | NA |
| 9736v20141116 | methyl-accepting chemotaxis protein | 1409 | NA | 1409 | NA | NA | NA | 4279 |
| 9739v20141116 | hypothetical protein | 354 | 354 | 1410 | NA | NA | NA | NA |
| 9744v20141116 | hypothetical protein | 355 | 355 | 1411 | NA | NA | NA | NA |
| 9745v20141116 | alpha/beta hydrolase fold protein | 356 | 356 | 1413 | NA | NA | NA | NA |
| 9749v20141116 | hypothetical protein Mrad2831_1349 | 357 | 357 | 1414 | NA | NA | NA | NA |
| 9750v20141116 | carbon monoxide dehydrogenase | 358 | 358 | 1415 | NA | NA | NA | NA |
| 9751v20141116 | hypothetical protein | 1416 | 359 | 1416 | NA | NA | NA | NA |
| 9752v20141116 | glyoxalase | 360 | 360 | 1417 | NA | NA | NA | NA |
| 9754v20141116 | hypothetical protein | 1418 | 361 | 1418 | NA | NA | NA | NA |
| 9759v20141116 | hypothetical protein | 366 | 366 | NA | 2291 | NA | NA | NA |
| 9761v20141116 | UDP-glucose 6-dehydrogenase | 367 | 367 | 1420 | NA | NA | NA | NA |
| 9763v20141116 | Hypothetical protein | 369 | 369 | 1421 | NA | NA | NA | NA |
| 9766v20141116 | LysR family transcriptional regulator | 370 | 370 | 1422 | NA | NA | NA | NA |
| 9769v20141116 | glutathione S-transferase | 371 | 371 | 1423 | NA | NA | NA | NA |
| 9776v20141116 | hypothetical protein Msil_2170 | 4282 | NA | NA | NA | 3019 | NA | 4282 |
| 9778v20141116 | peptidase S8 | 1425 | 375 | 1425 | NA | NA | NA | NA |
| 9787v20141116 | LuxR family transcriptional regulator | 377 | 377 | 1427 | NA | NA | NA | NA |
| 9789v20141116 | hypothetical protein | 378 | 378 | 1428 | NA | NA | NA | NA |
| 9790v20141116 | hypothetical protein | 379 | 379 | 1429 | NA | NA | NA | NA |
| 9791v20141116 | hypothetical protein | 380 | 380 | 1430 | NA | NA | NA | NA |
| 9796v20141116 | cyclic nucleotide-binding protein | 1431 | 382 | 1431 | NA | NA | NA | NA |
| 9802v20141116 | hypothetical protein Mrad2831_5170 | 3679 | NA | 1432 | NA | NA | 3679 | NA |
| 9804v20141116 | Holliday junction ATP-dependent DNA helicase | 4283 | NA | 1433 | NA | NA | NA | 4283 |
| 9989v20141116 | Hypothetical protein | 2297 | NA | NA | 2297 | NA | NA | 4288 |
| 10005v20141116 | Hypothetical protein | 4289 | NA | NA | NA | NA | 3684 | 4289 |
| 10053v20141116 | hypothetical protein Mchl_4474 | 3033 | NA | NA | NA | 3033 | 3690 | NA |
| 10058v20141116 | hypothetical protein Mnod_7738 | 3039 | NA | NA | NA | 3039 | NA | 4296 |
| 10065v20141116 | NAD-dependent malic enzyme mitochondrial | 4302 | NA | NA | NA | NA | 3691 | 4302 |
| 10194v20141116 | RTX toxins and related Ca2+-binding protein | 385 | 385 | NA | NA | NA | NA | 4331 |
| 10195v20141116 | hypothetical protein | 386 | 386 | 1440 | NA | NA | NA | NA |
| 10216v20141116 | hypothetical protein | 388 | 388 | 1442 | NA | NA | NA | NA |
| 10219v20141116 | hypothetical protein | 390 | 390 | 1443 | NA | NA | NA | NA |
| 10247v20141116 | hypothetical protein | 395 | 395 | 1450 | NA | NA | NA | NA |
| 10250v20141116 | hypothetical protein | 1451 | 397 | 1451 | NA | NA | NA | NA |
| 10251v20141116 | hypothetical protein | 398 | 398 | 1452 | NA | NA | NA | NA |
| 10252v20141116 | hypothetical protein | 399 | 399 | 1453 | NA | NA | NA | NA |
| 10253v20141116 | histidine kinase | 400 | 400 | 1454 | NA | NA | NA | NA |
| 10254v20141116 | hypothetical protein Mnod_1661 | 401 | 401 | 1455 | NA | NA | NA | NA |
| 10255v20141116 | peroxidase | 402 | 402 | 1456 | NA | NA | NA | NA |
| 10256v20141116 | sn-glycerol-3-phosphate transporter | 1457 | 403 | 1457 | NA | NA | NA | NA |
| 10257v20141116 | hypothetical protein | 1458 | 404 | 1458 | NA | NA | NA | NA |
| 10258v20141116 | acyl-CoA dehydrogenase | 405 | 405 | 1459 | NA | NA | NA | NA |
| 10259v20141116 | IclR family transcriptional regulator | 406 | 406 | 1460 | NA | NA | NA | NA |
| 10260v20141116 | aldehyde dehydrogenase | 407 | 407 | 1461 | NA | NA | NA | NA |
| 10261v20141116 | Dihydrodipicolinate synthase | 408 | 408 | 1462 | NA | NA | NA | NA |
| 10264v20141116 | hypothetical protein | 410 | 410 | 1464 | NA | NA | NA | NA |

TABLE 7-continued

Orthologous Gene Groups

| Unique Ortholog Group Identifier | Annotation | Reference. Ortholog SEQ ID NO: | NLS0017 Ortholog SEQ ID NO: | NLS0020 Ortholog SEQ ID NO: | NLS0037 Ortholog SEQ ID NO: | NLS0042 Ortholog SEQ ID NO: | NLS0065 Ortholog SEQ ID NO: | NLS0066 Ortholog SEQ ID NO: |
|---|---|---|---|---|---|---|---|---|
| 10265v20141116 | None | 411 | 411 | 1465 | NA | NA | NA | NA |
| 10266v20141116 | hypothetical protein | 412 | 412 | 1466 | NA | NA | NA | NA |
| 10268v20141116 | hypothetical protein Atu3845 | 413 | 413 | 1467 | NA | NA | NA | NA |
| 10269v20141116 | hypothetical protein | 414 | 414 | 1468 | NA | NA | NA | NA |
| 10272v20141116 | hypothetical protein | 1469 | 415 | 1469 | NA | NA | NA | NA |
| 10277v20141116 | TetR family-transcriptional regulator | 417 | 417 | 1470 | NA | NA | NA | NA |
| 10278v20141116 | hypothetical protein | 418 | 418 | 1471 | NA | NA | NA | NA |
| 10280v20141116 | hypothetical protein MexAM1_META2p1146 | 1473 | 420 | 1473 | NA | NA | NA | NA |
| 10282v20141116 | hypothetical protein Mrad2831_4849 | 421 | 421 | 1474 | NA | NA | NA | NA |
| 10283v20141116 | citrate synthase | 422 | 422 | 1475 | NA | NA | NA | NA |
| 10284v20141116 | oxidoreductase | 423 | 423 | 1476 | NA | NA | NA | NA |
| 10285v20141116 | hypothetical protein | 424 | 424 | 1477 | NA | NA | NA | NA |
| 10286v20141116 | hypothetical protein | 1478 | 425 | 1478 | NA | NA | NA | NA |
| 10287v20141116 | major facilitator superfamily protein | 426 | 426 | 1479 | NA | NA | NA | NA |
| 10290v20141116 | hypothetical protein | 1480 | 427 | 1480 | NA | NA | NA | NA |
| 10291v20141116 | MFS transporter | 428 | 428 | 1481 | NA | NA | NA | NA |
| 10292v20141116 | aldehyde dehydrogenase | 429 | 429 | 1482 | NA | NA | NA | NA |
| 10293v20141116 | GntR family transcriptional regulator | 430 | 430 | 1483 | NA | NA | NA | NA |
| 10294v20141116 | thioesterase | 431 | 431 | 1484 | NA | NA | NA | NA |
| 10295v20141116 | hypothetical protein | 432 | 432 | 1485 | NA | NA | NA | NA |
| 10296v20141116 | hypothetical protein | 433 | 433 | 1486 | NA | NA | NA | NA |
| 10298v20141116 | hypothetical protein | 1487 | 434 | 1487 | NA | NA | NA | NA |
| 10299v20141116 | hypothetical protein | 435 | 435 | 1488 | NA | NA | NA | NA |
| 10300v20141116 | MFS transporter | 436 | 436 | 1489 | NA | NA | NA | NA |
| 10301v20141116 | crotonase | 437 | 437 | 1490 | NA | NA | NA | NA |
| 10302v20141116 | AMP-dependent synthetase and ligase | 438 | 438 | 1491 | NA | NA | NA | NA |
| 10303v20141116 | (2Fe—2S)-binding domain-containing protein | 439 | 439 | 1492 | NA | NA | NA | NA |
| 10304v20141116 | transcriptional regulator | 440 | 440 | 1493 | NA | NA | NA | NA |
| 10305v20141116 | hydrolase | 441 | 441 | 1494 | NA | NA | NA | NA |
| 10306v20141116 | twin-arginine translocation pathway signal | 1495 | 442 | 1495 | NA | NA | NA | NA |
| 10307v20141116 | hypothetical protein | 443 | 443 | 1496 | NA | NA | NA | NA |
| 10309v20141116 | hypothetical protein | 444 | 444 | 1497 | NA | NA | NA | NA |
| 10310v20141116 | hypothetical protein | 445 | 445 | 1498 | NA | NA | NA | NA |
| 10313v20141116 | hypothetical protein | 446 | 446 | 1499 | NA | NA | NA | NA |
| 10315v20141116 | hypothetical protein | 1500 | 447 | 1500 | NA | NA | NA | NA |
| 10316v20141116 | group 1 glycosyl transferase | 448 | 448 | 1501 | NA | NA | NA | NA |
| 10317v20141116 | group 1 glycosyl transferase | 449 | 449 | 1502 | NA | NA | NA | NA |
| 10318v20141116 | non-specific protein-tyrosine kinase | 450 | 450 | 1503 | NA | NA | NA | NA |
| 10319v20141116 | hypothetical protein | 1504 | 451 | 1504 | NA | NA | NA | NA |
| 10323v20141116 | AraC family transcriptional regulator | 452 | 452 | NA | 2306 | NA | NA | NA |
| 10324v20141116 | hypothetical protein | 2307 | 453 | NA | 2307 | NA | NA | NA |
| 10326v20141116 | aminotransferase class I/II | 2308 | 454 | NA | 2308 | NA | NA | NA |
| 10328v20141116 | hypothetical protein | 455 | 455 | 1506 | NA | NA | NA | NA |
| 10331v20141116 | acyl-CoA dehydrogenase | 458 | 458 | 1508 | NA | NA | NA | NA |
| 10334v20141116 | hypothetical protein | 459 | 459 | 1509 | NA | NA | NA | NA |
| 10335v20141116 | hypothetical protein Mnod_7733 | 460 | 460 | NA | NA | NA | NA | 4342 |
| 10337v20141116 | hypothetical protein | 1510 | 462 | 1510 | NA | NA | NA | NA |
| 10341v20141116 | glyoxalase/bleomycin resistance protein/dioxygenase | 463 | 463 | 1511 | NA | NA | NA | NA |

TABLE 7-continued

Orthologous Gene Groups

| Unique Ortholog Group Identifier | Annotation | Reference. Ortholog SEQ ID NO: | NLS0017 Ortholog SEQ ID NO: | NLS0020 Ortholog SEQ ID NO: | NLS0037 Ortholog SEQ ID NO: | NLS0042 Ortholog SEQ ID NO: | NLS0065 Ortholog SEQ ID NO: | NLS0066 Ortholog SEQ ID NO: |
|---|---|---|---|---|---|---|---|---|
| 10343v20141116 | CitMHS family citrate/H+ symporter | 1512 | 464 | 1512 | NA | NA | NA | NA |
| 10344v20141116 | ABC transporter substrate-binding protein | 465 | 465 | 1513 | NA | NA | NA | NA |
| 10345v20141116 | beta-lactamase | 466 | 466 | 1514 | NA | NA | NA | NA |
| 10346v20141116 | endoribonuclease L-PSP | 1515 | 467 | 1515 | NA | NA | NA | NA |
| 10347v20141116 | hypothetical protein Mrad2831_4429 | 1516 | 468 | 1516 | NA | NA | NA | NA |
| 10349v20141116 | hypothetical protein | 1518 | 470 | 1518 | NA | NA | NA | NA |
| 10350v20141116 | hypothetical protein | 1519 | 471 | 1519 | NA | NA | NA | NA |
| 10354v20141116 | Hypothetical protein | 4343 | 472 | NA | NA | NA | NA | 4343 |
| 10356v20141116 | Hypothetical protein | 473 | 473 | 1520 | NA | NA | NA | NA |
| 10358v20141116 | hypothetical protein | 474 | 474 | NA | NA | NA | NA | 4345 |
| 10361v20141116 | hypothetical protein Mrad2831_5665 | 1522 | NA | 1522 | NA | NA | NA | 4346 |
| 10655v20141116 | hypothetical protein | 2312 | NA | NA | 2312 | 3049 | NA | NA |
| 10656v20141116 | hypothetical protein Mrad2831_5208 | 2313 | NA | NA | 2313 | 3050 | NA | NA |
| 10675v20141116 | transposase | 3697 | NA | NA | 2314 | NA | 3697 | NA |
| 10688v20141116 | None | 2316 | NA | NA | 2316 | NA | NA | 4354 |
| 10941v20141116 | hypothetical protein | 1529 | 475 | 1529 | NA | NA | NA | NA |
| 10942v20141116 | peptidoglycan-binding protein | 478 | 478 | 1530 | NA | NA | NA | NA |
| 10980v20141116 | hypothetical protein | 1534 | 479 | 1534 | NA | NA | NA | NA |
| 10994v20141116 | hypothetical protein | 1535 | 480 | 1535 | NA | NA | NA | NA |
| 10999v20141116 | hypothetical protein | 482 | 482 | 1536 | NA | NA | NA | NA |
| 11000v20141116 | hypothetical protein | 483 | 483 | 1537 | NA | NA | NA | NA |
| 11001v20141116 | ABC transporter permease | 484 | 484 | 1538 | NA | NA | NA | NA |
| 11002v20141116 | hypothetical protein | 485 | 485 | 1539 | NA | NA | NA | NA |
| 11003v20141116 | 3-ketoacyl-ACP reductase | 486 | 486 | 1540 | NA | NA | NA | NA |
| 11004v20141116 | branched-chain amino acid ABC transporter ATP-binding protein | 487 | 487 | 1541 | NA | NA | NA | NA |
| 11005v20141116 | NADPH quinone oxidoreductase | 488 | 488 | 1542 | NA | NA | NA | NA |
| 11006v20141116 | hypothetical protein | 489 | 489 | 1543 | NA | NA | NA | NA |
| 11007v20141116 | hypothetical protein | 490 | 490 | 1544 | NA | NA | NA | NA |
| 11008v20141116 | aliphatic amidase expression-regulating protein AmiC | 491 | 491 | 1545 | NA | NA | NA | NA |
| 11009v20141116 | hypothetical protein | 492 | 492 | 1546 | NA | NA | NA | NA |
| 11010v20141116 | short-chain dehydrogenase/reductase SDR | 493 | 493 | 1547 | NA | NA | NA | NA |
| 11013v20141116 | hypothetical protein | 494 | 494 | 1548 | NA | NA | NA | NA |
| 11014v20141116 | hypothetical protein | 495 | 495 | 1549 | NA | NA | NA | NA |
| 11015v20141116 | hypothetical protein | 496 | 496 | 1550 | NA | NA | NA | NA |
| 11016v20141116 | ECF subfamily RNA polymerase sigma-24 factor | 497 | 497 | 1551 | NA | NA | NA | NA |
| 11019v20141116 | major facilitator transporter | 498 | 498 | 1552 | NA | NA | NA | NA |
| 11022v20141116 | hypothetical protein Mrad2831_2880 | 499 | 499 | 1553 | NA | NA | NA | NA |
| 11023v20141116 | hypothetical protein | 1554 | 500 | 1554 | NA | NA | NA | NA |
| 11024v20141116 | hypothetical protein | 501 | 501 | 1555 | NA | NA | NA | NA |
| 11025v20141116 | hypothetical protein | 502 | 502 | 1556 | NA | NA | NA | NA |
| 11026v20141116 | None | 503 | 503 | 1557 | NA | NA | NA | NA |
| 11027v20141116 | helicase | 504 | 504 | 1558 | NA | NA | NA | NA |
| 11029v20141116 | Hypothetical protein | 1559 | 506 | 1559 | NA | NA | NA | NA |
| 11030v20141116 | Hypothetical protein | 1560 | 507 | 1560 | NA | NA | NA | NA |
| 11031v20141116 | hypothetical protein Mrad2831_3995 | 508 | 508 | 1561 | NA | NA | NA | NA |
| 11032v20141116 | hypothetical protein | 509 | 509 | 1562 | NA | NA | NA | NA |
| 11033v20141116 | hypothetical protein | 510 | 510 | 1563 | NA | NA | NA | NA |
| 11034v20141116 | hypothetical protein | 511 | 511 | 1564 | NA | NA | NA | NA |

TABLE 7-continued

Orthologous Gene Groups

| Unique Ortholog Group Identifier | Annotation | Reference. Ortholog SEQ ID NO: | NLS0017 Ortholog SEQ ID NO: | NLS0020 Ortholog SEQ ID NO: | NLS0037 Ortholog SEQ ID NO: | NLS0042 Ortholog SEQ ID NO: | NLS0065 Ortholog SEQ ID NO: | NLS0066 Ortholog SEQ ID NO: |
|---|---|---|---|---|---|---|---|---|
| 11035v20141116 | fatty acid hydroxylase | 512 | 512 | 1565 | NA | NA | NA | NA |
| 11036v20141116 | DNA-binding two-component response regulator | 513 | 513 | 1566 | NA | NA | NA | NA |
| 11037v20141116 | hypothetical protein | 514 | 514 | 1567 | NA | NA | NA | NA |
| 11038v20141116 | hypothetical protein | 515 | 515 | 1568 | NA | NA | NA | NA |
| 11040v20141116 | hypothetical protein Mrad2831_4848 | 516 | 516 | 1569 | NA | NA | NA | NA |
| 11041v20141116 | hypothetical protein Mrad2831_4850 | 517 | 517 | 1570 | NA | NA | NA | NA |
| 11042v20141116 | AraC family transcriptional regulator | 518 | 518 | 1571 | NA | NA | NA | NA |
| 11043v20141116 | MucR family transcriptional regulator | 1572 | 519 | 1572 | NA | NA | NA | NA |
| 11044v20141116 | hypothetical protein | 520 | 520 | 1573 | NA | NA | NA | NA |
| 11045v20141116 | hypothetical protein | 521 | 521 | 1574 | NA | NA | NA | NA |
| 11046v20141116 | hypothetical protein | 522 | 522 | 1575 | NA | NA | NA | NA |
| 11047v20141116 | hypothetical protein Mrad2831_4872 | 523 | 523 | 1576 | NA | NA | NA | NA |
| 11048v20141116 | MucR family transcriptional regulator | 524 | 524 | 1577 | NA | NA | NA | NA |
| 11049v20141116 | hypothetical protein | 525 | 525 | 1578 | NA | NA | NA | NA |
| 11050v20141116 | hypothetical protein | 526 | 526 | 1579 | NA | NA | NA | NA |
| 11051v20141116 | hypothetical protein | 1580 | 527 | 1580 | NA | NA | NA | NA |
| 11053v20141116 | hypothetical protein | 528 | 528 | 1581 | NA | NA | NA | NA |
| 11055v20141116 | hypothetical protein | 529 | 529 | 1582 | NA | NA | NA | NA |
| 11056v20141116 | hypothetical protein | 530 | 530 | 1583 | NA | NA | NA | NA |
| 11058v20141116 | CDP-diacylglycerol diphosphatase | 531 | 531 | 1584 | NA | NA | NA | NA |
| 11059v20141116 | hypothetical protein | 532 | 532 | 1585 | NA | NA | NA | NA |
| 11060v20141116 | hypothetical protein | 533 | 533 | 1586 | NA | NA | NA | NA |
| 11062v20141116 | hypothetical protein | 534 | 534 | 1587 | NA | NA | NA | NA |
| 11065v20141116 | hypothetical protein Mrad2831_4173 | 1588 | 535 | 1588 | NA | NA | NA | NA |
| 11066v20141116 | hypothetical protein | 536 | 536 | 1589 | NA | NA | NA | NA |
| 11067v20141116 | hypothetical protein | 1590 | 537 | 1590 | NA | NA | NA | NA |
| 11068v20141116 | hypothetical protein | 538 | 538 | 1591 | NA | NA | NA | NA |
| 11069v20141116 | hypothetical protein | 539 | 539 | 1592 | NA | NA | NA | NA |
| 11071v20141116 | hypothetical protein | 540 | 540 | 1593 | NA | NA | NA | NA |
| 11072v20141116 | hypothetical protein | 541 | 541 | 1594 | NA | NA | NA | NA |
| 11073v20141116 | hypothetical protein | 542 | 542 | 1595 | NA | NA | NA | NA |
| 11074v20141116 | hypothetical protein Mrad2831_2451 | 543 | 543 | 1596 | NA | NA | NA | NA |
| 11075v20141116 | hypothetical protein | 1597 | 544 | 1597 | NA | NA | NA | NA |
| 11077v20141116 | hypothetical protein Mrad2831_4594 | 545 | 545 | 1598 | NA | NA | NA | NA |
| 11078v20141116 | hypothetical protein Mrad2831_4604 | 546 | 546 | 1599 | NA | NA | NA | NA |
| 11079v20141116 | hypothetical protein | 547 | 547 | 1600 | NA | NA | NA | NA |
| 11082v20141116 | hypothetical protein | 548 | 548 | 1601 | NA | NA | NA | NA |
| 11083v20141116 | hypothetical protein | 549 | 549 | 1602 | NA | NA | NA | NA |
| 11085v20141116 | hypothetical protein | 550 | 550 | 1603 | NA | NA | NA | NA |
| 11086v20141116 | methyl-accepting chemotaxis sensory transducer | 1604 | 551 | 1604 | NA | NA | NA | NA |
| 11087v20141116 | hypothetical protein | 1605 | 552 | 1605 | NA | NA | NA | NA |
| 11090v20141116 | hypothetical protein | 1606 | 553 | 1606 | NA | NA | NA | NA |
| 11091v20141116 | hypothetical protein | 554 | 554 | 1607 | NA | NA | NA | NA |
| 11092v20141116 | putative transmembrane protein | 555 | 555 | 1608 | NA | NA | NA | NA |
| 11093v20141116 | hypothetical protein Mrad2831_5620 | 556 | 556 | 1609 | NA | NA | NA | NA |
| 11094v20141116 | hypothetical protein | 557 | 557 | 1610 | NA | NA | NA | NA |
| 11095v20141116 | hypothetical protein Mrad2831_5792 | 558 | 558 | 1611 | NA | NA | NA | NA |
| 11096v20141116 | hypothetical protein | 559 | 559 | 1612 | NA | NA | NA | NA |
| 11097v20141116 | hypothetical protein | 560 | 560 | 1613 | NA | NA | NA | NA |
| 11098v20141116 | hypothetical protein | 561 | 561 | 1614 | NA | NA | NA | NA |
| 11099v20141116 | hypothetical protein | 562 | 562 | 1615 | NA | NA | NA | NA |

TABLE 7-continued

Orthologous Gene Groups

| Unique Ortholog Group Identifier | Annotation | Reference. Ortholog SEQ ID NO: | NLS0017 Ortholog SEQ ID NO: | NLS0020 Ortholog SEQ ID NO: | NLS0037 Ortholog SEQ ID NO: | NLS0042 Ortholog SEQ ID NO: | NLS0065 Ortholog SEQ ID NO: | NLS0066 Ortholog SEQ ID NO: |
|---|---|---|---|---|---|---|---|---|
| 11100v20141116 | hypothetical protein | 563 | 563 | 1616 | NA | NA | NA | NA |
| 11101v20141116 | hypothetical protein | 564 | 564 | 1617 | NA | NA | NA | NA |
| 11102v20141116 | hypothetical protein | 565 | 565 | 1618 | NA | NA | NA | NA |
| 11103v20141116 | HxlR family transcriptional regulator | 566 | 566 | 1619 | NA | NA | NA | NA |
| 11105v20141116 | hypothetical protein Mrad2831_1263 | 567 | 567 | 1620 | NA | NA | NA | NA |
| 11106v20141116 | hypothetical protein Mrad2831_1264 | 568 | 568 | 1621 | NA | NA | NA | NA |
| 11108v20141116 | hypothetical protein | 569 | 569 | 1622 | NA | NA | NA | NA |
| 11109v20141116 | type III effector Hrp-dependent protein | 570 | 570 | 1623 | NA | NA | NA | NA |
| 11110v20141116 | hypothetical protein | 1624 | 571 | 1624 | NA | NA | NA | NA |
| 11114v20141116 | hypothetical protein | 573 | 573 | 1625 | NA | NA | NA | NA |
| 11117v20141116 | hypothetical protein | 574 | 574 | 1626 | NA | NA | NA | NA |
| 11118v20141116 | hypothetical protein | 575 | 575 | 1627 | NA | NA | NA | NA |
| 11119v20141116 | hypothetical protein | 1628 | 576 | 1628 | NA | NA | NA | NA |
| 11121v20141116 | hypothetical protein | 578 | 578 | 1630 | NA | NA | NA | NA |
| 11125v20141116 | hypothetical protein | 581 | 581 | 1631 | NA | NA | NA | NA |
| 11126v20141116 | hypothetical protein Mrad2831_4291 | 582 | 582 | 1632 | NA | NA | NA | NA |
| 11127v20141116 | hypothetical protein | 583 | 583 | 1633 | NA | NA | NA | NA |
| 11128v20141116 | putative aldo/keto reductase protein | 1634 | 584 | 1634 | NA | NA | NA | NA |
| 11129v20141116 | hypothetical protein Mrad2831_1223 | 585 | 585 | 1635 | NA | NA | NA | NA |
| 11130v20141116 | hypothetical protein | 586 | 586 | 1636 | NA | NA | NA | NA |
| 11131v20141116 | hypothetical protein | 587 | 587 | 1637 | NA | NA | NA | NA |
| 11134v20141116 | hypothetical protein | 589 | 589 | 1638 | NA | NA | NA | NA |
| 11136v20141116 | hypothetical protein Mrad2831_4454 | 590 | 590 | 1639 | NA | NA | NA | NA |
| 11137v20141116 | phosphoglycolate phosphatase | 1640 | 591 | 1640 | NA | NA | NA | NA |
| 11138v20141116 | substrate-binding protein | 592 | 592 | 1641 | NA | NA | NA | NA |
| 11139v20141116 | hypothetical protein | 1642 | 593 | 1642 | NA | NA | NA | NA |
| 11140v20141116 | FAD-dependent pyridine nucleotide-disulfide oxidoreductase | 1643 | 594 | 1643 | NA | NA | NA | NA |
| 11141v20141116 | hypothetical protein | 1644 | 595 | 1644 | NA | NA | NA | NA |
| 11142v20141116 | 5-oxopent-3-ene-1 2 5-tricarboxylate decarboxylase | 596 | 596 | 1645 | NA | NA | NA | NA |
| 11143v20141116 | hypothetical protein Mrad2831_1904 | 1646 | 597 | 1646 | NA | NA | NA | NA |
| 11149v20141116 | hypothetical protein | 600 | 600 | 1647 | NA | NA | NA | NA |
| 11150v20141116 | hypothetical protein Mrad2831_1911 | 601 | 601 | 1648 | NA | NA | NA | NA |
| 11151v20141116 | hypothetical protein | 602 | 602 | 1649 | NA | NA | NA | NA |
| 11152v20141116 | hypothetical protein | 603 | 603 | 1650 | NA | NA | NA | NA |
| 11153v20141116 | hypothetical protein | 604 | 604 | 1651 | NA | NA | NA | NA |
| 11154v20141116 | hypothetical protein | 605 | 605 | 1652 | NA | NA | NA | NA |
| 11155v20141116 | hypothetical protein | 606 | 606 | 1653 | NA | NA | NA | NA |
| 11156v20141116 | methyl-accepting chemotaxis sensory transducer | 1654 | 607 | 1654 | NA | NA | NA | NA |
| 11157v20141116 | hypothetical protein | 608 | 608 | 1655 | NA | NA | NA | NA |
| 11161v20141116 | MucR family transcriptional regulator | 610 | 610 | 1656 | NA | NA | NA | NA |
| 11162v20141116 | hypothetical protein | 611 | 611 | 1657 | NA | NA | NA | NA |
| 11164v20141116 | hypothetical protein | 612 | 612 | 1658 | NA | NA | NA | NA |
| 11165v20141116 | MarR family transcriptional regulator | 613 | 613 | 1659 | NA | NA | NA | NA |
| 11167v20141116 | capsule polysaccharide transporter | 614 | 614 | 1660 | NA | NA | NA | NA |
| 11168v20141116 | hypothetical protein | 615 | 615 | 1661 | NA | NA | NA | NA |
| 11169v20141116 | hypothetical protein | 616 | 616 | 1662 | NA | NA | NA | NA |

TABLE 7-continued

Orthologous Gene Groups

| Unique Ortholog Group Identifier | Annotation | Reference. Ortholog SEQ ID NO: | NLS0017 Ortholog SEQ ID NO: | NLS0020 Ortholog SEQ ID NO: | NLS0037 Ortholog SEQ ID NO: | NLS0042 Ortholog SEQ ID NO: | NLS0065 Ortholog SEQ ID NO: | NLS0066 Ortholog SEQ ID NO: |
|---|---|---|---|---|---|---|---|---|
| 11171v20141116 | hypothetical protein | 617 | 617 | 1663 | NA | NA | NA | NA |
| 11172v20141116 | hypothetical protein Mrad2831_1654 | 618 | 618 | 1664 | NA | NA | NA | NA |
| 11176v20141116 | hypothetical protein | 619 | 619 | 1665 | NA | NA | NA | NA |
| 11177v20141116 | hypothetical protein | 620 | 620 | 1666 | NA | NA | NA | NA |
| 11178v20141116 | hypothetical protein | 621 | 621 | 1667 | NA | NA | NA | NA |
| 11180v20141116 | hypothetical protein | 624 | 624 | 1668 | NA | NA | NA | NA |
| 11181v20141116 | hypothetical protein | 625 | 625 | 1669 | NA | NA | NA | NA |
| 11182v20141116 | hypothetical protein | 626 | 626 | 1670 | NA | NA | NA | NA |
| 11183v20141116 | hypothetical protein | 627 | 627 | 1671 | NA | NA | NA | NA |
| 11184v20141116 | hypothetical protein | 1672 | 628 | 1672 | NA | NA | NA | NA |
| 11185v20141116 | hypothetical protein | 1673 | 629 | 1673 | NA | NA | NA | NA |
| 11186v20141116 | hypothetical protein | 630 | 630 | 1674 | NA | NA | NA | NA |
| 11187v20141116 | hypothetical protein | 631 | 631 | 1675 | NA | NA | NA | NA |
| 11188v20141116 | GntR family transcriptional regulator | 1676 | 633 | 1676 | NA | NA | NA | NA |
| 11189v20141116 | hypothetical protein Mrad2831_2999 | 634 | 634 | 1677 | NA | NA | NA | NA |
| 11190v20141116 | hypothetical protein | 635 | 635 | 1678 | NA | NA | NA | NA |
| 11191v20141116 | Hypothetical protein | 1679 | 636 | 1679 | NA | NA | NA | NA |
| 11193v20141116 | haloacid dehalogenase | 637 | 637 | 1680 | NA | NA | NA | NA |
| 11196v20141116 | hypothetical protein | 1681 | 638 | 1681 | NA | NA | NA | NA |
| 11197v20141116 | Holliday junction DNA helicase RuvB | 639 | 639 | 1682 | NA | NA | NA | NA |
| 11198v20141116 | hypothetical protein partial | 640 | 640 | 1683 | NA | NA | NA | NA |
| 11199v20141116 | hypothetical protein | 641 | 641 | 1684 | NA | NA | NA | NA |
| 11200v20141116 | hypothetical protein | 642 | 642 | 1685 | NA | NA | NA | NA |
| 11201v20141116 | hypothetical protein | 643 | 643 | 1686 | NA | NA | NA | NA |
| 11203v20141116 | hypothetical protein Mrad2831_5411 | 1687 | 644 | 1687 | NA | NA | NA | NA |
| 11204v20141116 | hypothetical protein | 645 | 645 | 1688 | NA | NA | NA | NA |
| 11206v20141116 | glycosyl transferase family protein | 1689 | 646 | 1689 | NA | NA | NA | NA |
| 11207v20141116 | hypothetical protein | 1690 | 647 | 1690 | NA | NA | NA | NA |
| 11213v20141116 | hypothetical protein Mchl_1645 | 3075 | NA | 1692 | NA | 3075 | NA | NA |
| 11233v20141116 | None | 1706 | NA | 1706 | NA | NA | NA | 4407 |
| 11447v20141116 | None | 3088 | NA | NA | NA | 3088 | 3711 | NA |
| 11497v20141116 | None | 2323 | NA | NA | 2323 | NA | NA | 4420 |
| 11506v20141116 | amidase | 2324 | NA | NA | 2324 | NA | NA | 4422 |
| 11507v20141116 | ABC transporter ATP-binding protein | 4423 | NA | NA | 2325 | NA | NA | 4423 |
| 11508v20141116 | nitrate/sulfonate/bicarbonate ABC transporter periplasmic protein | 4424 | NA | NA | 2326 | NA | NA | 4424 |
| 11511v20141116 | None | 4425 | NA | NA | 2327 | NA | NA | 4425 |
| 11576v20141116 | hypothetical protein | 3103 | NA | NA | NA | 3103 | NA | 4436 |
| 12016v20141116 | hypothetical protein | 1708 | 651 | 1708 | NA | NA | NA | NA |
| 12018v20141116 | hypothetical protein | 653 | 653 | 1709 | NA | NA | NA | NA |
| 12020v20141116 | hypothetical protein | 654 | 654 | 1710 | NA | NA | NA | NA |
| 12021v20141116 | transcriptional regulator | 655 | 655 | 1711 | NA | NA | NA | NA |
| 12022v20141116 | hypothetical protein Mrad2831_0355 | 656 | 656 | 1712 | NA | NA | NA | NA |
| 12025v20141116 | hypothetical protein | 658 | 658 | 1713 | NA | NA | NA | NA |
| 12026v20141116 | hypothetical protein | 659 | 659 | 1714 | NA | NA | NA | NA |
| 12027v20141116 | hypothetical protein | 660 | 660 | 1715 | NA | NA | NA | NA |
| 12028v20141116 | hypothetical protein | 661 | 661 | 1716 | NA | NA | NA | NA |
| 12029v20141116 | hypothetical protein | 662 | 662 | 1717 | NA | NA | NA | NA |
| 12030v20141116 | hypothetical protein | 663 | 663 | 1718 | NA | NA | NA | NA |
| 12031v20141116 | hypothetical protein | 664 | 664 | 1719 | NA | NA | NA | NA |
| 12032v20141116 | hypothetical protein | 665 | 665 | 1720 | NA | NA | NA | NA |
| 12033v20141116 | hypothetical protein | 666 | 666 | 1721 | NA | NA | NA | NA |
| 12034v20141116 | MFS transporter | 667 | 667 | 1722 | NA | NA | NA | NA |
| 12035v20141116 | 3-hydroxyisobutyrate dehydrogenase | 668 | 668 | 1723 | NA | NA | NA | NA |
| 12036v20141116 | gamma-carboxymuconolactone decarboxylase | 669 | 669 | 1724 | NA | NA | NA | NA |
| 12037v20141116 | None | 670 | 670 | 1725 | NA | NA | NA | NA |

TABLE 7-continued

Orthologous Gene Groups

| Unique Ortholog Group Identifier | Annotation | Reference. Ortholog SEQ ID NO: | NLS0017 Ortholog SEQ ID NO: | NLS0020 Ortholog SEQ ID NO: | NLS0037 Ortholog SEQ ID NO: | NLS0042 Ortholog SEQ ID NO: | NLS0065 Ortholog SEQ ID NO: | NLS0066 Ortholog SEQ ID NO: |
|---|---|---|---|---|---|---|---|---|
| 12039v20141116 | hypothetical protein | 671 | 671 | 1726 | NA | NA | NA | NA |
| 12040v20141116 | hypothetical protein | 1727 | 672 | 1727 | NA | NA | NA | NA |
| 12041v20141116 | None | 673 | 673 | 1728 | NA | NA | NA | NA |
| 12043v20141116 | None | 674 | 674 | 1729 | NA | NA | NA | NA |
| 12044v20141116 | None | 675 | 675 | 1730 | NA | NA | NA | NA |
| 12045v20141116 | None | 676 | 676 | 1731 | NA | NA | NA | NA |
| 12046v20141116 | None | 677 | 677 | 1732 | NA | NA | NA | NA |
| 12047v20141116 | None | 678 | 678 | 1733 | NA | NA | NA | NA |
| 12048v20141116 | None | 679 | 679 | 1734 | NA | NA | NA | NA |
| 12049v20141116 | hypothetical protein | 680 | 680 | 1735 | NA | NA | NA | NA |
| 12050v20141116 | hypothetical protein | 681 | 681 | 1736 | NA | NA | NA | NA |
| 12051v20141116 | None | 682 | 682 | 1737 | NA | NA | NA | NA |
| 12052v20141116 | None | 683 | 683 | 1738 | NA | NA | NA | NA |
| 12053v20141116 | hypothetical protein | 684 | 684 | 1739 | NA | NA | NA | NA |
| 12054v20141116 | None | 685 | 685 | 1740 | NA | NA | NA | NA |
| 12055v20141116 | hypothetical protein | 1741 | 686 | 1741 | NA | NA | NA | NA |
| 12056v20141116 | hypothetical protein | 687 | 687 | 1742 | NA | NA | NA | NA |
| 12057v20141116 | acetyltransferase GNAT family | 688 | 688 | 1743 | NA | NA | NA | NA |
| 12058v20141116 | hypothetical protein Msil_3108 | 689 | 689 | 1744 | NA | NA | NA | NA |
| 12059v20141116 | hypothetical protein | 690 | 690 | 1745 | NA | NA | NA | NA |
| 12060v20141116 | hypothetical protein | 691 | 691 | 1746 | NA | NA | NA | NA |
| 12061v20141116 | None | 692 | 692 | 1747 | NA | NA | NA | NA |
| 12062v20141116 | hypothetical protein | 693 | 693 | 1748 | NA | NA | NA | NA |
| 12063v20141116 | hypothetical protein | 694 | 694 | 1749 | NA | NA | NA | NA |
| 12064v20141116 | hypothetical protein | 695 | 695 | 1750 | NA | NA | NA | NA |
| 12065v20141116 | None | 696 | 696 | 1751 | NA | NA | NA | NA |
| 12066v20141116 | hypothetical protein | 697 | 697 | 1752 | NA | NA | NA | NA |
| 12067v20141116 | hypothetical protein AZOLI_2591 | 698 | 698 | 1753 | NA | NA | NA | NA |
| 12068v20141116 | None | 699 | 699 | 1754 | NA | NA | NA | NA |
| 12071v20141116 | None | 702 | 702 | NA | NA | NA | NA | 4635 |
| 12073v20141116 | hypothetical protein | 703 | 703 | 1755 | NA | NA | NA | NA |
| 12074v20141116 | hypothetical protein | 704 | 704 | 1756 | NA | NA | NA | NA |
| 12076v20141116 | hypothetical protein | 1757 | 705 | 1757 | NA | NA | NA | NA |
| 12077v20141116 | cystathionine beta-lyase | 706 | 706 | 1758 | NA | NA | NA | NA |
| 12078v20141116 | hypothetical protein | 707 | 707 | 1759 | NA | NA | NA | NA |
| 12079v20141116 | hypothetical protein | 708 | 708 | 1760 | NA | NA | NA | NA |
| 12080v20141116 | None | 709 | 709 | 1761 | NA | NA | NA | NA |
| 12081v20141116 | prevent-host-death protein | 710 | 710 | 1762 | NA | NA | NA | NA |
| 12082v20141116 | hypothetical protein | 711 | 711 | 1763 | NA | NA | NA | NA |
| 12083v20141116 | ABC transporter permease | 712 | 712 | 1764 | NA | NA | NA | NA |
| 12085v20141116 | None | 713 | 713 | 1765 | NA | NA | NA | NA |
| 12086v20141116 | hypothetical protein | 1766 | 714 | 1766 | NA | NA | NA | NA |
| 12087v20141116 | hypothetical protein | 715 | 715 | 1767 | NA | NA | NA | NA |
| 12089v20141116 | histone acetyltransferase | 716 | 716 | 1768 | NA | NA | NA | NA |
| 12091v20141116 | TetR family transcriptional regulator | 717 | 717 | 1769 | NA | NA | NA | NA |
| 12092v20141116 | None | 718 | 718 | 1770 | NA | NA | NA | NA |
| 12093v20141116 | hypothetical protein | 1771 | 719 | 1771 | NA | NA | NA | NA |
| 12095v20141116 | hypothetical protein | 720 | 720 | 1772 | NA | NA | NA | NA |
| 12097v20141116 | hypothetical protein | 722 | 722 | 1773 | NA | NA | NA | NA |
| 12099v20141116 | hypothetical protein Mrad2831_4561 | 723 | 723 | 1774 | NA | NA | NA | NA |
| 12100v20141116 | hypothetical protein | 724 | 724 | 1775 | NA | NA | NA | NA |
| 12103v20141116 | endo-1 3-beta-glucanase | 725 | 725 | 1776 | NA | NA | NA | NA |
| 12104v20141116 | hypothetical protein | 726 | 726 | 1777 | NA | NA | NA | NA |
| 12105v20141116 | hypothetical protein | 727 | 727 | 1778 | NA | NA | NA | NA |
| 12106v20141116 | hypothetical protein | 728 | 728 | 1779 | NA | NA | NA | NA |
| 12107v20141116 | hypothetical protein | 729 | 729 | 1780 | NA | NA | NA | NA |
| 12108v20141116 | hypothetical protein | 730 | 730 | 1781 | NA | NA | NA | NA |
| 12110v20141116 | hypothetical protein | 1782 | 731 | 1782 | NA | NA | NA | NA |
| 12111v20141116 | hypothetical protein | 732 | 732 | 1783 | NA | NA | NA | NA |
| 12112v20141116 | hypothetical protein | 733 | 733 | 1784 | NA | NA | NA | NA |
| 12113v20141116 | hypothetical protein | 734 | 734 | 1785 | NA | NA | NA | NA |
| 12115v20141116 | hypothetical protein | 735 | 735 | 1786 | NA | NA | NA | NA |

TABLE 7-continued

Orthologous Gene Groups

| Unique Ortholog Group Identifier | Annotation | Reference. Ortholog SEQ ID NO: | NLS0017 Ortholog SEQ ID NO: | NLS0020 Ortholog SEQ ID NO: | NLS0037 Ortholog SEQ ID NO: | NLS0042 Ortholog SEQ ID NO: | NLS0065 Ortholog SEQ ID NO: | NLS0066 Ortholog SEQ ID NO: |
|---|---|---|---|---|---|---|---|---|
| 12116v20141116 | hypothetical protein | 736 | 736 | 1787 | NA | NA | NA | NA |
| 12117v20141116 | hypothetical protein Mrad2831_2464 | 737 | 737 | 1788 | NA | NA | NA | NA |
| 12118v20141116 | hypothetical protein | 738 | 738 | 1789 | NA | NA | NA | NA |
| 12119v20141116 | hypothetical protein Mrad2831_4587 | 739 | 739 | 1790 | NA | NA | NA | NA |
| 12121v20141116 | hypothetical protein Mrad2831_4596 | 740 | 740 | 1791 | NA | NA | NA | NA |
| 12122v20141116 | aldehyde dehydrogenase | 741 | 741 | 1792 | NA | NA | NA | NA |
| 12123v20141116 | hypothetical protein | 742 | 742 | 1793 | NA | NA | NA | NA |
| 12124v20141116 | hypothetical protein | 743 | 743 | 1794 | NA | NA | NA | NA |
| 12125v20141116 | transcriptional regulator | 744 | 744 | 1795 | NA | NA | NA | NA |
| 12126v20141116 | hypothetical protein | 745 | 745 | 1796 | NA | NA | NA | NA |
| 12127v20141116 | hypothetical protein | 746 | 746 | 1797 | NA | NA | NA | NA |
| 12129v20141116 | hypothetical protein | 747 | 747 | 1798 | NA | NA | NA | NA |
| 12130v20141116 | coenzyme PQQ biosynthesis protein A | 748 | 748 | 1799 | NA | NA | NA | NA |
| 12132v20141116 | hypothetical protein | 749 | 749 | 1800 | NA | NA | NA | NA |
| 12133v20141116 | None | 750 | 750 | 1801 | NA | NA | NA | NA |
| 12134v20141116 | hypothetical protein | 751 | 751 | 1802 | NA | NA | NA | NA |
| 12135v20141116 | hypothetical protein | 752 | 752 | 1803 | NA | NA | NA | NA |
| 12136v20141116 | hypothetical protein | 753 | 753 | 1804 | NA | NA | NA | NA |
| 12137v20141116 | hypothetical protein | 754 | 754 | 1805 | NA | NA | NA | NA |
| 12138v20141116 | hypothetical protein | 755 | 755 | 1806 | NA | NA | NA | NA |
| 12140v20141116 | hypothetical protein | 1807 | 756 | 1807 | NA | NA | NA | NA |
| 12141v20141116 | Hypothetical protein | 757 | 757 | 1808 | NA | NA | NA | NA |
| 12142v20141116 | hypothetical protein | 758 | 758 | 1809 | NA | NA | NA | NA |
| 12143v20141116 | hypothetical protein | 759 | 759 | 1810 | NA | NA | NA | NA |
| 12144v20141116 | hypothetical protein | 760 | 760 | 1811 | NA | NA | NA | NA |
| 12145v20141116 | hypothetical protein | 761 | 761 | 1812 | NA | NA | NA | NA |
| 12146v20141116 | deaminase reductase | 762 | 762 | 1813 | NA | NA | NA | NA |
| 12147v20141116 | hypothetical protein | 763 | 763 | 1814 | NA | NA | NA | NA |
| 12149v20141116 | hypothetical protein | 765 | 765 | 1815 | NA | NA | NA | NA |
| 12151v20141116 | histidine kinase | 767 | 767 | 1816 | NA | NA | NA | NA |
| 12152v20141116 | hypothetical protein | 768 | 768 | 1817 | NA | NA | NA | NA |
| 12153v20141116 | hypothetical protein | 769 | 769 | 1818 | NA | NA | NA | NA |
| 12154v20141116 | hypothetical protein | 770 | 770 | 1819 | NA | NA | NA | NA |
| 12155v20141116 | hypothetical protein | 771 | 771 | 1820 | NA | NA | NA | NA |
| 12160v20141116 | hypothetical protein | 772 | 772 | 1821 | NA | NA | NA | NA |
| 12161v20141116 | hypothetical protein MexAM1_META1p3214 | 4637 | 773 | NA | NA | NA | NA | 4637 |
| 12162v20141116 | putative transmembrane protein | 774 | 774 | 1822 | NA | NA | NA | NA |
| 12164v20141116 | hypothetical protein | 775 | 775 | 1823 | NA | NA | NA | NA |
| 12165v20141116 | ABC transporter substrate-binding protein family 5 | 776 | 776 | NA | 2328 | NA | NA | NA |
| 12166v20141116 | signal peptide protein | 1824 | 777 | 1824 | NA | NA | NA | NA |
| 12167v20141116 | hypothetical protein | 778 | 778 | 1825 | NA | NA | NA | NA |
| 12168v20141116 | hypothetical protein | 779 | 779 | 1826 | NA | NA | NA | NA |
| 12169v20141116 | hypothetical protein | 780 | 780 | 1827 | NA | NA | NA | NA |
| 12170v20141116 | hypothetical protein | 781 | 781 | 1828 | NA | NA | NA | NA |
| 12171v20141116 | hypothetical protein | 782 | 782 | 1829 | NA | NA | NA | NA |
| 12172v20141116 | hypothetical protein | 783 | 783 | 1830 | NA | NA | NA | NA |
| 12173v20141116 | hypothetical protein | 784 | 784 | 1831 | NA | NA | NA | NA |
| 12174v20141116 | adenylate cyclase | 785 | 785 | 1832 | NA | NA | NA | NA |
| 12175v20141116 | hypothetical protein | 786 | 786 | 1833 | NA | NA | NA | NA |
| 12176v20141116 | hypothetical protein | 787 | 787 | 1834 | NA | NA | NA | NA |
| 12177v20141116 | hypothetical protein Mrad2831_3657 | 788 | 788 | 1835 | NA | NA | NA | NA |
| 12178v20141116 | hypothetical protein | 789 | 789 | 1836 | NA | NA | NA | NA |
| 12179v20141116 | hypothetical protein | 790 | 790 | 1837 | NA | NA | NA | NA |
| 12180v20141116 | hypothetical protein | 791 | 791 | 1838 | NA | NA | NA | NA |
| 12185v20141116 | None | 793 | 793 | 1839 | NA | NA | NA | NA |
| 12186v20141116 | hypothetical protein | 1840 | 794 | 1840 | NA | NA | NA | NA |
| 12187v20141116 | hypothetical protein | 1841 | 795 | 1841 | NA | NA | NA | NA |
| 12189v20141116 | hypothetical protein | 796 | 796 | 1843 | NA | NA | NA | NA |
| 12190v20141116 | hypothetical protein | 797 | 797 | 1844 | NA | NA | NA | NA |
| 12191v20141116 | hypothetical protein | 1845 | 798 | 1845 | NA | NA | NA | NA |
| 12192v20141116 | oxidoreductase | 799 | 799 | 1846 | NA | NA | NA | NA |

TABLE 7-continued

Orthologous Gene Groups

| Unique Ortholog Group Identifier | Annotation | Reference. Ortholog SEQ ID NO: | NLS0017 Ortholog SEQ ID NO: | NLS0020 Ortholog SEQ ID NO: | NLS0037 Ortholog SEQ ID NO: | NLS0042 Ortholog SEQ ID NO: | NLS0065 Ortholog SEQ ID NO: | NLS0066 Ortholog SEQ ID NO: |
|---|---|---|---|---|---|---|---|---|
| 12193v20141116 | hypothetical protein | 800 | 800 | 1847 | NA | NA | NA | NA |
| 12194v20141116 | hypothetical protein | 801 | 801 | 1848 | NA | NA | NA | NA |
| 12195v20141116 | hypothetical protein | 1849 | 802 | 1849 | NA | NA | NA | NA |
| 12196v20141116 | hypothetical protein | 803 | 803 | 1850 | NA | NA | NA | NA |
| 12197v20141116 | hypothetical protein | 1851 | 804 | 1851 | NA | NA | NA | NA |
| 12198v20141116 | porin | 1852 | 805 | 1852 | NA | NA | NA | NA |
| 12200v20141116 | hypothetical protein | 1853 | 806 | 1853 | NA | NA | NA | NA |
| 12202v20141116 | hypothetical protein Mrad2831_3327 | 807 | 807 | 1854 | NA | NA | NA | NA |
| 12207v20141116 | hypothetical protein | 809 | 809 | 1855 | NA | NA | NA | NA |
| 12208v20141116 | hypothetical protein | 810 | 810 | 1856 | NA | NA | NA | NA |
| 12209v20141116 | hypothetical protein | 811 | 811 | 1857 | NA | NA | NA | NA |
| 12210v20141116 | hypothetical protein | 812 | 812 | 1858 | NA | NA | NA | NA |
| 12212v20141116 | hypothetical protein | 813 | 813 | 1859 | NA | NA | NA | NA |
| 12214v20141116 | None | 814 | 814 | 1860 | NA | NA | NA | NA |
| 12217v20141116 | hypothetical protein | 816 | 816 | 1861 | NA | NA | NA | NA |
| 12218v20141116 | hypothetical protein | 817 | 817 | 1862 | NA | NA | NA | NA |
| 12219v20141116 | hypothetical protein | 818 | 818 | 1863 | NA | NA | NA | NA |
| 12220v20141116 | RNA polymerase sigma factor SigJ | 819 | 819 | 1864 | NA | NA | NA | NA |
| 12221v20141116 | hypothetical protein | 820 | 820 | 1865 | NA | NA | NA | NA |
| 12222v20141116 | hypothetical protein | 1866 | 821 | 1866 | NA | NA | NA | NA |
| 12223v20141116 | hypothetical protein | 822 | 822 | 1867 | NA | NA | NA | NA |
| 12226v20141116 | hypothetical protein | 823 | 823 | 1868 | NA | NA | NA | NA |
| 12227v20141116 | hypothetical protein | 824 | 824 | 1869 | NA | NA | NA | NA |
| 12228v20141116 | None | 825 | 825 | 1870 | NA | NA | NA | NA |
| 12230v20141116 | hypothetical protein | 1871 | 826 | 1871 | NA | NA | NA | NA |
| 12231v20141116 | hypothetical protein | 1872 | 827 | 1872 | NA | NA | NA | NA |
| 12232v20141116 | None | 828 | 828 | 1873 | NA | NA | NA | NA |
| 12233v20141116 | hypothetical protein | 1874 | 829 | 1874 | NA | NA | NA | NA |
| 12234v20141116 | PAS domain-containing protein | 830 | 830 | 1875 | NA | NA | NA | NA |
| 12235v20141116 | hypothetical protein | 1876 | 831 | 1876 | NA | NA | NA | NA |
| 12236v20141116 | hypothetical protein | 832 | 832 | 1877 | NA | NA | NA | NA |
| 12237v20141116 | None | 833 | 833 | 1878 | NA | NA | NA | NA |
| 12239v20141116 | hypothetical protein | 834 | 834 | 1879 | NA | NA | NA | NA |
| 12240v20141116 | None | 835 | 835 | 1880 | NA | NA | NA | NA |
| 12241v20141116 | hypothetical protein | 836 | 836 | 1881 | NA | NA | NA | NA |
| 12242v20141116 | hypothetical protein | 837 | 837 | 1882 | NA | NA | NA | NA |
| 12244v20141116 | AraC family transcriptional regulator | 838 | 838 | 1883 | NA | NA | NA | NA |
| 12245v20141116 | hypothetical protein | 839 | 839 | 1884 | NA | NA | NA | NA |
| 12246v20141116 | hypothetical protein | 1885 | 840 | 1885 | NA | NA | NA | NA |
| 12248v20141116 | hypothetical protein | 1886 | 842 | 1886 | NA | NA | NA | NA |
| 12251v20141116 | hypothetical protein | 844 | 844 | 1887 | NA | NA | NA | NA |
| 12252v20141116 | porin | 845 | 845 | 1888 | NA | NA | NA | NA |
| 12270v20141116 | hypothetical protein | 4642 | NA | 1900 | NA | NA | NA | 4642 |
| 12282v20141116 | carbohydrate-selective porin OprB | 3725 | NA | 1905 | NA | NA | 3725 | NA |
| 13420v20141116 | hypothetical protein Mchl_5363 | 3739 | NA | NA | NA | 3131 | 3739 | NA |
| 14119v20141116 | hypothetical protein BBta_6573 | 848 | 848 | NA | NA | 3156 | NA | NA |
| 14131v20141116 | hypothetical protein CcrKarma_gp008 | 853 | 853 | 1912 | NA | NA | NA | NA |
| 14132v20141116 | None | 854 | 854 | 1913 | NA | NA | NA | NA |
| 14133v20141116 | None | 855 | 855 | 1914 | NA | NA | NA | NA |
| 14134v20141116 | None | 856 | 856 | 1915 | NA | NA | NA | NA |
| 14136v20141116 | None | 857 | 857 | 1916 | NA | NA | NA | NA |
| 14137v20141116 | None | 858 | 858 | 1917 | NA | NA | NA | NA |
| 14138v20141116 | None | 859 | 859 | 1918 | NA | NA | NA | NA |
| 14139v20141116 | hypothetical protein | 860 | 860 | 1919 | NA | NA | NA | NA |
| 14152v20141116 | glycosyl transferase family protein | 867 | 867 | 1920 | NA | NA | NA | NA |
| 14156v20141116 | None | 869 | 869 | 1921 | NA | NA | NA | NA |
| 14168v20141116 | integrase catalytic region (modular protein) | 1923 | 871 | 1923 | NA | NA | NA | NA |
| 14170v20141116 | hypothetical protein | 1925 | 872 | 1925 | NA | NA | NA | NA |
| 14172v20141116 | Fis family transcriptional regulator | 873 | 873 | NA | NA | NA | NA | 4875 |

TABLE 7-continued

Orthologous Gene Groups

| Unique Ortholog Group Identifier | Annotation | Reference. Ortholog SEQ ID NO: | NLS0017 Ortholog SEQ ID NO: | NLS0020 Ortholog SEQ ID NO: | NLS0037 Ortholog SEQ ID NO: | NLS0042 Ortholog SEQ ID NO: | NLS0065 Ortholog SEQ ID NO: | NLS0066 Ortholog SEQ ID NO: |
|---|---|---|---|---|---|---|---|---|
| 14174v20141116 | hypothetical protein Mrad2831_5180 | 874 | 874 | 1926 | NA | NA | NA | NA |
| 14176v20141116 | hypothetical protein | 1927 | 875 | 1927 | NA | NA | NA | NA |
| 14181v20141116 | magnesium chelatase | 878 | 878 | 1929 | NA | NA | NA | NA |
| 14182v20141116 | hypothetical protein | 879 | 879 | 1930 | NA | NA | NA | NA |
| 14189v20141116 | hypothetical protein | 884 | 884 | 1931 | NA | NA | NA | NA |
| 14190v20141116 | None | 1932 | 885 | 1932 | NA | NA | NA | NA |
| 14196v20141116 | WGR domain-containing protein | 1934 | 889 | 1934 | NA | NA | NA | NA |
| 14200v20141116 | hypothetical protein | 893 | 893 | 1935 | NA | NA | NA | NA |
| 14291v20141116 | hypothetical protein | 2020 | NA | 2020 | 2342 | NA | NA | NA |
| 14320v20141116 | membrane protein | 3160 | NA | 2046 | NA | 3160 | NA | NA |
| 14649v20141116 | dienelactone hydrolase | 3173 | NA | NA | NA | 3173 | 3768 | NA |
| 14657v20141116 | hypothetical protein | 3180 | NA | NA | NA | 3180 | NA | 4881 |
| 15376v20141116 | transcriptional regulator | 2058 | 904 | 2058 | NA | NA | NA | NA |
| 15391v20141116 | hypothetical protein | 916 | 916 | 2059 | NA | NA | NA | NA |
| 15392v20141116 | None | 917 | 917 | 2060 | NA | NA | NA | NA |
| 15394v20141116 | RluA family pseudouridine synthase | 918 | 918 | 2061 | NA | NA | NA | NA |
| 15437v20141116 | PAS sensor protein | 2063 | 938 | 2063 | NA | NA | NA | NA |
| 15441v20141116 | integrase catalytic subunit | 940 | 940 | 2064 | NA | NA | NA | NA |
| 15442v20141116 | hypothetical protein | 2370 | 941 | NA | 2370 | NA | NA | NA |
| 15451v20141116 | hypothetical protein | 946 | 946 | 2065 | NA | NA | NA | NA |
| 15452v20141116 | molecular chaperone GroES | 947 | 947 | 2066 | NA | NA | NA | NA |
| 15460v20141116 | epimerase | 952 | 952 | 2067 | NA | NA | NA | NA |
| 15489v20141116 | hypothetical protein | 2371 | NA | 2085 | 2371 | NA | NA | NA |
| 15815v20141116 | hypothetical protein | 3787 | NA | NA | 2393 | NA | 3787 | NA |
| 17689v20141116 | None | 993 | 993 | 2112 | NA | NA | NA | NA |
| 17695v20141116 | hypothetical protein | 999 | 999 | 2113 | NA | NA | NA | NA |
| 17705v20141116 | None | 1006 | 1006 | 2114 | NA | NA | NA | NA |
| 17706v20141116 | hypothetical protein | 2406 | NA | NA | 2406 | 3251 | NA | NA |
| 17707v20141116 | hypothetical protein | 1007 | 1007 | 2115 | NA | NA | NA | NA |
| 17708v20141116 | None | 1008 | 1008 | 2116 | NA | NA | NA | NA |
| 17709v20141116 | None | 1009 | 1009 | 2117 | NA | NA | NA | NA |
| 17710v20141116 | None | 1010 | 1010 | 2118 | NA | NA | NA | NA |
| 17731v20141116 | integrase catalytic subunit | 3252 | 1024 | NA | NA | 3252 | NA | NA |
| 17732v20141116 | putative aspartate racemase | 2407 | 1025 | NA | 2407 | NA | NA | NA |
| 17757v20141116 | None | 2119 | 1041 | 2119 | NA | NA | NA | NA |
| 17759v20141116 | hypothetical protein | 2120 | 1042 | 2120 | NA | NA | NA | NA |
| 17795v20141116 | hypothetical protein Mrad2831_4255 | 1073 | 1073 | 2122 | NA | NA | NA | NA |
| 17807v20141116 | glycosyl transferase | 1085 | 1085 | NA | 2409 | NA | NA | NA |
| 17808v20141116 | hypothetical protein | 2123 | 1086 | 2123 | NA | NA | NA | NA |
| 17857v20141116 | polar amino acid ABC transporter permease | 2164 | NA | 2164 | 2410 | NA | NA | NA |
| 18264v20141116 | hypothetical protein Rleg2_4164 | 3258 | NA | NA | 2416 | 3258 | NA | NA |

REFERENCES FOR EXAMPLE 8

1. Miller J R, Koren S, Sutton G (2010) Assembly algorithms for next-generation sequencing data. Genomics 95: 315-327.
2. Zerbino D R, Birney E (2008) Velvet: algorithms for de novo short read assembly using de Bruijn graphs. Genome Res 18: 821-829.
3. Delcher A L, Bratke K A, Powers E C, Salzberg S L (2007) Identifying bacterial genes and endosymbiont DNA with Glimmer. Bioinformatics 23: 673-679.
4. Lowe T M, Eddy S R (1997) tRNAscan-SE: a program for improved detection of transfer RNA genes in genomic sequence. Nucleic Acids Res 25: 955-964.
5. Lagesen K, Hallin P, Rodland E A, Staerfeldt H H, Rognes T, et al. (2007) RNAmmer: consistent and rapid annotation of ribosomal RNA genes. Nucleic Acids Res 35: 3100-3108.
6. Cantarel B, Korf I, Robb S, et al. (2008) MAKER: An easy-to-use annotation pipeline designed for emerging model organism genomes. Genome Research 18: 188-196.
7. Altschul S F, Madden T L, Schaffer A A, Zhang J, Zhang Z, et al. (1997) Gapped BLAST and PSI-BLAST: a new generation of protein database search programs. Nucleic Acids Res 25: 3389-3402.
8. Eddy S R (2009) A new generation of homology search tools based on probabilistic inference. Genome Inform 23: 205-211.

9. Haft D H, Selengut J D, White O (2003) The TIGRFAMs database of protein families. Nucleic Acids Res 31: 371-373.
10. Tatusov R L, Fedorova N D, Jackson J D, Jacobs A R, Kiryutin B, et al. (2003) The COG database: an updated version includes eukaryotes. BMC Bioinformatics 4: 41.
11. Suzek B E, Huang H, McGarvey P, Mazumder R, Wu C H (2007) UniRef: comprehensive and non-redundant UniProt reference clusters. Bioinformatics 23: 1282-1288.
12. Li H. and Durbin R. (2009) Fast and accurate short read alignment with Burrows-Wheeler Transform. Bioinformatics, 25:1754-60

The inclusion of various references herein is not to be construed as any admission by the Applicants that the references constitute prior art. Applicants expressly reserve their right to challenge any allegations of unpatentability of inventions disclosed herein over the references included herein.

Having illustrated and described the principles of the present invention, it should be apparent to persons skilled in the art that the invention can be modified in arrangement and detail without departing from such principles.

Although the materials and methods of this invention have been described in terms of various embodiments and illustrative examples, it will be apparent to those of skill in the art that variations can be applied to the materials and methods described herein without departing from the concept, spirit and scope of the invention. All such similar substitutes and modifications apparent to those skilled in the art are deemed to be within the spirit, scope and concept of the invention as defined by the appended claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10212939B2). An electronic copy of the "Sequence Listing" will also be available from the USPTO upon request and payment of the fee set forth in 37 CFR 1.19(b)(3).

What is claimed is:

1. A plant, plant part or seed that is coated or partially coated with a *Methylobacterium*-containing composition, wherein said composition comprises (a) a *Methylobacterium* fermentation product that is essentially free of contaminating microorganisms, wherein the *Methylobacterium* is deposited strain NLS0017 (NRRL B-50931); and (b) an agriculturally acceptable excipient, adjuvant, or combination thereof; and wherein the plant, plant part, or seed is a peanut (*Arachis hypogaea*) or lettuce (*Lactuca sativa*) plant, plant part, or seed.

2. A plant, plant part, or seed that is coated or partially coated with a composition comprising: (i) a solid substance wherein a mono-culture or co-culture of *Methylobacterium* is adhered thereto by having been grown on said solid substance, wherein a *Methylobacterium* in said mono-culture or co-culture is deposited strain NLS0017 (NRRL B-50931); and (ii) an agriculturally acceptable adjuvant, excipient, or combination thereof; and wherein the plant, plant part, or seed is a peanut (*Arachis hypogaea*) or lettuce (*Lactuca sativa*) plant, plant part, or seed.

3. The plant, plant part, or seed of claim 2, wherein the *Methylobacterium* is at a titer of at least about $1\times10^4$ colony-forming units per milliliter.

4. The plant, plant part, or seed of claim 2, wherein said solid substance is sand, silt, soil, clay, ash, charcoal, diatomaceous earth, ground glass, glass beads, ground ceramic materials, ceramic beads, polymers, polymeric beads, salt crystals, animal particulate matters, or plant particulate matters.

5. The plant, plant part, or seed of claim 2, wherein said composition further comprises a population of one or more plant beneficial microorganisms other than *Methylobacterium*.

6. The plant, plant part, or seed of claim 2, wherein said agriculturally acceptable adjuvant is a wetter, a sticker, a penetrant, an extender, or a humectant that enhances product efficacy or ease of product application.

7. The plant, plant part, or seed of claim 2, wherein said composition further comprises a pesticide.

8. The plant, plant part, or seed of claim 7, wherein said pesticide does not substantially inhibit growth of the *Methylobacterium* by more than 50% when the composition is applied to a plant or plant part in comparison to when a composition lacking the pesticide is applied to a plant or plant part.

9. The plant, plant part, or seed of claim 6, wherein said sticker comprises a polyvinyl acetate polymer or copolymer, polyvinylpyrrolidone-vinyl acetate polymer or copolymer, polyvinyl alcohol polymer or copolymer, latex polymer, alginate, acrylic copolymer, or acrylamide polymer or copolymer.

10. The plant, plant part, or seed of claim 2, wherein said adjuvant comprises a surfactant, dispersant, anticaking-agent, foam-control agent, or a dye.

11. The plant, plant part, or seed of claim 1, wherein said composition provides for a plant production improvement selected from increased yield, improved shoot biomass and improved root development in comparison to an untreated plant.

12. The plant, plant part or seed of claim 1, wherein said fermentation product comprises a solid substance with adherent *Methylobacterium* grown thereon, or an emulsion with *Methylobacterium* grown therein.

13. The plant, plant part, or seed of claim 1, wherein said composition further comprises a population of one or more plant beneficial microorganisms other than *Methylobacterium*.

14. The plant, plant part, or seed of claim 1, wherein said agriculturally acceptable adjuvant is a wetter, a sticker, a penetrant, an extender, or a humectant that enhances product efficacy or ease of product application.

15. The plant, plant part, or seed of claim 1, wherein said composition further comprises a pesticide.

16. The plant, plant part, or seed of claim 15, wherein said pesticide does not substantially inhibit growth of the *Methylobacterium* by more than 50% when the composition is applied to a plant or plant part in comparison to when a composition lacking the pesticide is applied to a plant or plant part.

17. The plant, plant part, or seed of claim 14, wherein said sticker comprises a polyvinyl acetate polymer or copolymer, polyvinylpyrrolidone-vinyl acetate polymer or copolymer, polyvinyl alcohol polymer or copolymer, latex polymer, alginate, acrylic copolymer, or acrylamide polymer or copolymer.

18. The plant, plant part, or seed of claim 1, wherein said adjuvant comprises a surfactant, dispersant, anticaking-agent, foam-control agent, or a dye.

19. The plant, plant part, or seed of claim 1, wherein the *Methylobacterium* is at a titer of at least about $5 \times 10^8$ colony-forming units per milliliter.

20. The plant, plant part, or seed of claim 2, wherein the solid substance with adherent *Methylobacterium* grown thereon has a *Methylobacterium* titer of at least about $5 \times 10^8$ CFU/gram.

* * * * *